United States Patent
Songer et al.

(10) Patent No.: US 7,918,878 B2
(45) Date of Patent: Apr. 5, 2011

(54) MINIMALLY INVASIVE SURGICAL SYSTEM

(75) Inventors: Matthew N. Songer, Marquette, MI (US); Matthew P. Gephart, Marquette, MI (US); Philip Berman, Marquette, MI (US); Bobby Steven Lynch, Charlotte, NC (US); Ernie N. Corrao, Bethel, CT (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 362 days.

(21) Appl. No.: 11/844,277

(22) Filed: Aug. 23, 2007

(65) Prior Publication Data

US 2008/0045956 A1 Feb. 21, 2008

Related U.S. Application Data

(63) Continuation of application No. PCT/US06/006684, filed on Feb. 23, 2006.

(60) Provisional application No. 60/722,604, filed on Sep. 29, 2005, provisional application No. 60/655,983, filed on Feb. 23, 2005.

(51) Int. Cl.
*A61B 17/88* (2006.01)

(52) U.S. Cl. ................................................ 606/279

(58) Field of Classification Search .......... 606/270, 606/279, 265, 264, 86 A; 623/17.11–17.16; A61B 17/70
See application file for complete search history.

(56) References Cited

U.S. PATENT DOCUMENTS

| | | |
|---|---|---|
| 3,844,291 A | 10/1974 | Moen |
| 5,020,519 A | 6/1991 | Hayes et al. |
| 5,171,279 A | 12/1992 | Mathews |
| 5,242,443 A | 9/1993 | Kambin |
| 5,258,005 A | 11/1993 | Christian |
| 5,507,772 A | 4/1996 | Shutt et al. |
| 5,683,392 A | 11/1997 | Richelsoph et al. |
| 5,720,751 A | 2/1998 | Jackson |
| 5,782,833 A | 7/1998 | Haider |
| 5,863,293 A | 1/1999 | Richelsoph |

(Continued)

FOREIGN PATENT DOCUMENTS

EP 1858422 11/2008

(Continued)

OTHER PUBLICATIONS

Foley, M.D., Kevin T., Schwender, MD., James D., and Rouben, MD., David P., Pyrametrix® Advance: Instrument Set Technique, surgical technique brochure provided by the manufacturer, Medtronic Sofamore Danek Inc., 2005.

(Continued)

*Primary Examiner* — Eduardo C Robert
*Assistant Examiner* — Nicholas Plionis
(74) *Attorney, Agent, or Firm* — Fitch, Even, Tabin & Flannery

(57) ABSTRACT

A minimally invasive surgical system for implanting pedicle screw assemblies to be connected by a spinal rod is disclosed. In one form, the system includes a plurality of holding mechanisms for the pedicle screw assemblies, each holding mechanism for being inserted through an incision and configured to receive tools along an axis thereof for driving a screw anchor of the pedicle screw assembly into a vertebra and securing the spinal rod thereto and a rod inserter that is configured to adjustably hold the rod and insert the rod through a common incision with one of the holding mechanism for being fed into position in an initial direction that is transverse to the axes of the holding mechanisms.

28 Claims, 64 Drawing Sheets

U.S. PATENT DOCUMENTS

| | | | |
|---|---|---|---|
| 5,941,885 A | 8/1999 | Jackson | |
| 5,954,635 A | 9/1999 | Foley et al. | |
| 5,964,760 A | 10/1999 | Richelsoph | |
| 5,964,761 A | 10/1999 | Kambin | |
| 6,010,503 A | 1/2000 | Richelsoph | |
| 6,090,111 A | 7/2000 | Nichols | |
| 6,096,044 A | 8/2000 | Boyd et al. | |
| 6,132,432 A | 10/2000 | Richelsoph | |
| 6,174,311 B1 | 1/2001 | Branch et al. | |
| 6,226,548 B1 | 5/2001 | Foley et al. | |
| 6,287,313 B1 | 9/2001 | Sasso | |
| 6,355,040 B1 | 3/2002 | Richelsoph et al. | |
| 6,485,491 B1 | 11/2002 | Farris et al. | |
| 6,485,591 B1 | 11/2002 | Nakao et al. | |
| 6,530,929 B1 | 3/2003 | Justis et al. | |
| 6,565,565 B1 | 5/2003 | Yuan et al. | |
| 6,648,888 B1 | 11/2003 | Shluzas | |
| 6,660,006 B2 | 12/2003 | Markworth et al. | |
| 6,666,866 B2 | 12/2003 | Martz et al. | |
| 6,749,614 B2 | 6/2004 | Teitelbaum et al. | |
| 6,755,829 B1 | 6/2004 | Bono et al. | |
| 6,793,656 B1 | 9/2004 | Mathews | |
| 6,875,212 B2 | 4/2005 | Shaolian et al. | |
| 6,951,538 B2 | 10/2005 | Ritland | |
| 6,964,667 B2 | 11/2005 | Shaolian et al. | |
| 7,081,117 B2 | 7/2006 | Bono et al. | |
| 7,083,621 B2 | 8/2006 | Shaolian et al. | |
| 7,090,674 B2 | 8/2006 | Doubler | |
| 7,125,426 B2 | 10/2006 | Bono et al. | |
| 7,141,051 B2 | 11/2006 | Janowski et al. | |
| 7,476,240 B2 | 1/2009 | Raymond et al. | |
| 2002/0120272 A1* | 8/2002 | Yuan et al. | 606/61 |
| 2002/0161368 A1 | 10/2002 | Foley et al. | |
| 2003/0004519 A1* | 1/2003 | Torode et al. | 606/104 |
| 2003/0060826 A1 | 3/2003 | Foley et al. | |
| 2003/0073998 A1* | 4/2003 | Pagliuca et al. | 606/61 |
| 2003/0125742 A1 | 7/2003 | Yuan | |
| 2003/0208203 A1 | 11/2003 | Lim et al. | |
| 2003/0225408 A1 | 12/2003 | Nichols et al. | |
| 2003/0229347 A1 | 12/2003 | Sherman et al. | |
| 2003/0236447 A1 | 12/2003 | Ritland | |
| 2004/0039384 A1 | 2/2004 | Boehm, Jr. et al. | |
| 2004/0059333 A1 | 3/2004 | Carl et al. | |
| 2004/0082960 A1 | 4/2004 | Davison | |
| 2004/0092952 A1 | 5/2004 | Newton et al. | |
| 2004/0133201 A1 | 7/2004 | Shluzas et al. | |
| 2004/0138662 A1 | 7/2004 | Landry et al. | |
| 2004/0143265 A1 | 7/2004 | Landry et al. | |
| 2004/0147937 A1* | 7/2004 | Dunbar et al. | 606/99 |
| 2004/0172022 A1 | 9/2004 | Landry et al. | |
| 2004/0215190 A1 | 10/2004 | Nguyen et al. | |
| 2004/0230100 A1 | 11/2004 | Shluzas | |
| 2004/0230191 A1 | 11/2004 | Frey et al. | |
| 2005/0004593 A1 | 1/2005 | Simonson | |
| 2005/0021030 A1 | 1/2005 | Pagliuca et al. | |
| 2005/0021031 A1 | 1/2005 | Foley et al. | |
| 2005/0033297 A1 | 2/2005 | Davison | |
| 2005/0033299 A1 | 2/2005 | Shluzas | |
| 2005/0065516 A1 | 3/2005 | Jahng | |
| 2005/0065517 A1 | 3/2005 | Chin | |
| 2005/0075540 A1 | 4/2005 | Shluzas et al. | |
| 2005/0075644 A1 | 4/2005 | Dipoto | |
| 2005/0080418 A1 | 4/2005 | Simonson et al. | |
| 2005/0085813 A1 | 4/2005 | Spitler et al. | |
| 2005/0090822 A1 | 4/2005 | DiPoto | |
| 2005/0090824 A1 | 4/2005 | Shluzas et al. | |
| 2005/0090833 A1 | 4/2005 | Dipoto | |
| 2005/0090899 A1 | 4/2005 | Dipoto | |
| 2005/0107789 A1 | 5/2005 | Sweeny | |
| 2005/0131408 A1 | 6/2005 | Sicvol et al. | |
| 2005/0131419 A1 | 6/2005 | McCord et al. | |
| 2005/0131420 A1 | 6/2005 | Techiera et al. | |
| 2005/0131421 A1 | 6/2005 | Anderson et al. | |
| 2005/0131422 A1 | 6/2005 | Anderson et al. | |
| 2005/0137593 A1* | 6/2005 | Gray et al. | 606/61 |
| 2005/0149022 A1 | 7/2005 | Shaolian et al. | |
| 2005/0149036 A1 | 7/2005 | Varieur et al. | |
| 2005/0149053 A1 | 7/2005 | Varieur et al. | |
| 2005/0154389 A1 | 7/2005 | Selover et al. | |
| 2005/0159651 A1 | 7/2005 | Raymond et al. | |
| 2005/0171540 A1 | 8/2005 | Lim et al. | |
| 2005/0171551 A1 | 8/2005 | Sukovich et al. | |
| 2005/0192570 A1 | 9/2005 | Jackson | |
| 2005/0192579 A1 | 9/2005 | Jackson | |
| 2005/0192589 A1 | 9/2005 | Raymond et al. | |
| 2005/0215999 A1 | 9/2005 | Birkmeyer | |
| 2005/0216002 A1 | 9/2005 | Simonson | |
| 2005/0228380 A1 | 10/2005 | Moore | |
| 2005/0228400 A1 | 10/2005 | Chao et al. | |
| 2005/0245942 A1 | 11/2005 | Dipoto | |
| 2005/0251192 A1 | 11/2005 | Shluzas et al. | |
| 2005/0273131 A1 | 12/2005 | Shluzas et al. | |
| 2005/0273132 A1 | 12/2005 | Shluzas et al. | |
| 2005/0273133 A1 | 12/2005 | Shluzas et al. | |
| 2005/0288671 A1 | 12/2005 | Yuan et al. | |
| 2006/0036244 A1 | 2/2006 | Spitler et al. | |
| 2006/0074445 A1 | 4/2006 | Gerber et al. | |
| 2006/0089651 A1 | 4/2006 | Trudeau et al. | |
| 2006/0111714 A1 | 5/2006 | Foley | |
| 2006/0155278 A1 | 7/2006 | Warnick | |
| 2006/0173456 A1 | 8/2006 | Hawkes et al. | |
| 2006/0200135 A1 | 9/2006 | Sherman et al. | |
| 2006/0229614 A1 | 10/2006 | Foley et al. | |
| 2006/0235393 A1 | 10/2006 | Bono et al. | |
| 2006/0241600 A1 | 10/2006 | Ensign et al. | |
| 2006/0247630 A1 | 11/2006 | Lott et al. | |
| 2006/0247636 A1 | 11/2006 | Yuan et al. | |
| 2006/0264962 A1 | 11/2006 | Chin et al. | |
| 2006/0276791 A1 | 12/2006 | Shluzas | |
| 2006/0276792 A1 | 12/2006 | Ensign et al. | |
| 2007/0055235 A1 | 3/2007 | Janowski et al. | |
| 2007/0078460 A1 | 4/2007 | Frigg et al. | |
| 2007/0093817 A1 | 4/2007 | Barrus et al. | |
| 2007/0093826 A1 | 4/2007 | Hawkes et al. | |
| 2007/0093827 A1 | 4/2007 | Warnick | |
| 2007/0185491 A1 | 8/2007 | Foley et al. | |
| 2007/0198015 A1 | 8/2007 | Foley et al. | |
| 2007/0225711 A1 | 9/2007 | Ensign | |
| 2008/0039839 A1 | 2/2008 | Songer et al. | |
| 2008/0039840 A1 | 2/2008 | Songer et al. | |
| 2008/0154277 A1 | 6/2008 | Machalk et al. | |
| 2008/0195155 A1 | 8/2008 | Hoffman et al. | |
| 2008/0228233 A1 | 9/2008 | Hoffman et al. | |

FOREIGN PATENT DOCUMENTS

| | | |
|---|---|---|
| WO | 2004047650 | 10/2004 |
| WO | 2008024937 | 2/2008 |

OTHER PUBLICATIONS

An International Search Report dated Sep. 20, 2007, from the International Bureau in Corresponding International (PCT) Application No. PCT/US2006/06684.

A Written Opinion dated Sep. 20, 2007, from the International Searching Authority in corresponding International (PCT) Application No. PCT/US2006/06684.

An International Search Report dated Sep. 22, 2008, from the International Bureau in related International (PCT) Application No. PCT/US2007/76687.

A Written Opinion dated Sep. 22, 2008, from the International Searching Authority in related International (PCT) Application No. PCT/US2007/76687.

* cited by examiner

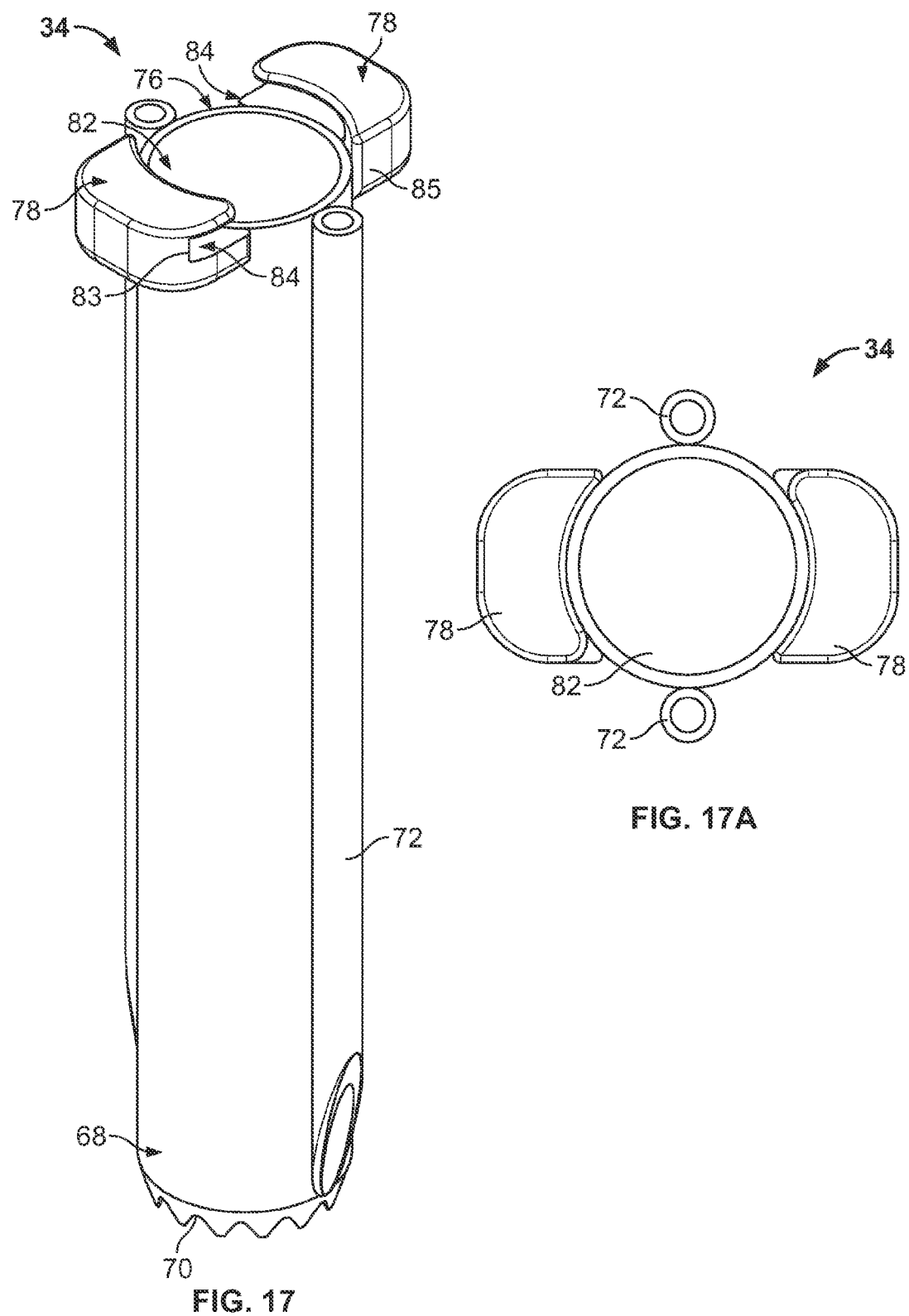

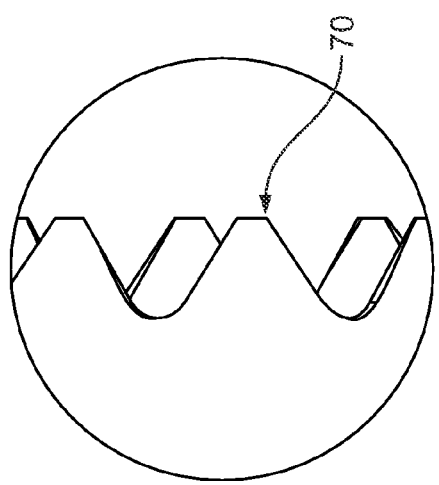
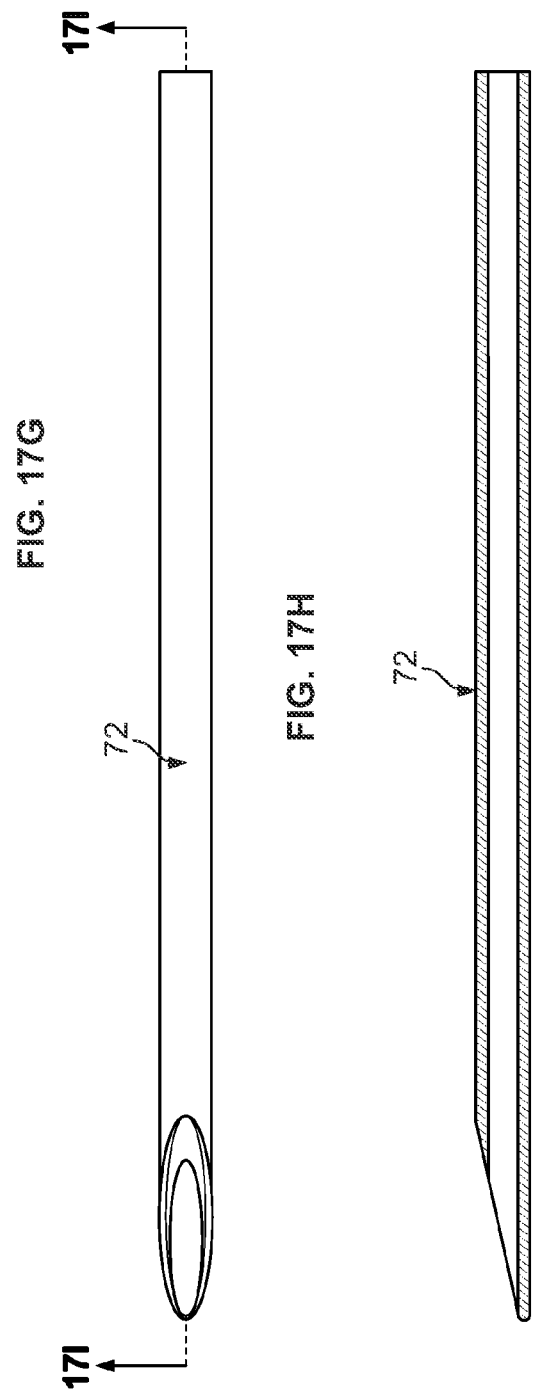
FIG. 17G
FIG. 17F
FIG. 17H
FIG. 17I

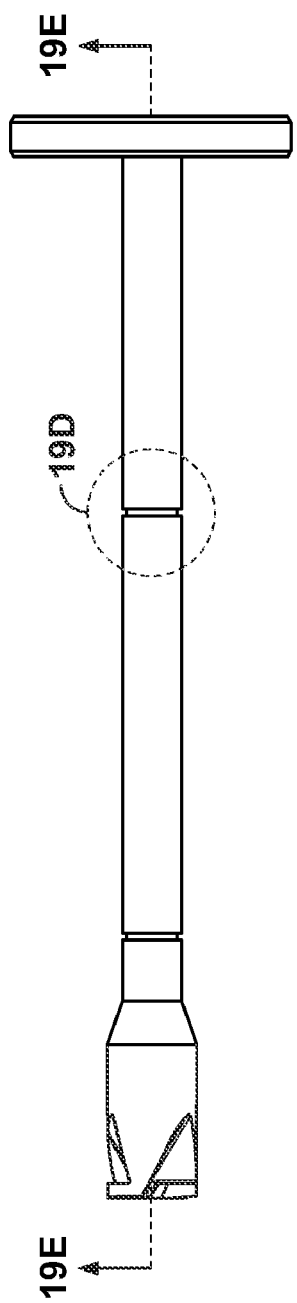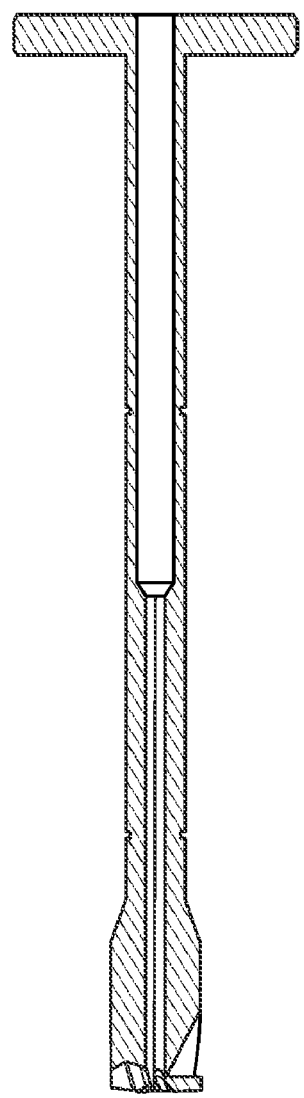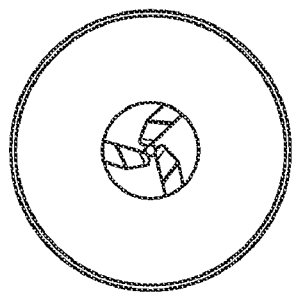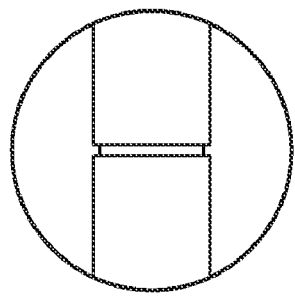
FIG. 19C
FIG. 19E
FIG. 19B
FIG. 19D

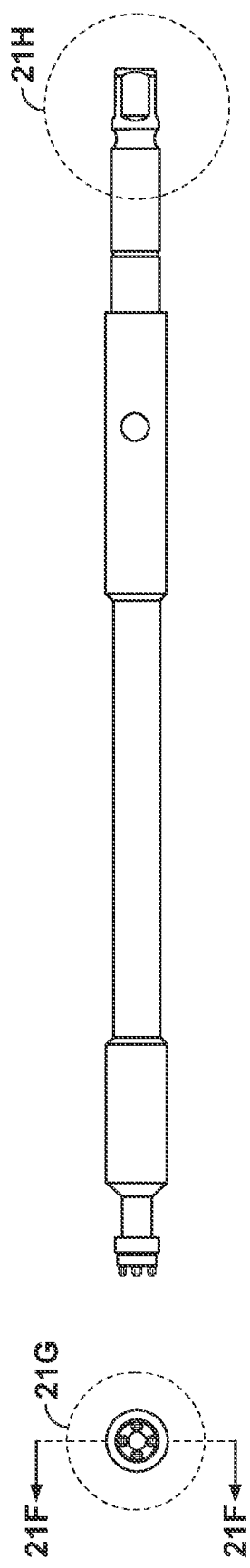
FIG. 21E
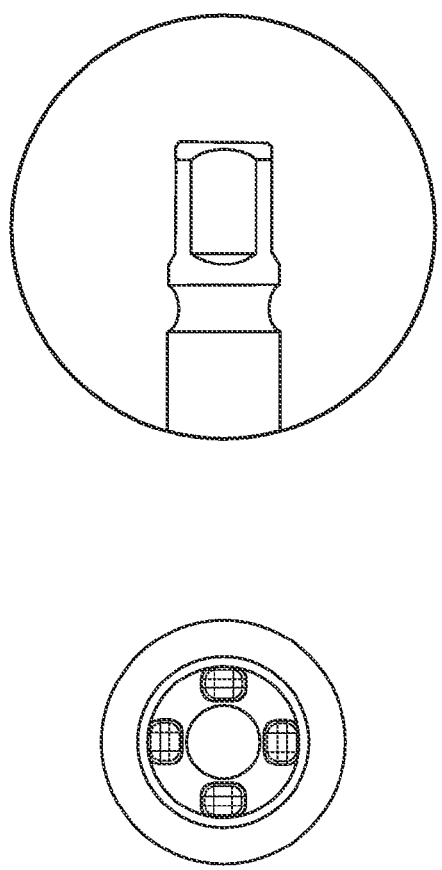
FIG. 21H
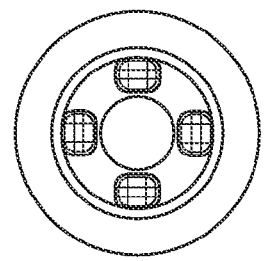
FIG. 21G
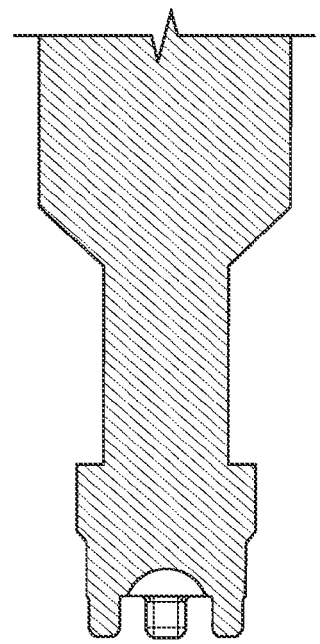
FIG. 21F
FIG. 21D

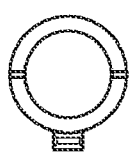
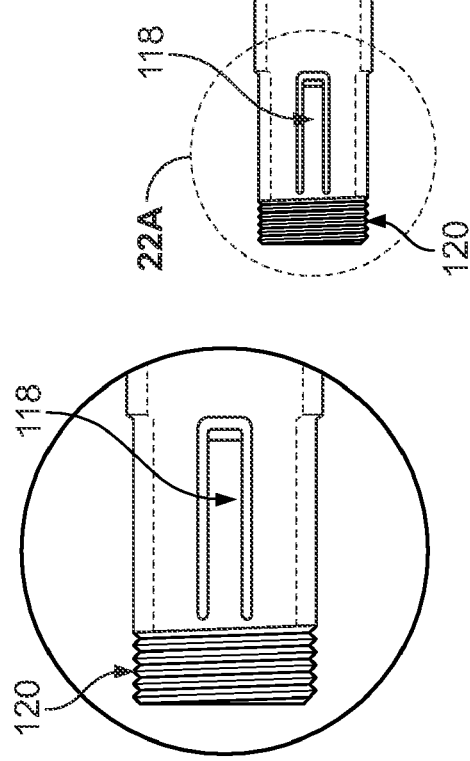
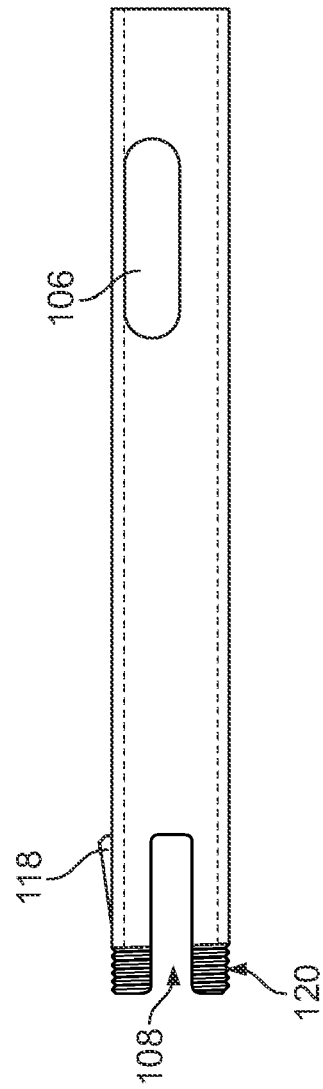
FIG. 22C
FIG. 22B
FIG. 22D
FIG. 22A

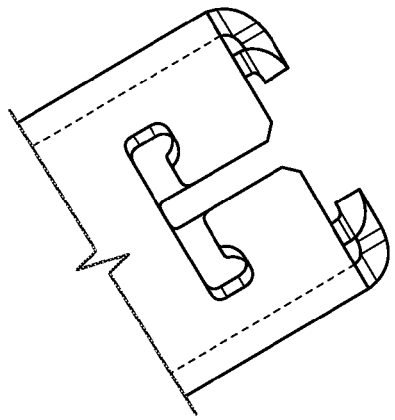
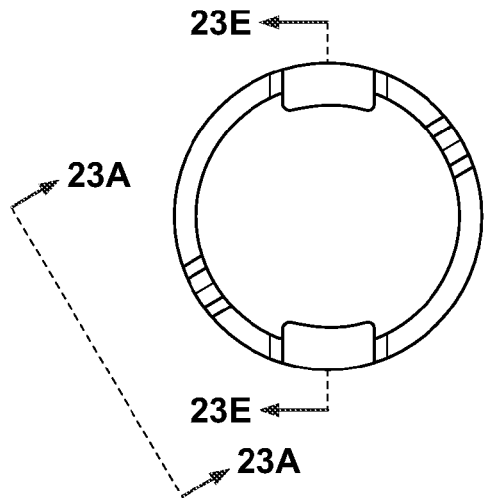
FIG. 23A    FIG. 23B
FIG. 23C
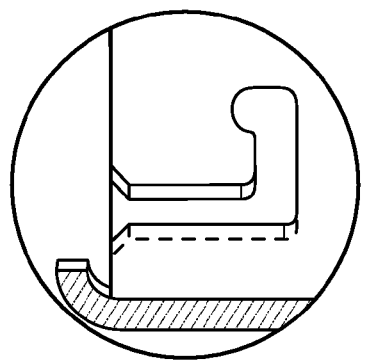
FIG. 23D
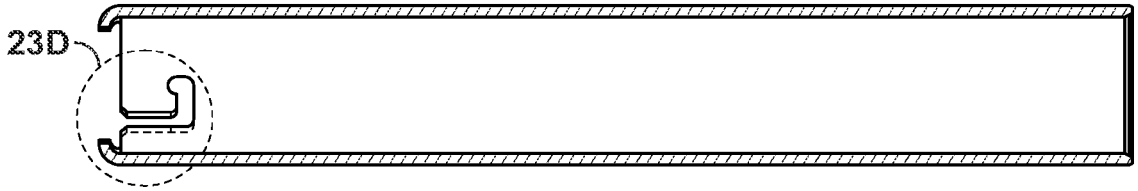
FIG. 23E

MINIMALLY INVASIVE SURGICAL SYSTEM

PRIORITY TO THE INVENTION

This application is a continuation of PCT application No. PCT/US06/006684, filed on Feb. 23, 2006, which claims priority to U.S. Provisional Application No. 60/655,983, filed Feb. 23, 2005 and U.S. Provisional Application No. 60/722,604, filed Sep. 29, 2005, the contents of which are hereby incorporated by reference herein in their entirety.

FIELD OF THE INVENTION

The invention relates generally to an apparatus and method for surgically implanting a fixation device, more particularly, to an apparatus and surgical method that secures bone or bone segments relative to one another with minimal invasion into the surrounding body tissue.

BACKGROUND OF THE INVENTION

Implant devices secured to bone or bone segments are utilized to promote the healing and repair of various parts of the human body. In some cases, the implant devices are secured to the bone or bone segments such that the bones themselves heal, fuse, or stabilize relative to one another. In other cases, implant or fixation devices are used to secure bones or bone fragments so that the surrounding soft tissue may heal without disruption by relative movement of the bones.

During the surgical procedure to implant the fixation devices, a plurality of bone screws or other fixation elements are secured to a plurality of respective bones. Then, each of the bone screws is secured relative to the others with an additional apparatus, such as a connecting member or brace.

For example, spinal rods that immobilize vertebral bones of the spinal column are typically anchored to the vertebrae via bone screws that extend through the pedicle into the vertebral bodies or by hooks that engage about the vertebrae. The spinal rods are connected to the screws or anchor members by coupling members, which may be yoke-shaped. Such coupling members may be integral with the anchor member head or separate components from the anchor member.

While incisions are required during such surgical procedures in order to gain access to the site where the implant is secured, such incisions can cause damage, injury, and trauma to the patient's body. To avoid causing unnecessary damage, it is preferable to make the incisions as small and few as possible.

One prior approach to implanting a bony structure stabilization device uses an installation instrument with a pivoting brace inserter. To implant the connecting element, extensions are attached to the anchors and the installation instrument with the pivoting brace inserter attached to the extensions. The pivoting brace inserter employs a fixed geometric relationship to guide the connecting element into position. The instrument mounts to the bone anchors and holds the connecting element such that when the instrument pivoting arm is pivoted, the connecting element swings into position. As the connecting element is swung into position, the element enters the body through the skin at a remote location removed from the surgical incisions made to attach the bone anchors to the bone.

This approach is problematic because another incision or opening is made through the skin, in addition to the openings required to insert the two screws. This additional opening allows for insertion of the brace or rod. Further, because of the fixed path, such a system is unable to direct the connecting element along a path of least resistance through the soft tissues and thereby causes tissue trauma that could otherwise be avoided by the surgeon variably moving the connecting element around and between these tissues.

Another approach to the minimally invasive system utilizes the same pathway that is used to insert the spinal anchors to also insert the connecting element. The connecting element is then manipulated such that it shifts to a perpendicular orientation to the insertion pathway in order to connect the anchors. Positioning of the connecting element can be assisted by a manipulation tool but nonetheless remains relatively unguided relying significantly on surgeon skill and patience.

Accordingly, there is a need for an MISS that limits the number and size of the incisions, minimizes trauma to the soft tissues, and also provides physicians with sufficient control to efficiently and effectively implant necessary devices.

SUMMARY OF THE INVENTION

In accordance with one aspect of the present invention, an MISS apparatus and method are disclosed that secure bone or bone fragments together. To this end, the apparatus and method utilize a plurality of bone anchors and a connecting rod. The bone anchors are fixed to the bone and the connecting member is secured to the bone anchors such that the bones are substantially fixed relatively to one another. To implant the anchors and connecting member, the system utilizes a number of tools or instruments that provide the surgeon with accurate and precise implant insertion, while limiting the number and extent of the incisions required. While the MISS can be used to secure various bones and bone fragments relative to one another, a pedicle screw assembly with a spinal rod is described herein as an example.

The preferred MISS implant includes at least two pedicle anchors or screws, yokes, closure caps, and a connecting member. In addition, in a preferred form, the system may include a dilation tool, docking sleeves, yoke manipulators, restraints that engage the yoke manipulators, a rod inserter, and optionally a guide. To begin the procedure, a surgeon percutaneously inserts a Jamshidi needle over the posterior spinal anatomy creating a small incision the Jamshidi holds the guidewire and is used to percutaneously force in the guidewire. A surgeon can determine through tactile feedback, where the implants and various tools should be inserted. The guidewire is driven to a predetermined depth into the target pedicle bone of the selected vertebral segment. After the guidewire is secured, the surrounding tissue is stretched using various dilation techniques. The surrounding tissue may also be incised to provide passage of the MISS tools. Subsequent to tissue dilation and/or incision a docking sleeve is inserted into the percutaneous opening.

The docking sleeve is the minimally invasive surgical portal through which the surgery is performed. In one form, the docking sleeve has docking fasteners such that the docking sleeve can be fixed to the bone during the surgical procedure. After the docking sleeve is secured in position, the surgeon can prepare the bone for receiving the anchor. A facing tool is sometimes used to resurface the bone to a more desired contour such as concave, dome, flat, or other beneficial shape. Before the anchor is inserted, an awl or other instrument can be used to create a depression or opening on the bone surface at the location where the anchor will be set. To aid the surgeon in attaching the anchors, yoke manipulators are employed to assist in the insertion. The yoke manipulators, anchors, and restraint are advanced down the docking sleeve with a screw driver that rotates the anchor into position on the pedicle bone. At this point the docking sleeve may be removed.

Before insertion of the connecting member, the surgeon must repeat the procedure and insert the other bone anchor(s). After the bone anchors are inserted, the yoke manipulators remain attached to the anchors to facilitate insertion of the connecting member. At least one of the yoke manipulators includes slots on each side that allow for the passage of connecting member. Another yoke manipulator has at least one slot allowing for insertion of the connecting member. The connecting member is fed between the yoke manipulators by a rod inserter. Therefore, the yoke manipulators allow for the connecting member to be inserted into position without requiring another opening or incision into the body than the openings used to attach the anchors. After the connecting member is positioned in the anchor yokes, a closure cap is inserted into the yoke and rotated such that the connecting member is fixedly secured into position. The yoke manipulators may now be removed from the bone anchors along with any other tools and instruments such as the docking sleeve. After removal of the tools, the surgeon closes the wound. The MISS allows for insertion of an implant with out unnecessary trauma to the body and more particularly to the surrounding tissue. Further, the system provides the surgeon with guidance during the procedure without being unduly rigid.

Therefore, a minimally invasive surgery system (MISS), described herein, is used to implant bone fixation devices. An MISS system is particularly useful during spinal and neurosurgical procedures because the surgeon must have access to location deep within the body and such access requires the surgeon to reposition or avoid vital tissues.

An MISS is useful for performing a spinal surgery, but can be effectively used for non-spinal applications in humans and other mammals. The implants described herein are preferred models, however, this minimally invasive instrumentation may be used with a variety of implant forms, spinal and non-spinal, in many cases with minimal or no modification. For example, the docking sleeve described herein may be used for repairs of the hip as well as for repairs of the spine. It may be used to implant bone screws, fusion devices, and many other prosthetic and non-prosthetic implants, or to perform non-implant repair.

The disclosed MISS accommodates both cannulated and non-cannulated implant placement. This allows the system to be tailored to a particular surgeon's preferences. For example, when employing a guidewire, a cannulated pedicle bone screw along with cannulated tools are utilized. However, many surgeons find cannulated instruments to be less effective due to the movement constraints resulting from the presence of the guidewire. Therefore, surgeons can tailor the system to accommodate their preferences for guidewire use.

BRIEF DESCRIPTION OF THE DRAWINGS

FIG. 16 A is a side view of the obturator of FIG. 16;
FIG. 16 B is another side view of the obturator of FIG. 16;
FIG. 16 C is a cross section of the obturator of FIG. 16B along line C-C.
FIG. 16 D include various plan views of portions of the obturator of FIG. 16;
FIG. 17 A is a top plan view of the docking sleeve of FIG. 17;
FIG. 17 B is a front view of the docking sleeve of FIG. 17;
FIG. 17 C is a side view of the docking sleeve of FIG. 17;
FIG. 17 D is a cross section of the docking sleeve of FIG. 17;
FIG. 17 E is a side view of a portion of the docking sleeve of FIG. 17;
FIG. 17 F is an end view of the docking sleeve of FIG. 17;
FIG. 17 G is a magnified view of a portion of the docking sleeve of FIG. 17;
FIG. 17 H is a side view of a retainer;
FIG. 17 I is a cross section of a the retainer of FIG. 17J;
FIG. 19 A is a side view of the facing tool of FIG. 19;
FIG. 19 B is a top view of the facing tool of FIG. 19;
FIG. 19 C is a side view of the facing tool of FIG. 19;
FIG. 19 D is a magnified view of a portion of FIG. 19 C;
FIG. 19 E is a cross section view of a facing tool of FIG. 19;
FIG. 19 F is a side view of a portion of the facing tool of FIG. 19;
FIG. 19 G is a top plan view of a portion of the facing tool of FIG. 19 F;
FIG. 21 A is a side view of a screw driver of FIG. 21;
FIG. 21 B is a cross section view along line A-A of a portion of the screw driver of FIG. 21;
FIG. 21 C is a top view of a portion of the screw driver of FIG. 21;
FIG. 21 D is a top plan view of the screw driver of FIG. 21D;
FIG. 21 E is a side view of the screw driver of FIG. 21;
FIG. 21 F is a cross section view of a portion of the screw driver of FIG. 21;
FIG. 21 G is a bottom plan view of the screw driver of FIG. 21;
FIG. 21 H is a side view of a portion of the screw driver of FIG. 21.

FIG. 22 A is a side view of a portion of the yoke manipulator of FIG. 22;

FIG. 22 B is a side view of the yoke manipulator of FIG. 22;

FIG. 22 C is a top plan view of the yoke manipulator of FIG. 22;

FIG. 22 D is another side view of the yoke manipulator of FIG. 22;

FIGS. 23 A-23G are various view of the restraint of FIG. 23;

FIG. 44 B is another perspective view of a cap inserter;

DETAILED DESCRIPTION OF THE PREFERRED EMBODIMENTS

Figure 1:
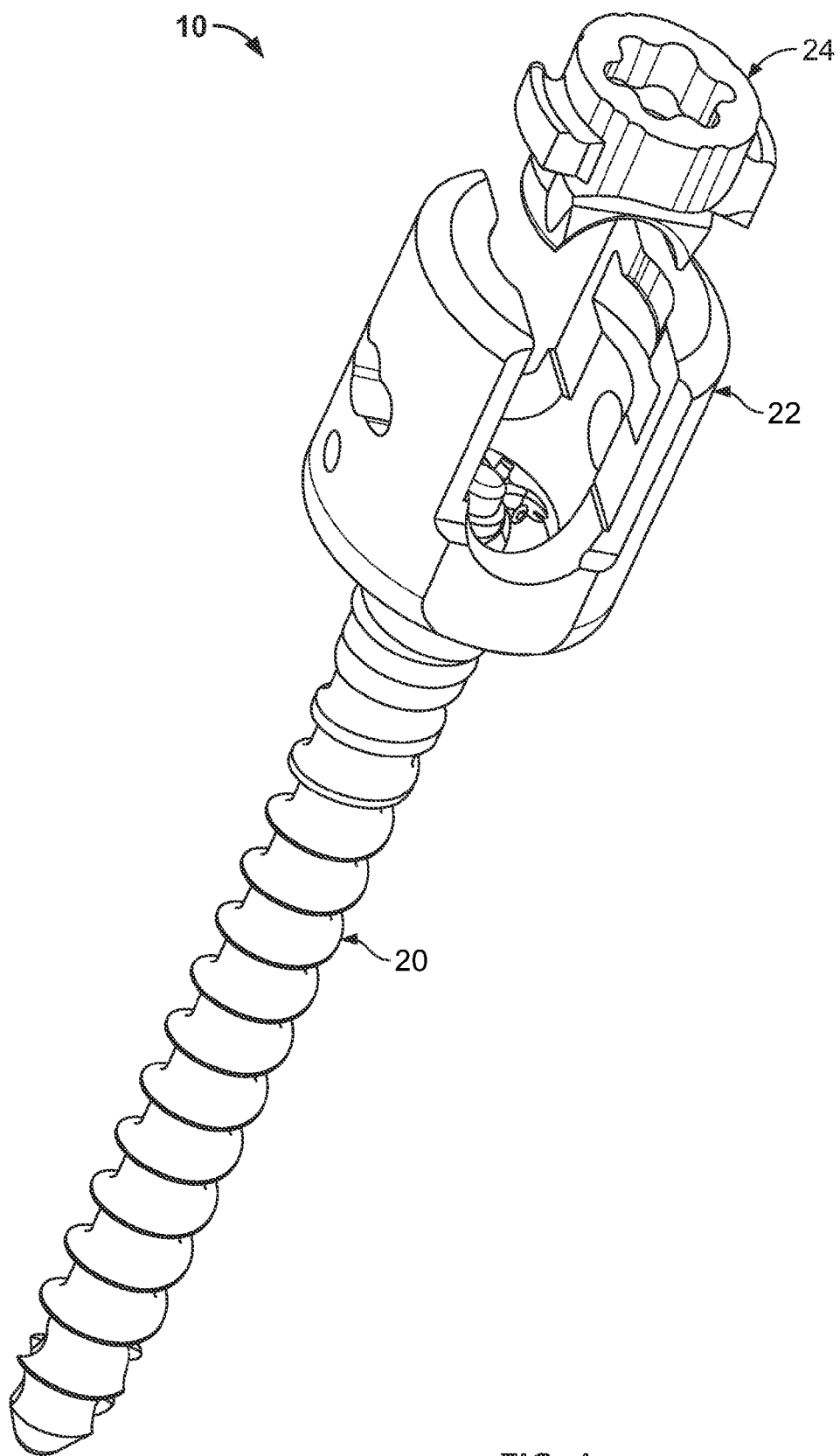
FIG. 1 is a perspective view of a bone anchor, yoke, and closure cap.
Figure 2:
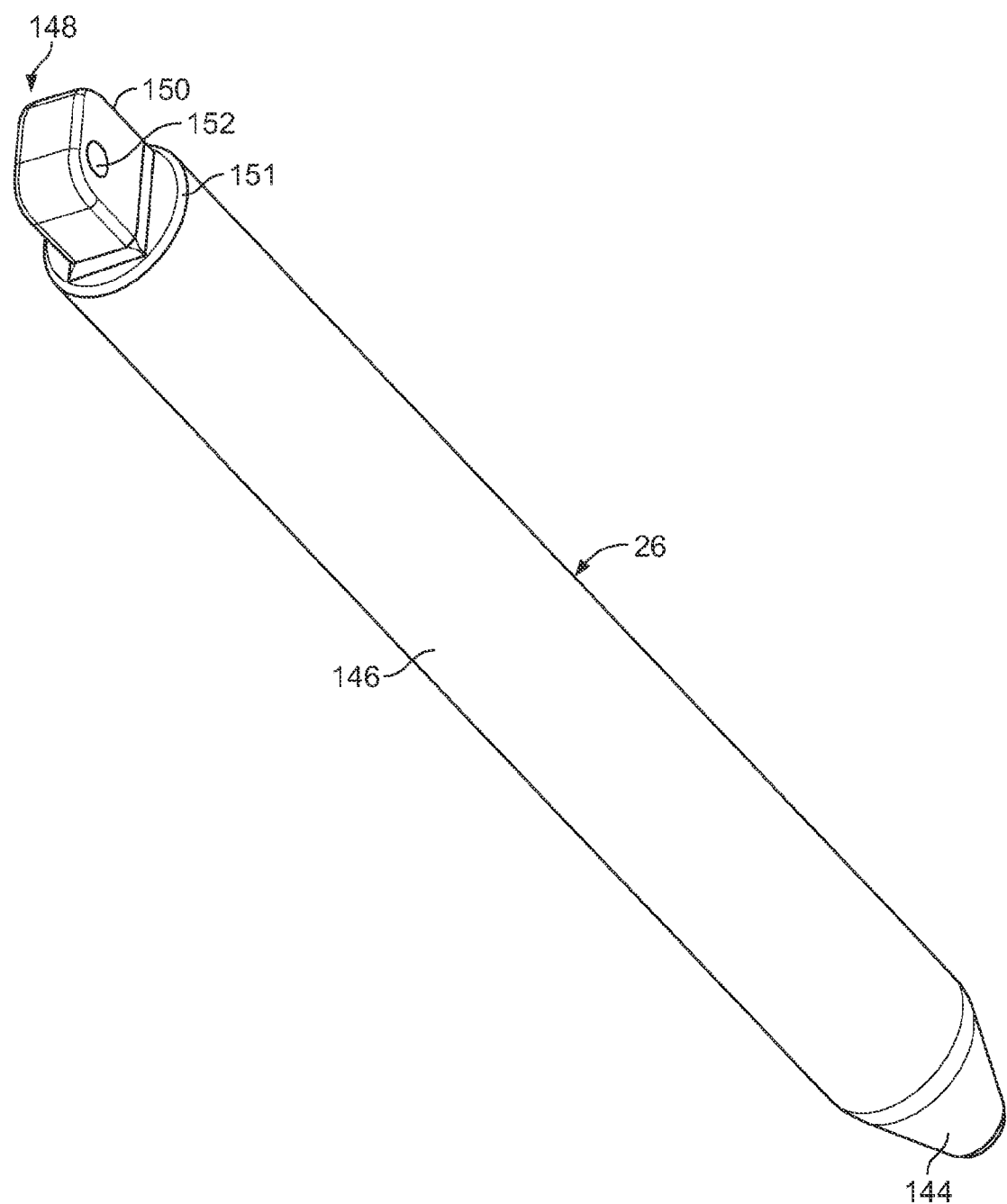
FIG. 2 is a perspective view of an MISS connecting member.
Figure 3:
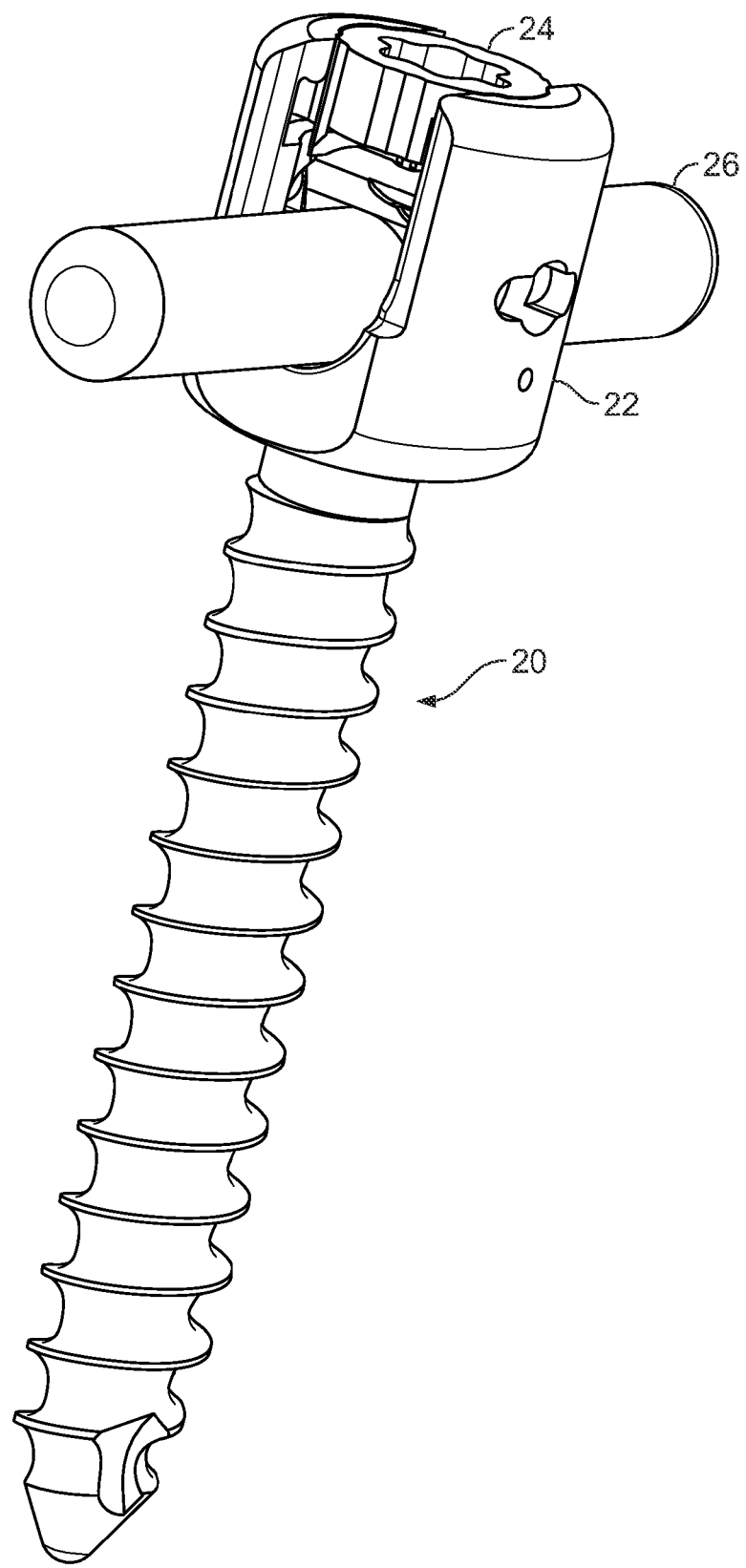
FIG. 3 is a perspective view of a portion of a connecting rod, a bone anchor, a yoke, and a closure cap.
Figure 4:
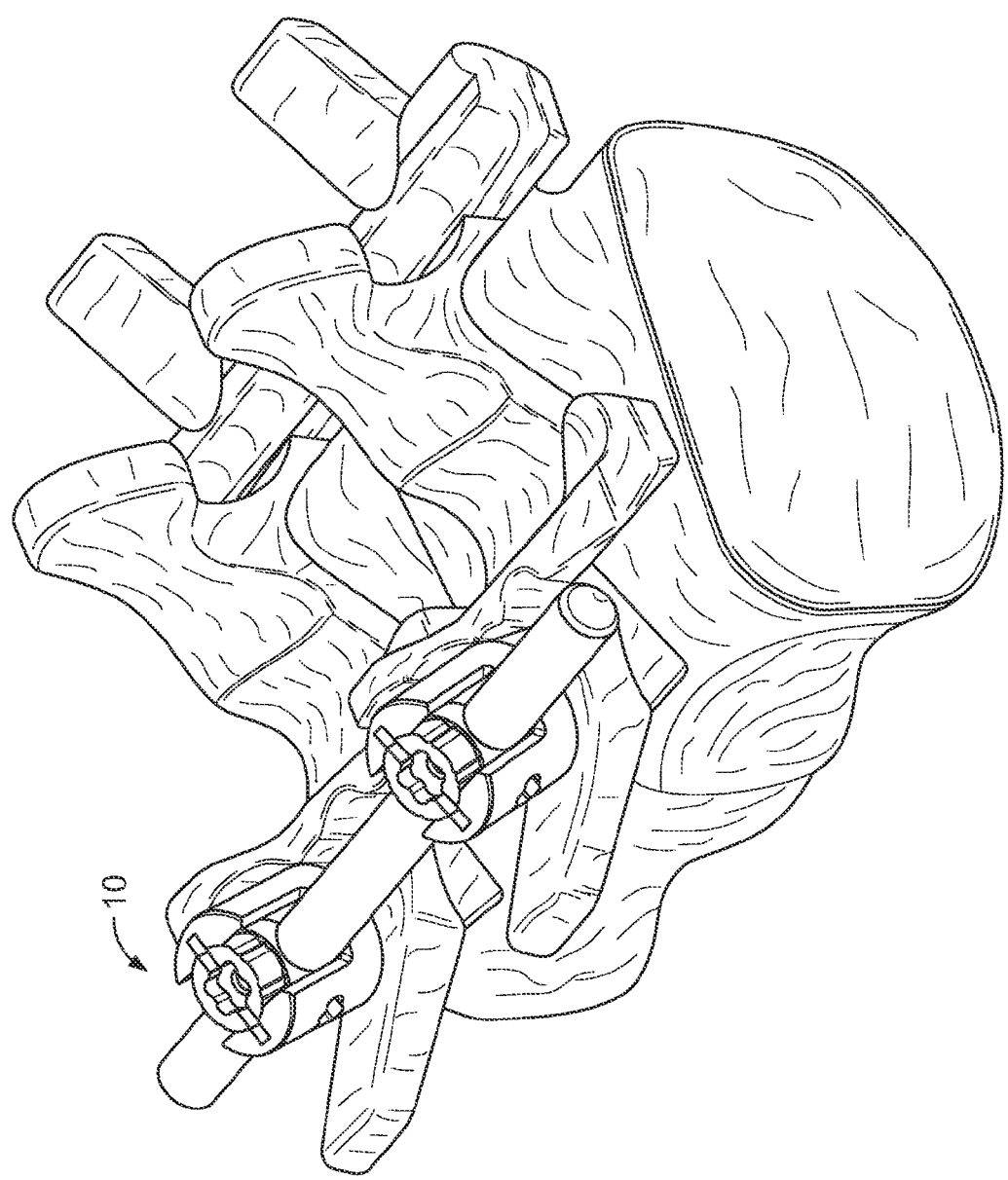
FIG. 4 is a perspective view of an MISS implant.

In the preferred embodiment, the MISS is utilized to implant a fixation device. In FIG. 1, the device 10 is shown as including a bone anchor or screw 20, a yoke 22 and a closure cap 24. While the cap 24 is preferably non-threaded, a threaded embodiment is also contemplated. The cap 24 locks into the anchor yoke 22 such that a spinal rod or connecting member 26 is fixedly held into position. The connecting member 26 is illustrated in FIG. 2. FIG. 3 shows a portion of a connecting rod 26 seated into the yoke 22. One embodiment of the implant, illustrated in FIG. 4, includes two anchors, and a connecting rod 26. For example, a similar system is disclosed in applicants' assignee's co-pending application PCT/US2004/003605 and U.S. patent application Ser. No. 10/973,659. Both of which are hereby incorporated in their entirety. Since the bone anchor 20, yoke 22, closure cap 24, and connecting member 26 are implanted into the body it is preferably that they be constructed of biocompatible material.

Figure 5:
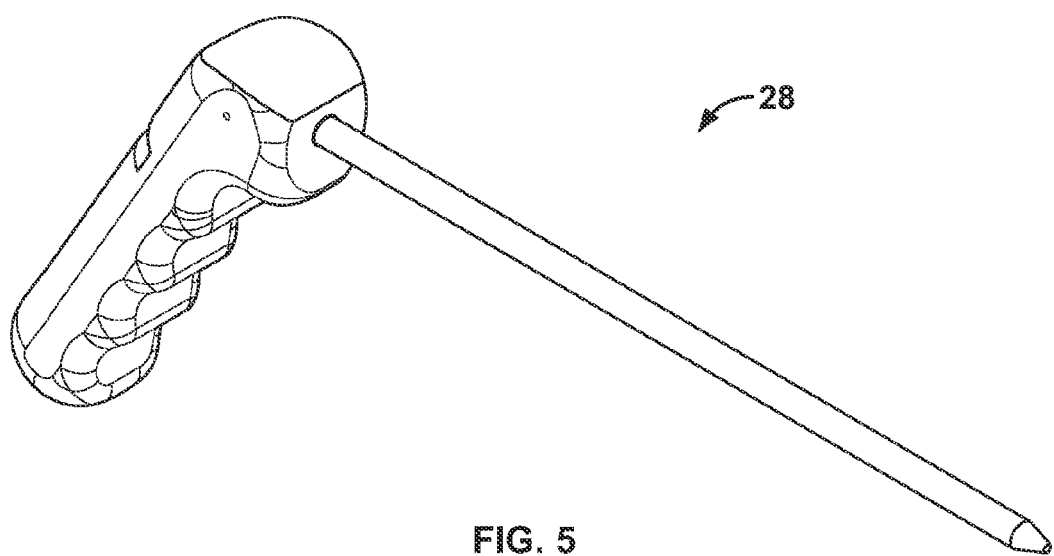
FIG. 5 is a perspective view of a Jamshidi needle without a guidewire inserted therein.
Figure 6:
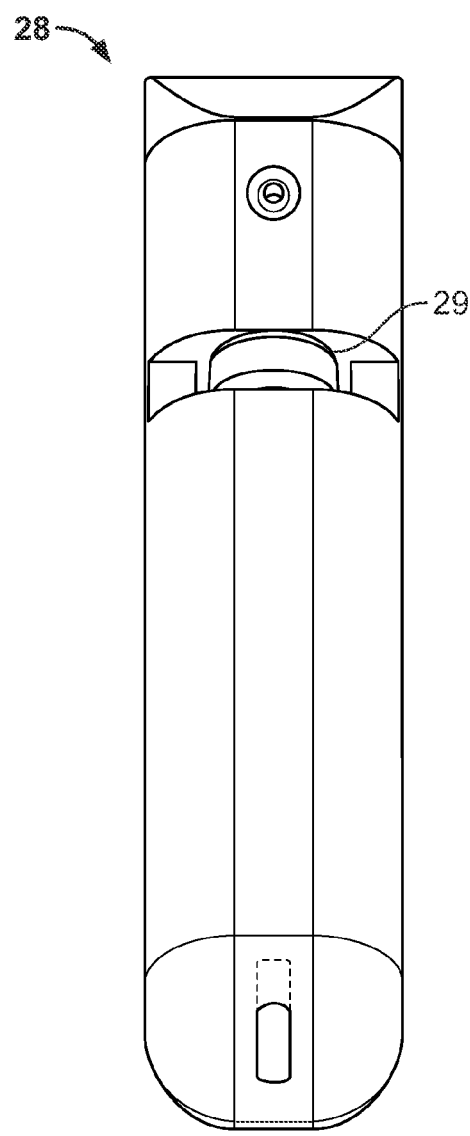
FIG. 6 is a rear plan view of the handle of the Jamshidi needle of FIG. 4.
Figure 7:
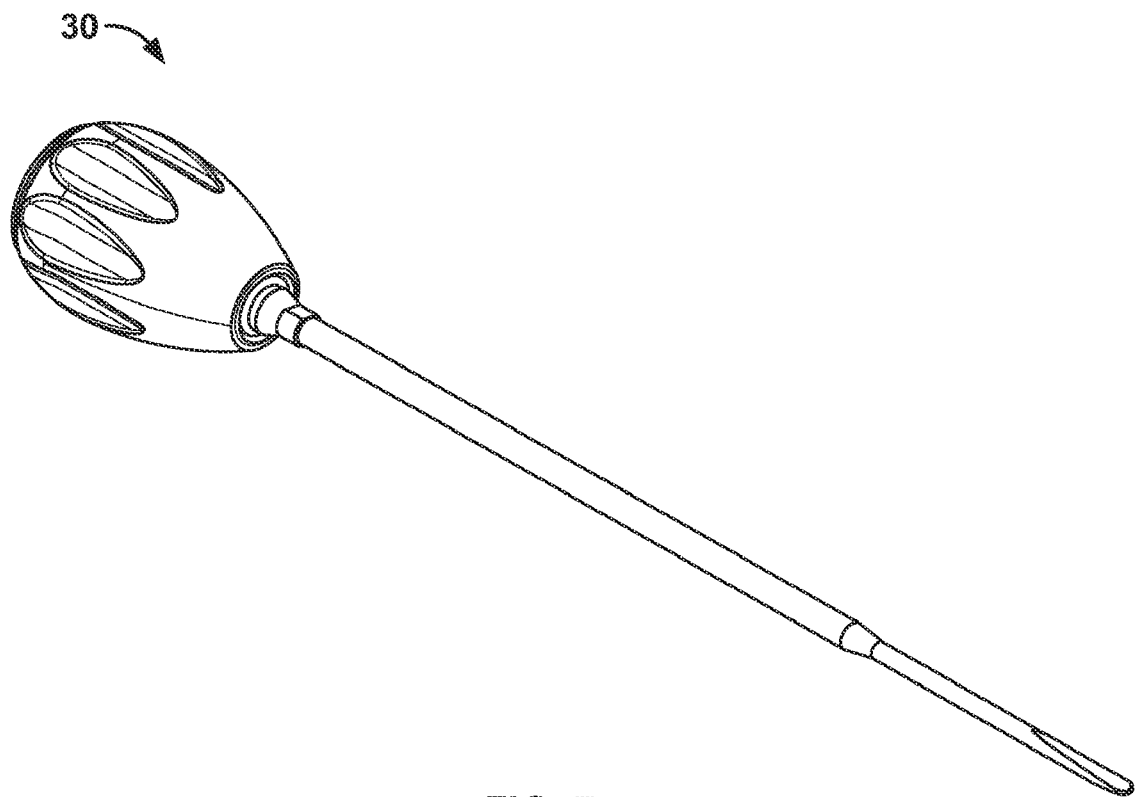
FIG. 7 is a perspective view of a pedicle finder.
Figure 8:
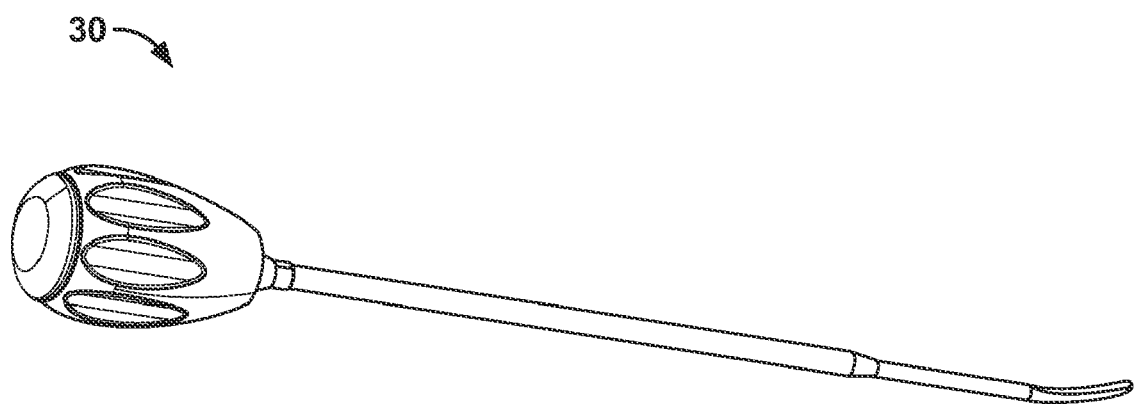
FIG. 8 is a perspective view of a pedicle finder having a curved insertion end.

Starting with proper implant placement is generally necessary for a successful procedure. The surgeon needs to identify the pedicle anatomy to determine anchor 20 placement. To begin, a surgeon may percutaneously insert a Jamshidi needle 28 over the posterior spinal anatomy. FIG. 5 illustrates the Jamshidi needle 28. The Jamshidi needle 28 is typically coupled with a guidewire 32. The handle of the Jamshidi needle 28 includes a clickwheel 29. The clickwheel 29, as shown in FIG. 6, is turned until the guidewire 32 is held firmly into position. After the needle 28 and guidewire 32 are coupled together, the assembly is then advanced into the patient. Guidance radio-imagery may be used. Gaining access using the needle 28 provides the surgeon tactile feedback regarding boney landmarks. At this time, a surgeon may also employ a pedicle finder 30, shown in FIGS. 7 and 8, to help identify the spinal anatomy. Alternatively, if the guidewire 32 was not inserted with the Jamshidi needle 28, it can be entered into the surgical site after the needle.

After entering through the skin, the guidewire 32 is then driven to a predetermined depth until secure. Wherever the guidewire 32 placed is typically the general target location for one of the bone anchors 20. Throughout the procedure, a fluoroscopic or other imaging device may be used to assure accurate placement of the guidewire 32, implant, and/or other tools. Using such an imaging tool, prevents placing the tools incorrectly or driving the instruments or implants in the wrong location, or too deeply into the body tissue as this could harm vital body tissue such as vascular or nerve tissue.

The guidewire 32 is preferred to have a self-cutting and self-tapping thread, however, the thread type and insertion means vary by surgeon preference. Alternatively, the guidewire 32 may have a non-threaded sharpened end for advancement through soft tissue and piercing the bone. Such a guidewire 32 is preferably constructed of biocompatible metals or alloys such as stainless steel, titanium, or nitinol.

Once the guidewire 32 has been positioned at the surgical site, the surrounding tissue may be stretched and/or incised to provide passage of additional MISS tools. To stretch the tissue, a number of series dilators 33 or open ended sleeves, can be slid down the guidewire 32 one on top of another. As shown in FIGS. 11 A-11 H, the series dilators 33 are tubes with one end having a sloped nose 35 to allow for easy insertion into the tissue. Each dilator expands slightly in diameter and thereby expands the tissue as the dilator is slid down the guidewire 32 into the surgical site. After the series dilators have sufficiently stretched the tissue, a docking sleeve 34 may be slid down the series dilators. The docking sleeve 34, discussed in more detail below, provides a window to the surgical site. The docking sleeve 34 may be slid down a dilator with a slightly smaller diameter than the docking sleeve 34.

Figure 12:
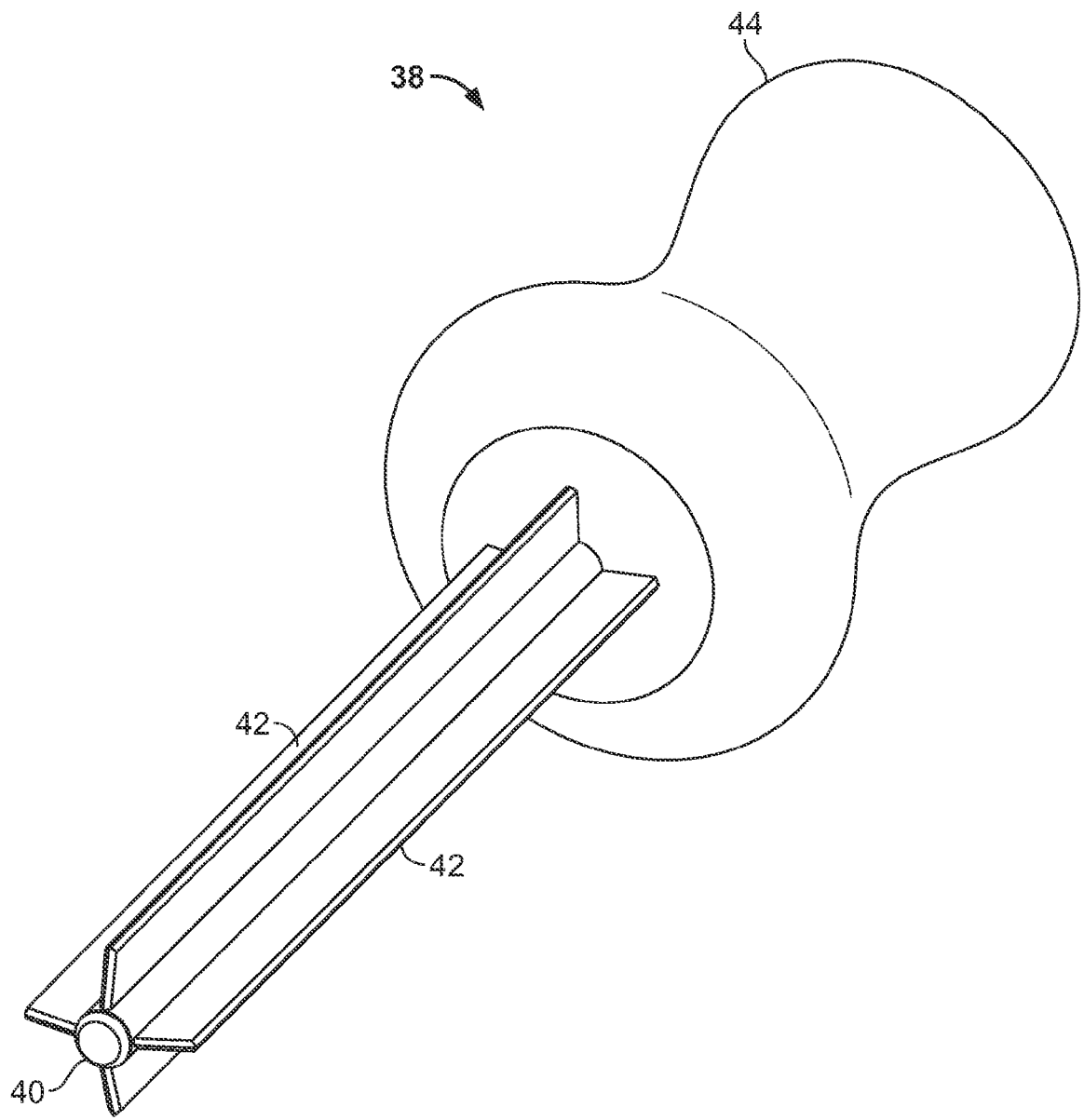
FIG. 12 is a perspective view of a cannulated cutting instrument.

Alternatively, the surgeon could use a scalpel or another cutting instrument such as the cannulated cutting tool 38 of FIG. 12 to incise the tissue along a path generally following the guidewire to gain increased access to the surgical site. The cannulated cutting tool 38 may have a tube or guide portion 40, a plurality of fin portions 42 that may be used to precisely create an opening of the tissue, and a handle portion 44.

Figure 13:
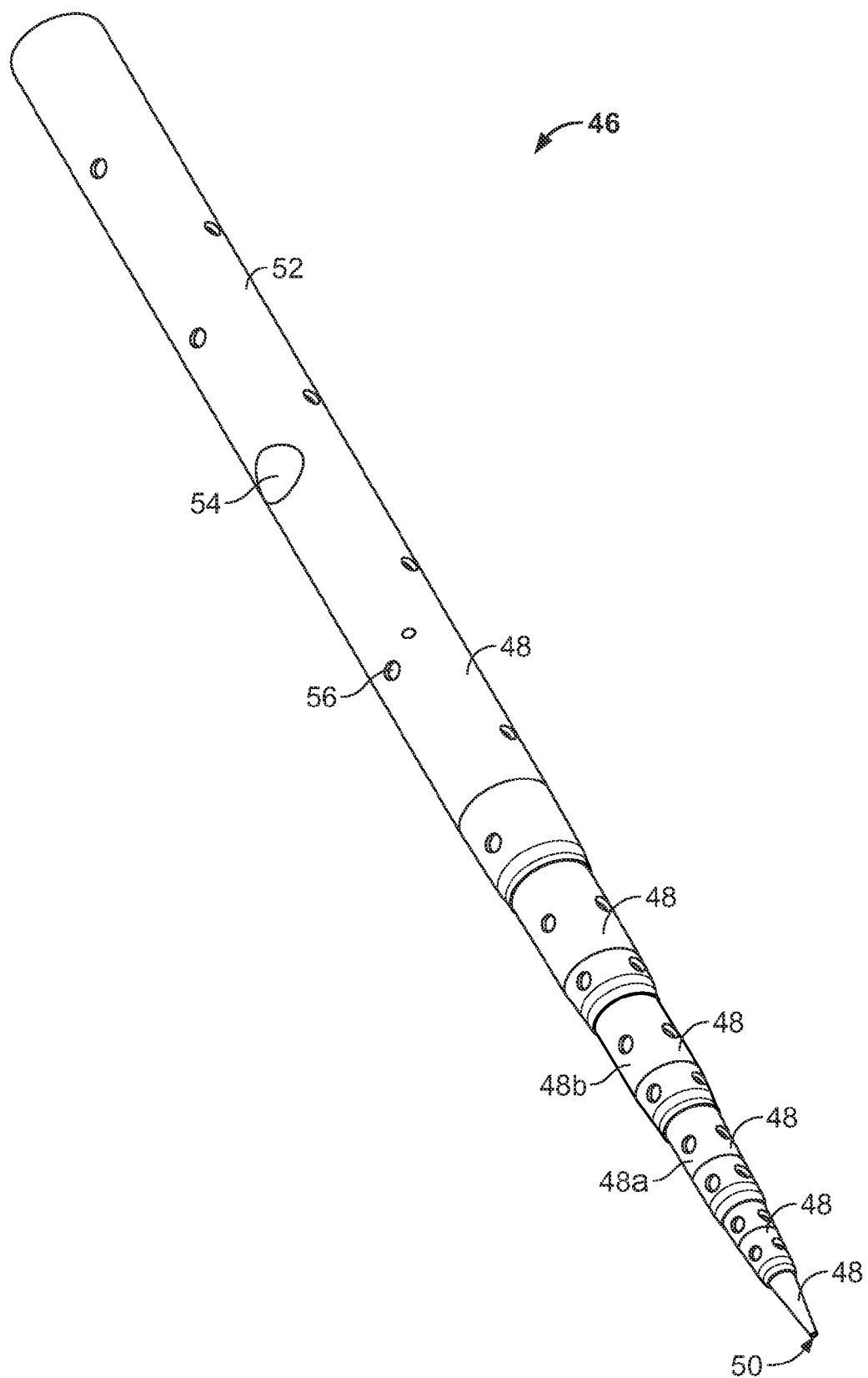
FIG. 13 is a perspective view of a harpoon dilator in an extended configuration.

Various other dilation tools may also be employed. For example instead of the series dilators, a surgeon may use a harpoon dilator 46, shown in FIGS. 13, 14, and 15. The harpoon dilator 46 is spring biased to a fully extended position shown in FIG. 13. The harpoon dilator 46 comprises a series of progressively larger spring loaded interdependent cylinder portions 48. Each interdependent cylinder 48 is preferably biased away from the next cylinder by a series of springs. Such springs have a progressively higher spring constant as the diameter of the independent cylinder portions 48 increases. The dilator 46 may further include a reduced diameter nose 50 that is cannulated to allow for passage of the guidewire 32.

Figure 14:
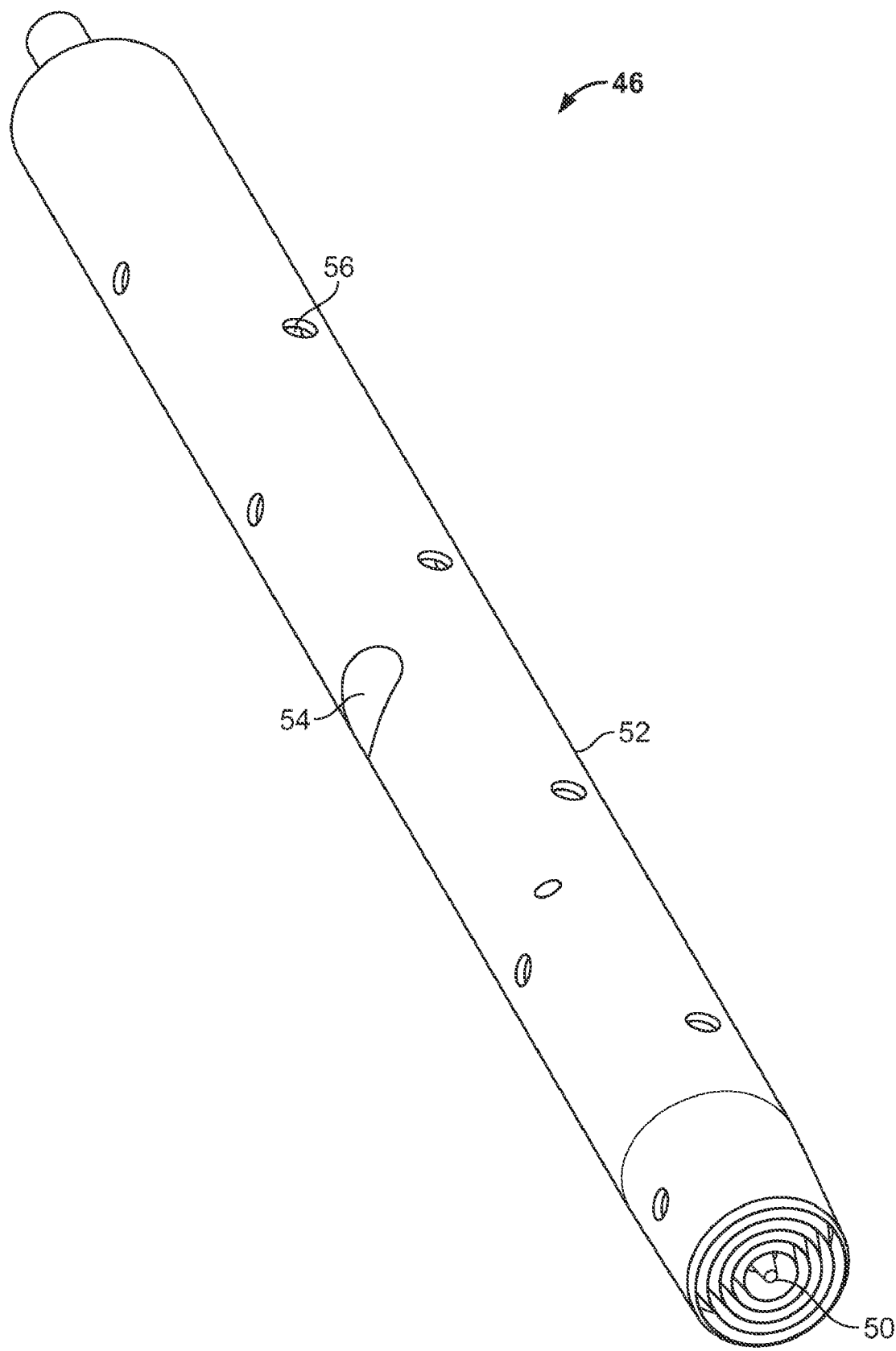
FIG. 14 is a perspective view of a harpoon dilator in a collapsed configuration.
Figure 15:
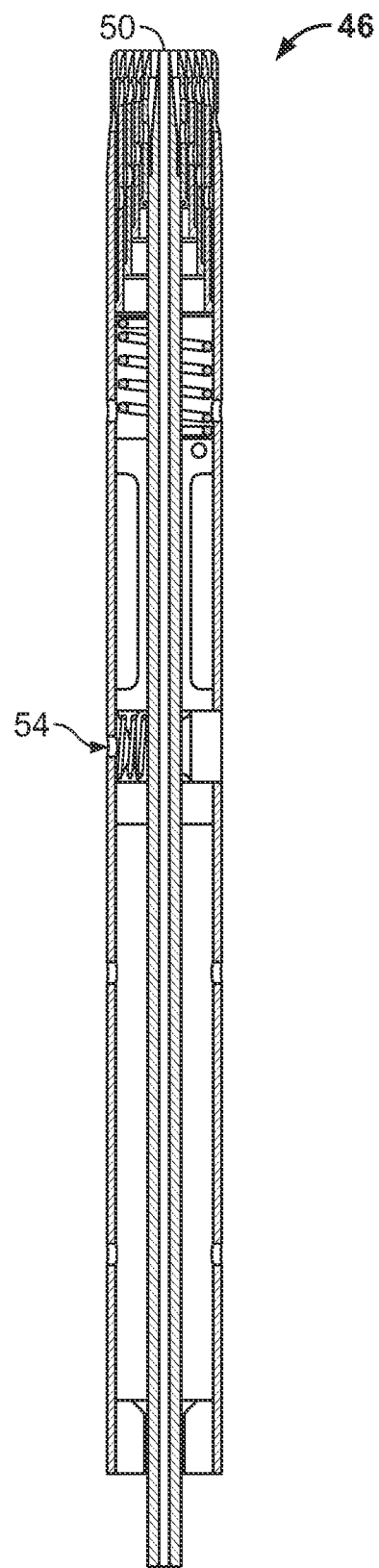
FIG. 15 is a cross sectional view of the harpoon dilator of FIG. 14.

The harpoon dilator 46 is placed over the guidewire 32 by placing the end of the guidewire 32 into the cannulated nose 50. The dilator 46 may then be slid down the guidewire 32 until the nose 50 contacts the bone surface. The surgeon then drives the extended dilator toward the bone, progressively dilating the soft tissue by pushing a smaller diameter cylinder 48*a* into an adjacent, larger diameter cylinder 48*b*. When the final cylinder 52, which is also the largest, has been pushed into contact with the surrounding soft tissue and contacts or closely approximates the bone, the surrounding tissue has been stretched to the diameter of the largest cylinder 52. When the harpoon dilator has been fully collapsed it automatically locks into this configuration as shown in FIGS. 14 and 15. To extend the harpoon dilator to its original configuration, a release button 54 may be engaged.

The harpoon dilator 46 can be removed from the system either in the collapsed or extended position by sliding it back off the guidewire 32. While the harpoon dilator 46 can be used alone, it may also be sized to cooperate with the docking sleeve 34 or the yoke manipulator assembly 141 to assist the introduction of these tools into the soft tissue. In addition, the harpoon dilator 46 could be configured to stretch the tissue without the assistance of the guidewire 32. The dilator 46 may include cleansing holes 56 for instrument sanitation.

Figure 16:
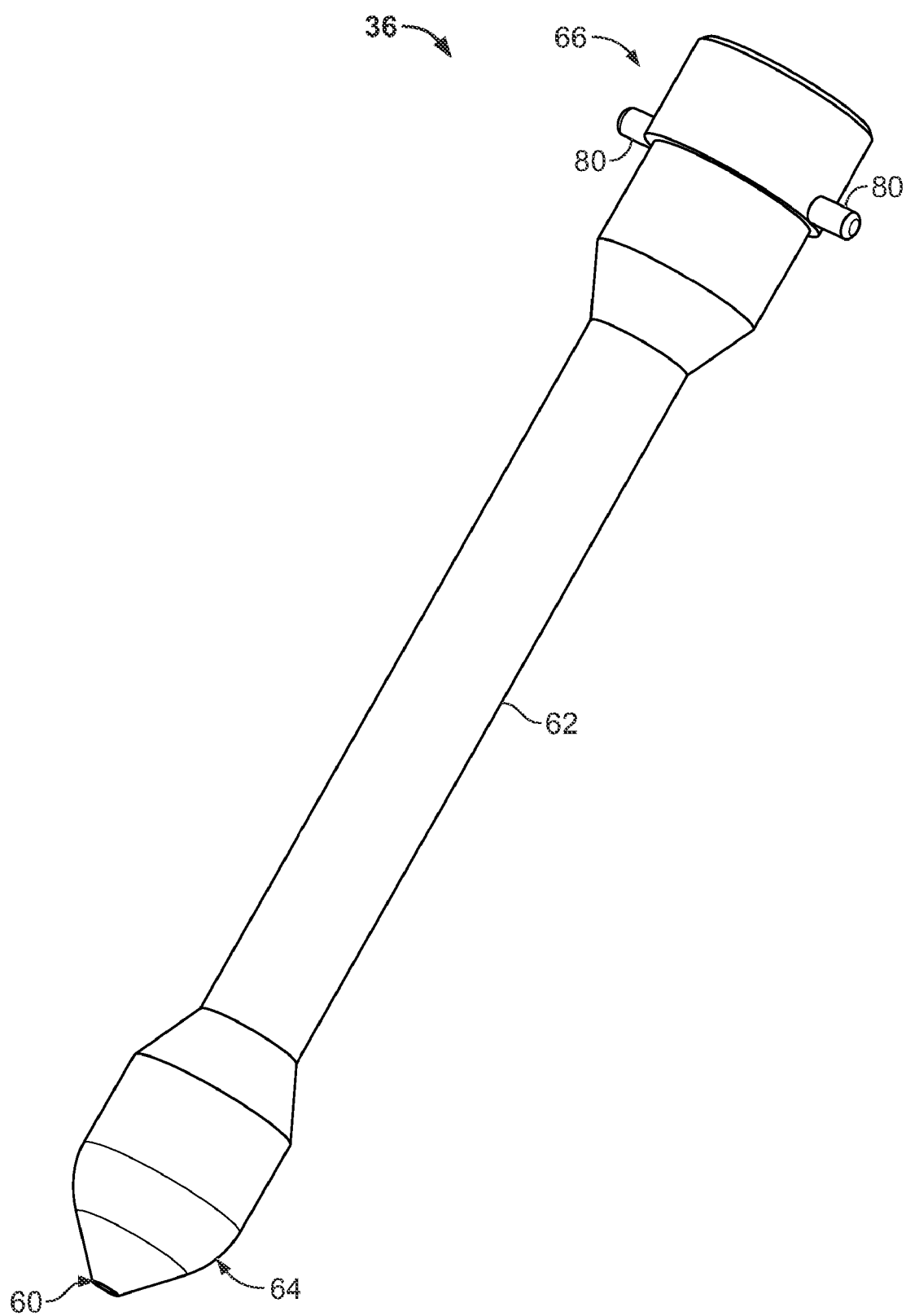
FIG. 16 is a perspective view of an obturator.
Figure 16A:
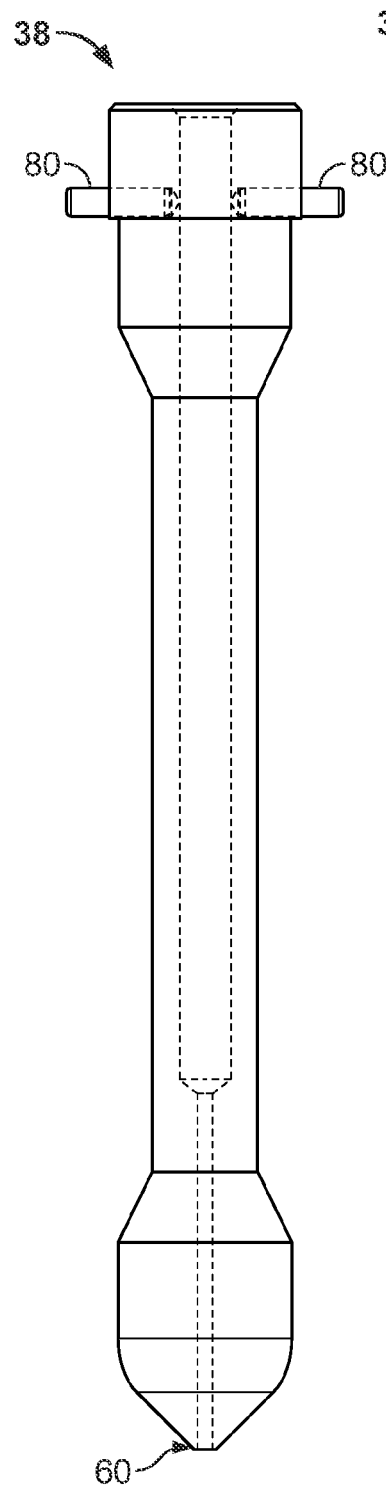
Figure 16B:
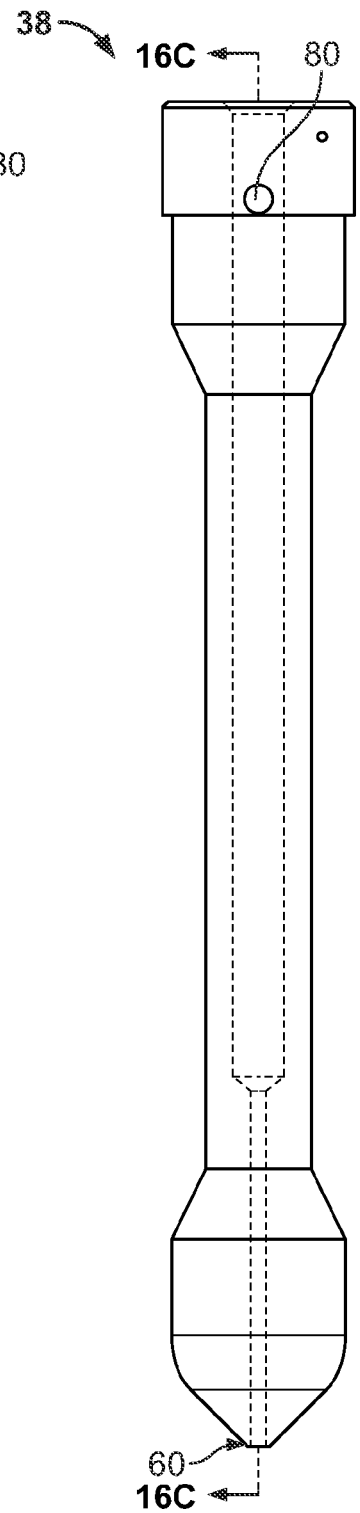
Figure 16C:
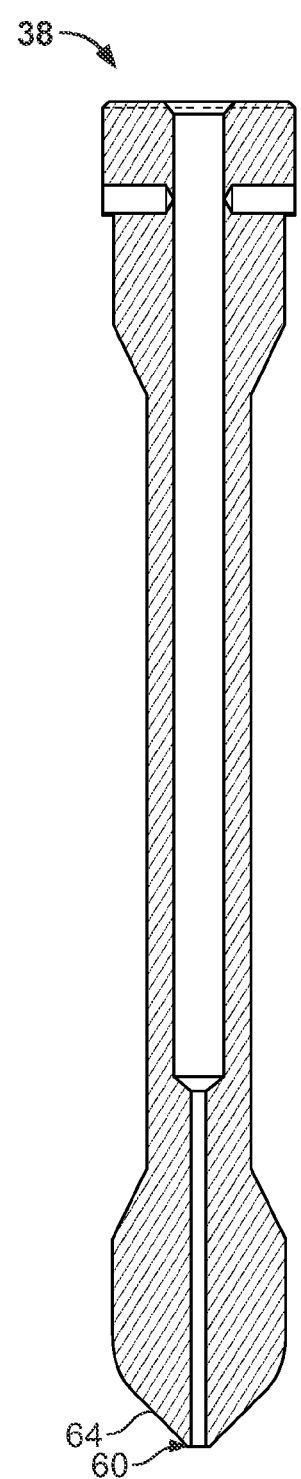
Figure 16D:
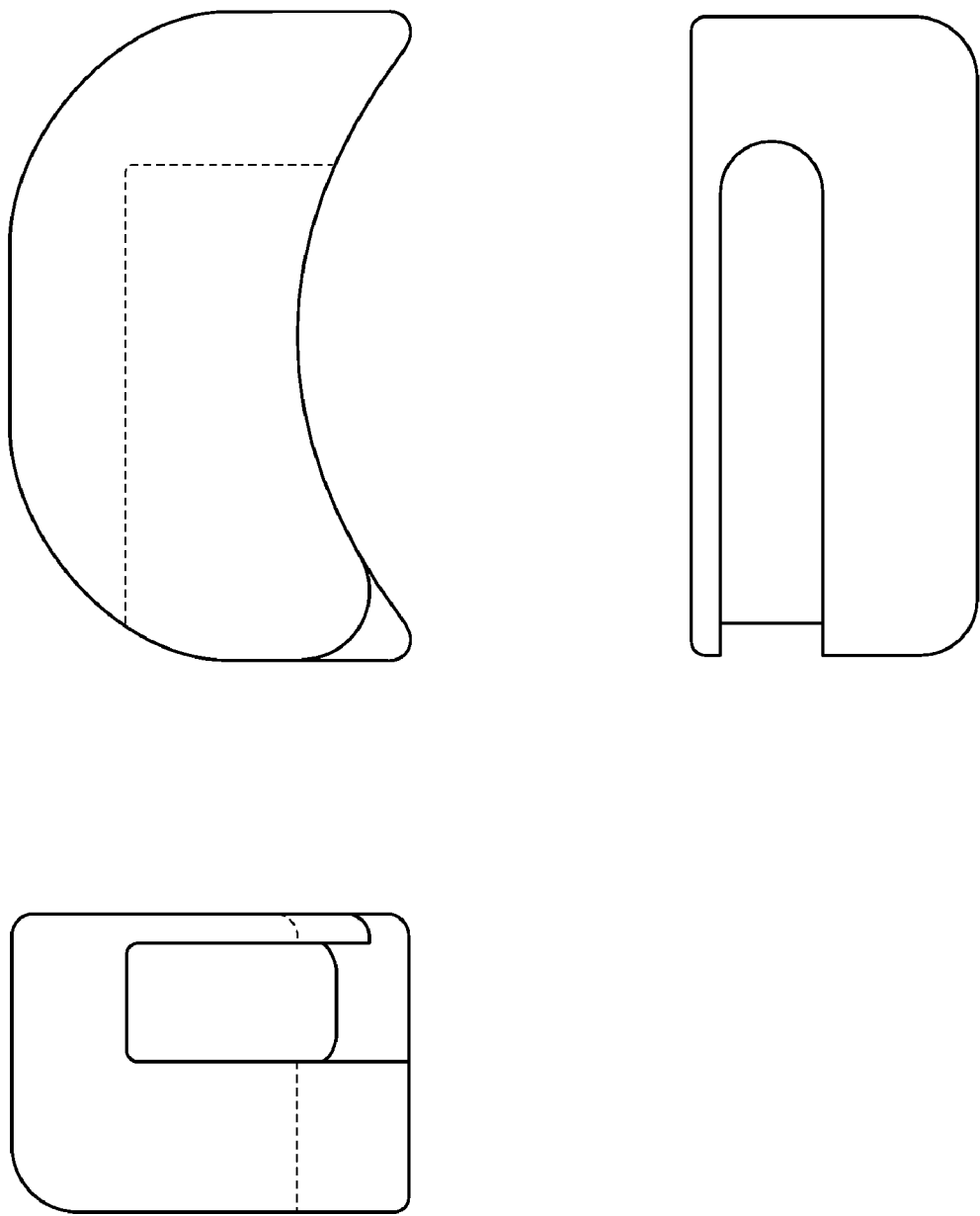
Figure 17B:
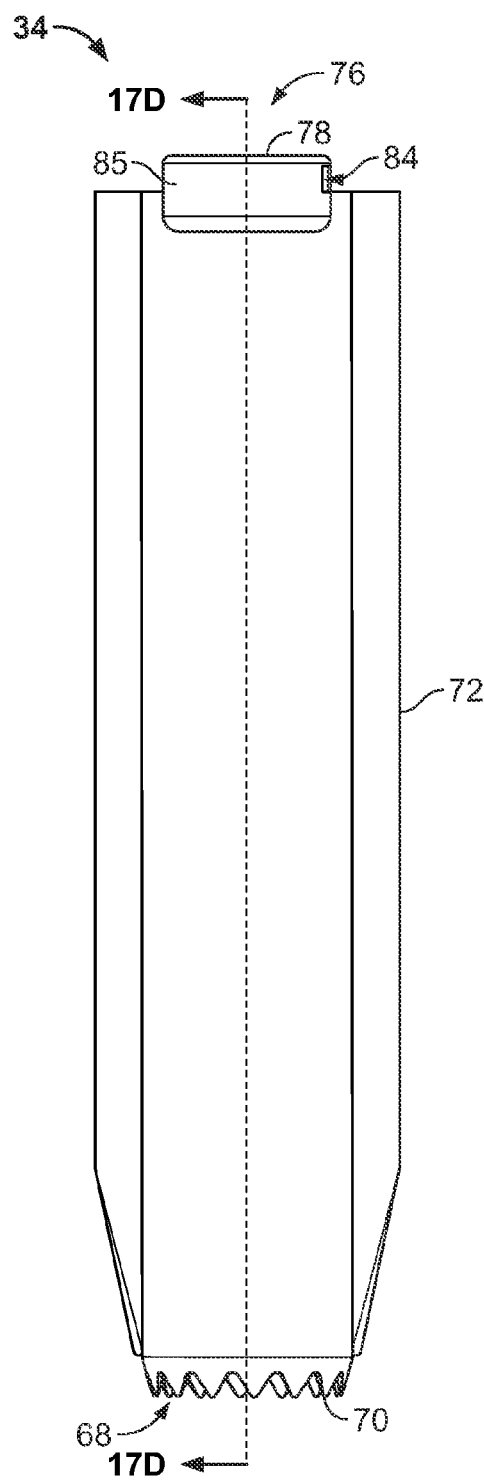
FIG. 17 is a perspective view of a docking sleeve.
Figure 17C:
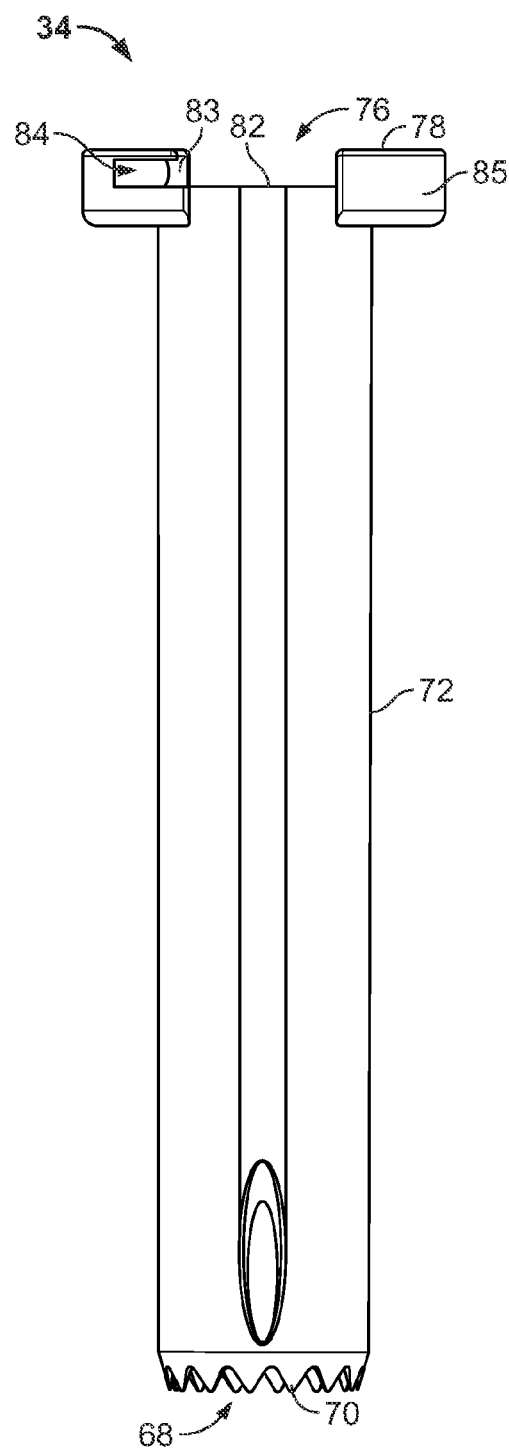
Figure 17D:
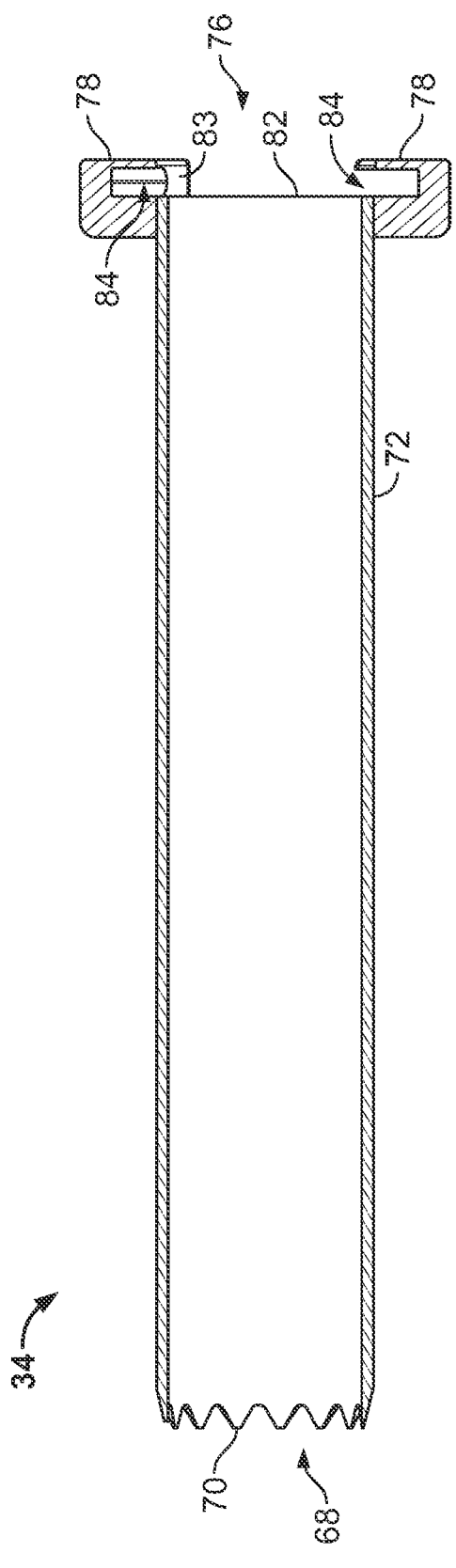
Figure 17E:
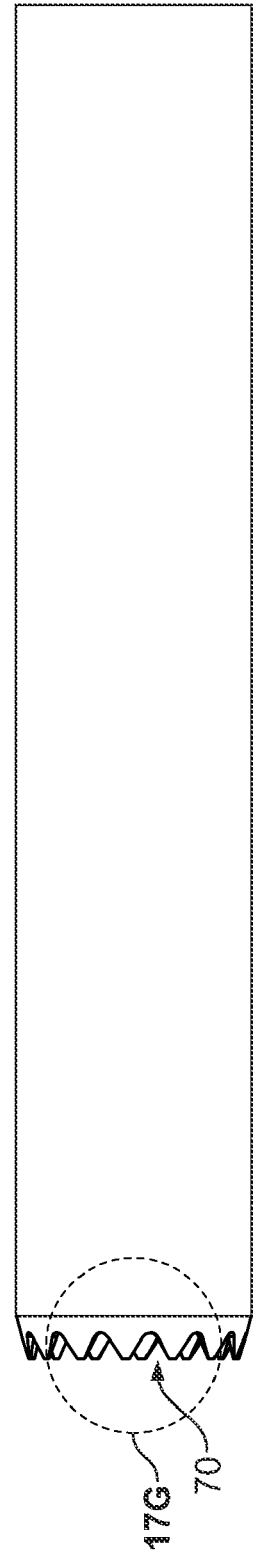

A single obturator 36, shown in FIG. 16, or set of obturators 36 may also be used to dilate the tissue surrounding the surgical site. The obturators 36 may be used in conjunction with or instead of incising the tissue along the guidewire 32. When a set of obturators 36 is employed, the surgeon uses obturators 36 with progressively larger diameters. By using the cannulated opening 58 in the obturators 36, the tool is advanced down the guidewire 32. After the obturator 36 has been advanced down the guidewire 32 and the tissue stretched, the first obturator 36 may be removed and another larger obturator 36 then inserted. Utilizing such tools stretches the surrounding tissue to accommodate the obturator's increasing size. This process continues until the surgeon has employed an obturator 36 with a sufficiently large enough diameter to create sufficient stretching of the surrounding tissue.

Figure 9:
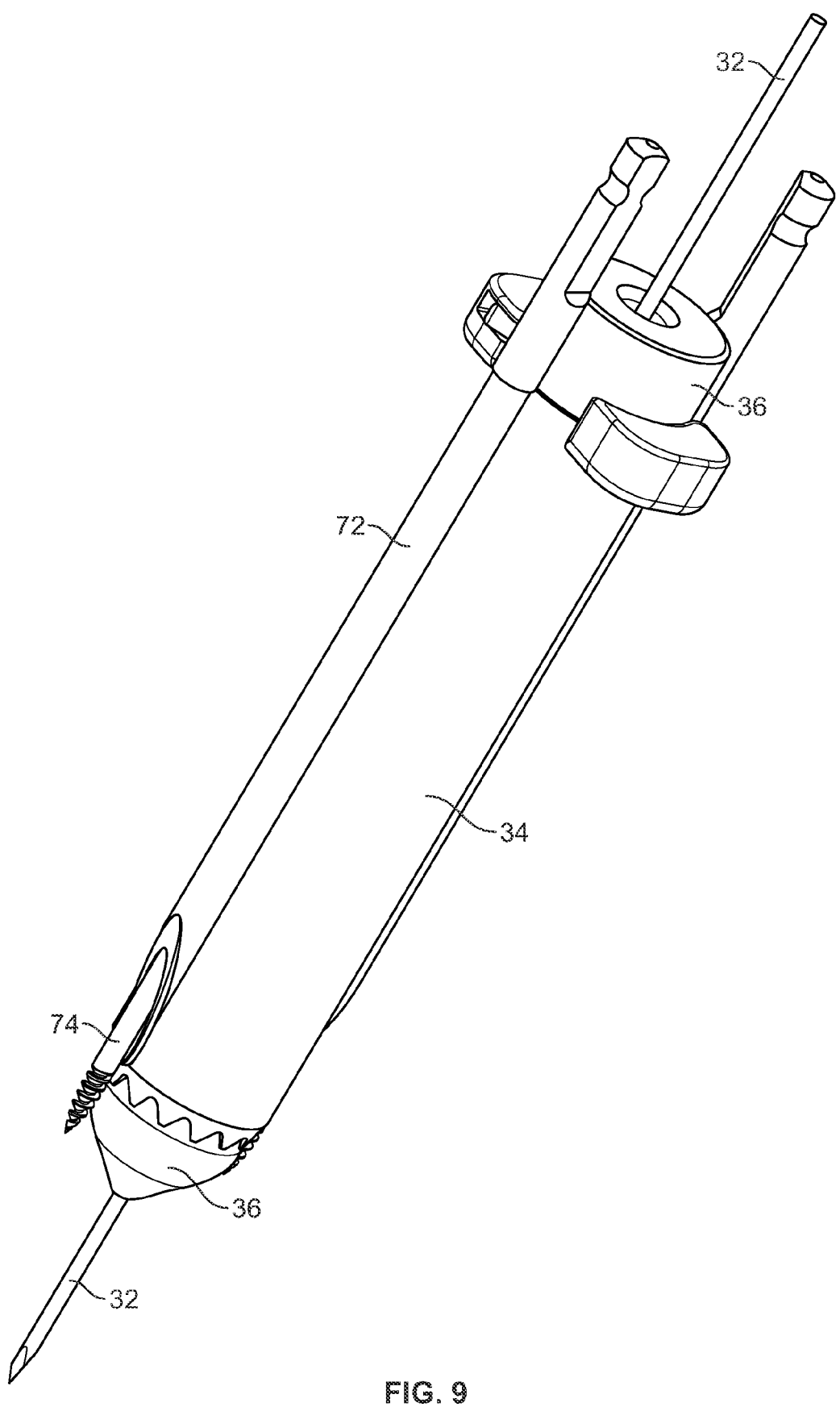
FIG. 9 is a perspective view of an assembly of a docking sleeve with retainers, and fasteners located therein, and a guidewire and an obturator.
Figure 10:
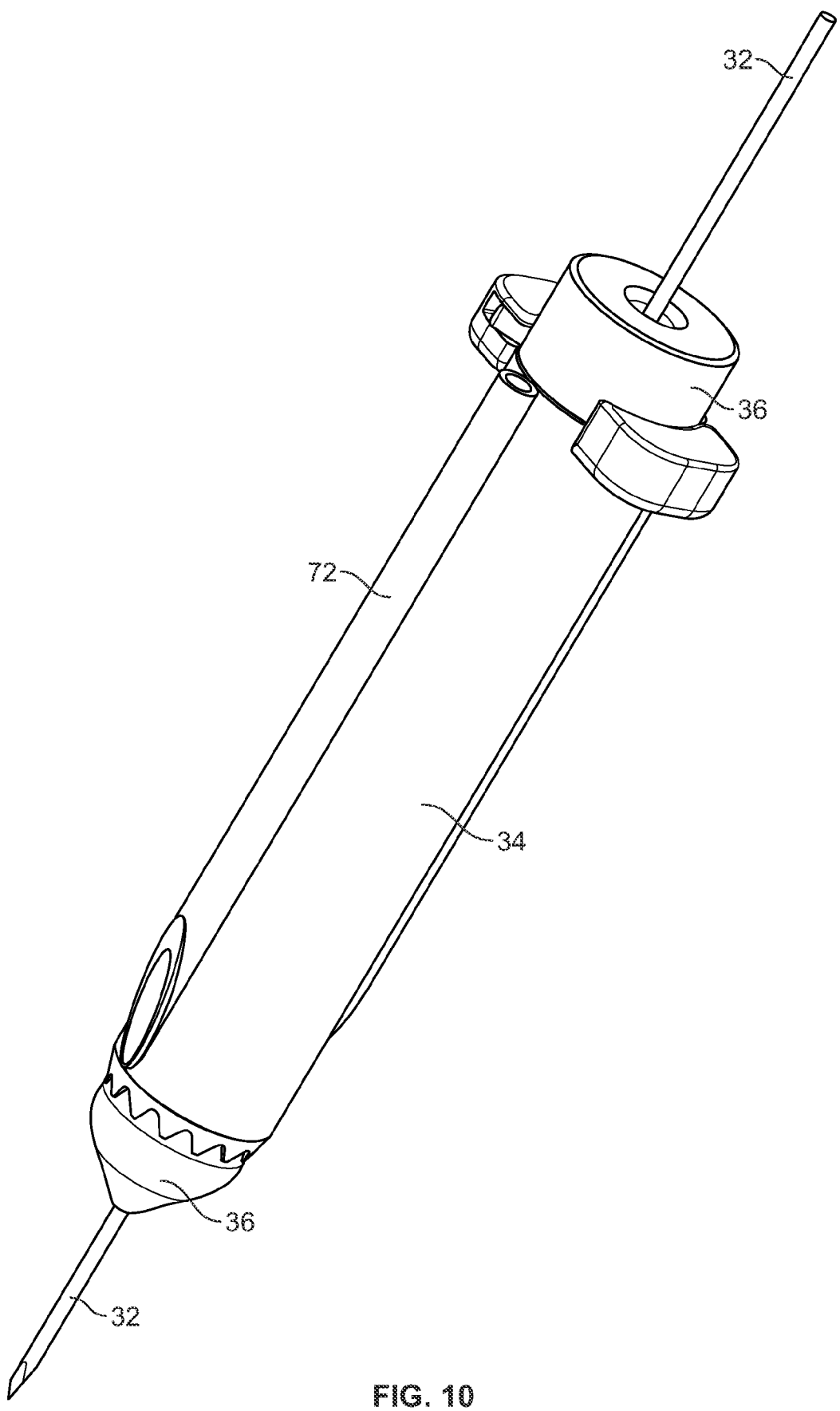
FIG. 10 is a perspective view of an assembly of a docking sleeve with retainers, without fasteners, a guidewire, and an obturator.
Figure 11A:
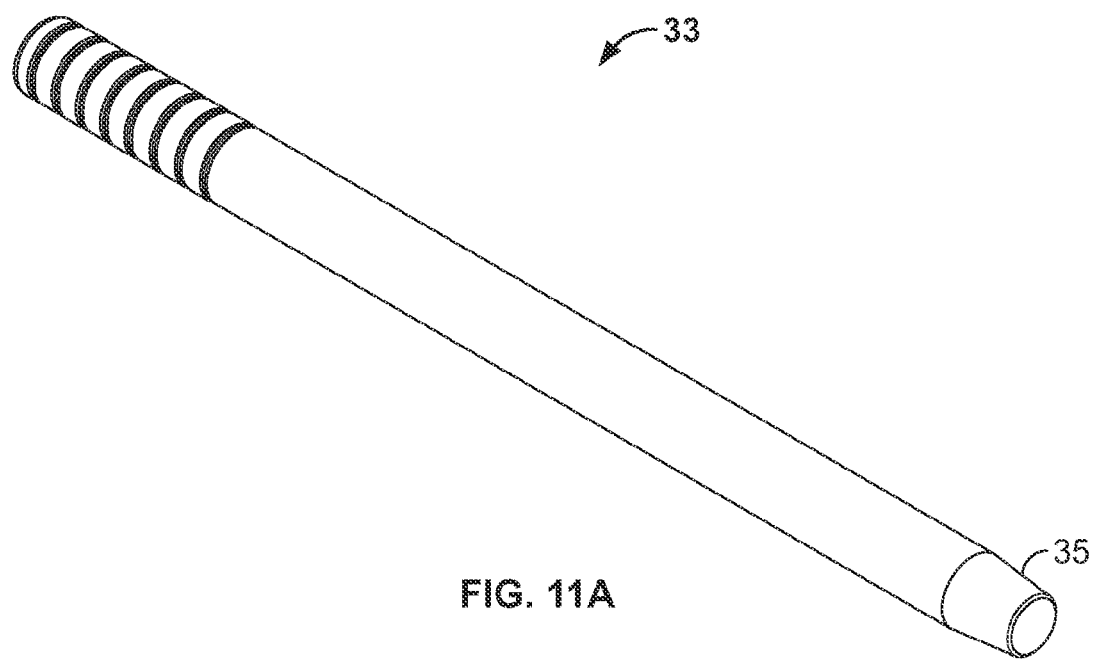
FIGS. 11 A-11H depict series dilators.
Figure 11B:
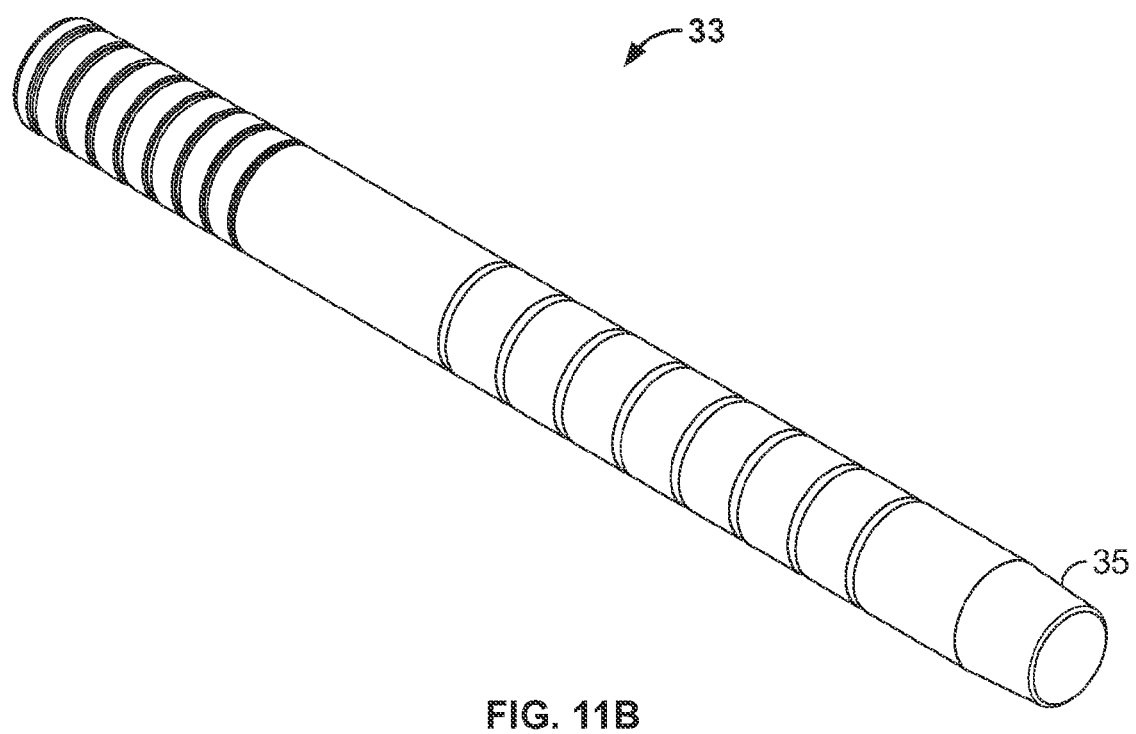
Figure 11C:
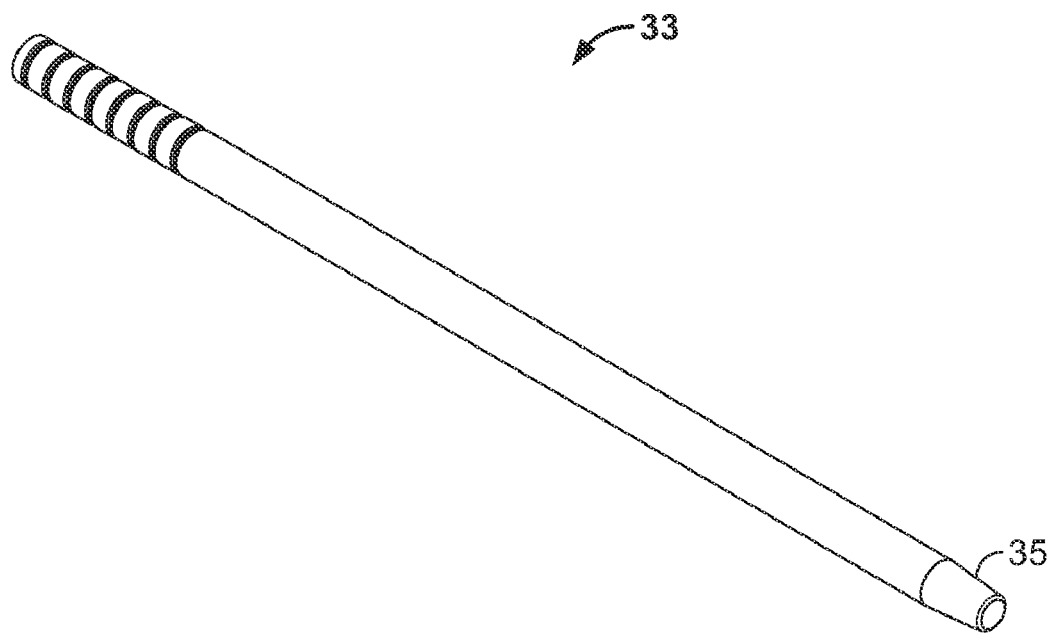
Figure 11D:
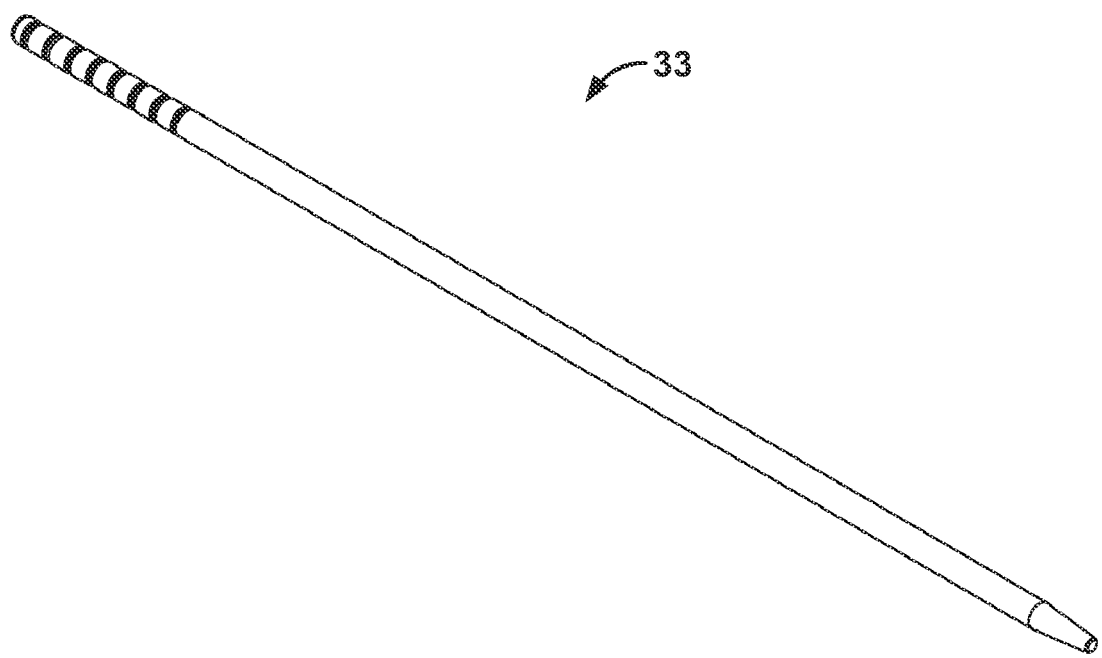
Figure 11E:
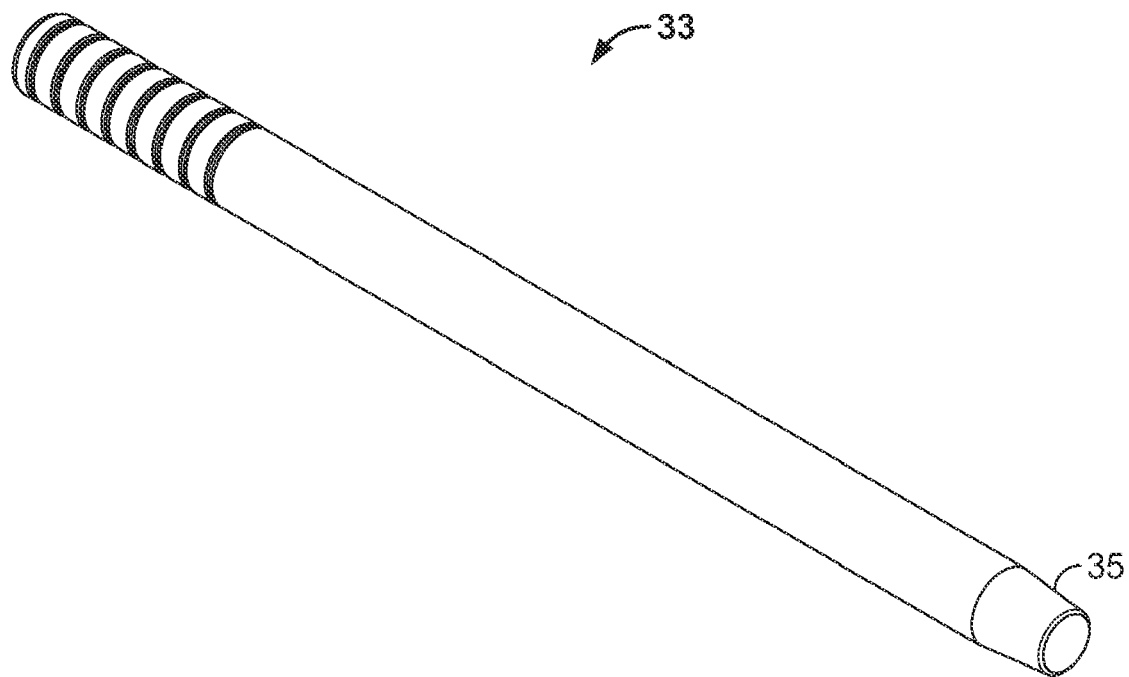
Figure 11F:
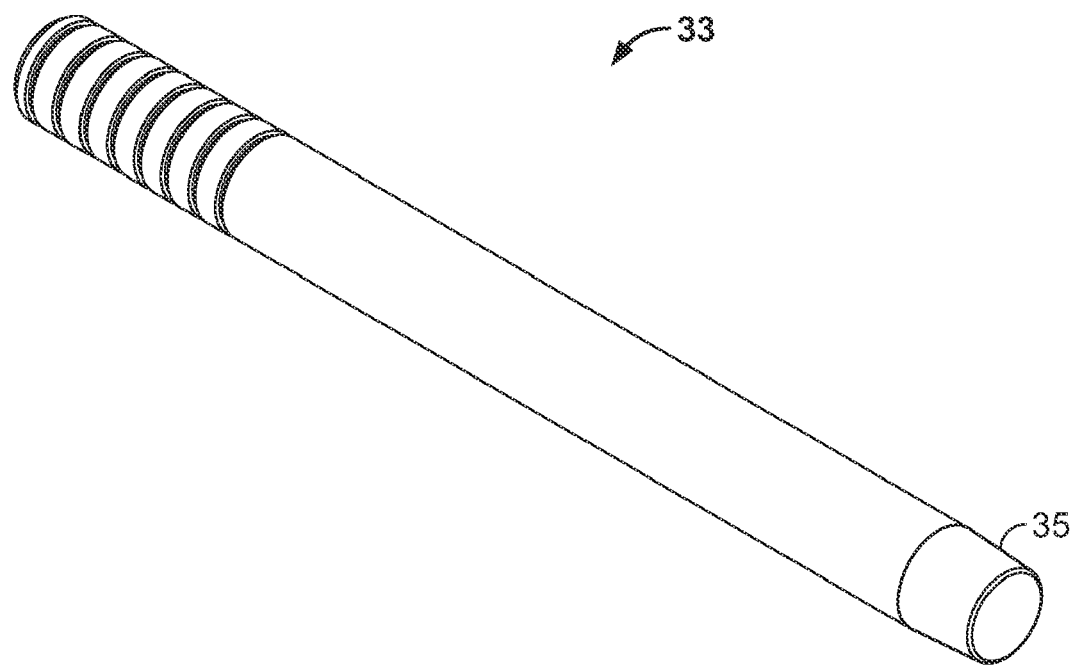
Figure 11G:
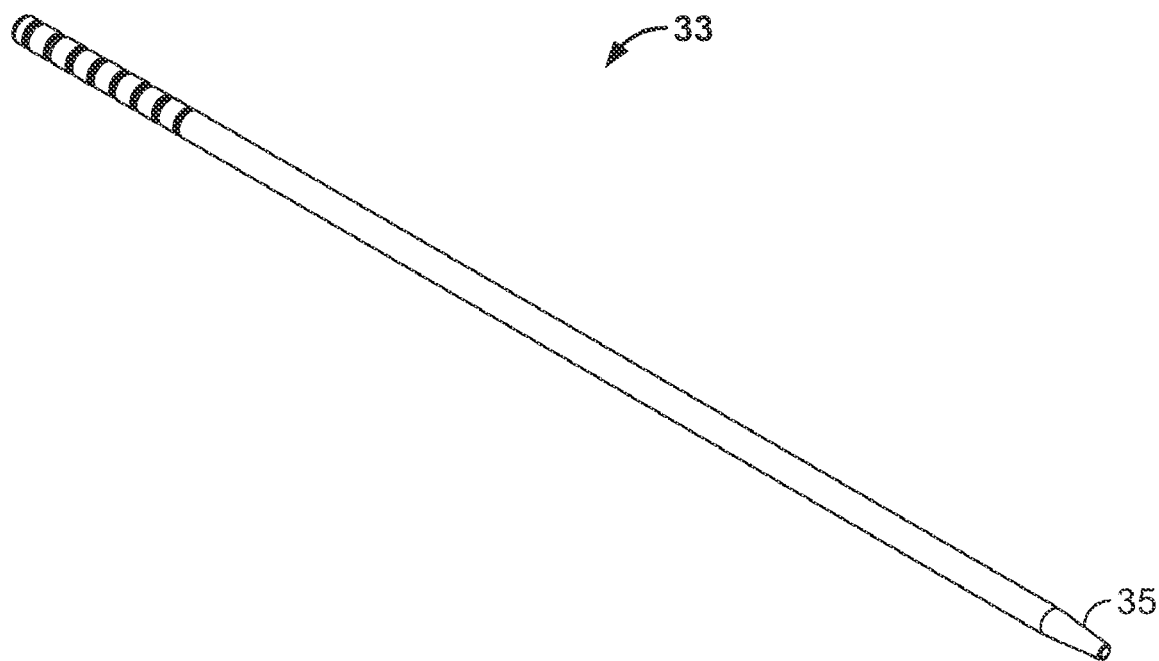
Figure 11H:
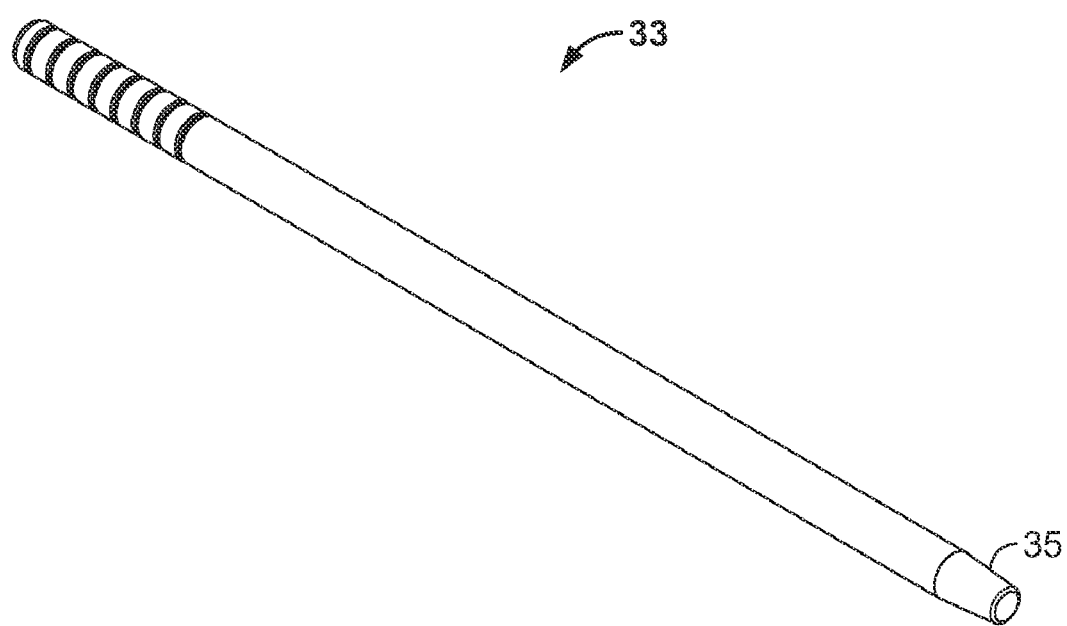

It is preferred that the obturator(s) 36 have a nose 60 that is sloped, curved, or otherwise well-suited for dilating tissue from a smaller diameter to a larger diameter as the obturator 36 is fed down the guidewire 32. The shaft 62 of the obturator 36 may be the same, reduced, or enlarged in diameter, compared to the nose 60. However, transitional sloped or radiused portions 64 are preferred to ease retraction of the device. The obturator 36 may include locking pins, boss, flange, threads or other structure to lock the obturator 36 into position. The proximal end of the obturator 36 may have a handle 66 or other area suited for improving the grip such that the instrument may be advance into the opening in a controlled fashion by the surgeon. Optimally, the ergonomic handle will improve grip, minimize slippage and surgeon discomfort. After the obturator(s) 36 have been used to stretch the tissue, the docking sleeve 34 can be advanced into the surgical site. FIGS. 9 and 10 illustrates how the docking sleeve 34 and obturator 36 would be advanced down the guidewire 32.

By sufficiently stretching the soft tissue, the force required to insert and position the bone anchors 20 and/or the docking sleeves 34 is reduced while also minimizing the potential damages to the soft tissues. This reduces the difficulty of the insertion procedure. After sufficiently stretching the incision through utilization of various dilation tools, the surgeon may then insert the docking sleeve 34, however, the bone anchors 20 may be inserted without the docking sleeves 34 in place. In this instance, it is preferred that the anchors are cannulated and follow the pre-positioned guidewire path, however surgeons may still choose to use non-cannulated anchors.

The docking sleeve 34 (FIG. 17) is the minimally invasive surgical portal through which at least the initial portion of the surgery may be performed. Depending on factors such as incision size and tissue elasticity, the surgeon may choose among several techniques to advance the docking sleeve 34 through the soft tissue toward the bone. For example, after the surgeon dilates the soft tissue using series dilators, obturator (s) 36 or the harpoon dilator 46 as discussed above, a final obturator 36, pre-loaded and housed within the docking sleeve 34, is advanced down the guidewire 32 together with the docking sleeve 34 toward the bone. If the obturator 36 and docking sleeve are advanced together, the obturator 36, after reaching the bone, may then be disengaged from the docking sleeve 34 such that the docking sleeve 34 then continues to advance until it contact the bone surface.

Another option for stretching the tissue and advancing the docking sleeve, combines several tools discussed previously. A smaller diameter obturator 36 may be advanced down the guidewire 32 to the site of the bone and one or more series dilators or open ended sleeves of larger diameter may then be guided over the initial obturator 36 until the desired tissue dilation is achieved. At that point in time, the docking sleeve 34 may then be advanced over the final expansion sleeve.

In another alternative, the docking sleeve 34 may be introduced over an obturator 36 by sliding the docking sleeve 34 over the final obturator 36. For example, the final obturator 36 may have a diameter slightly smaller than the internal diameter of the docking sleeve 34. In addition, the docking sleeve 34 could be introduced into the wound after the obturator 36 or expansion sleeves are removed by inserting a removable positioning plug. The plug keeps the docking sleeve generally centered over the guidewire 32.

Figure 18:
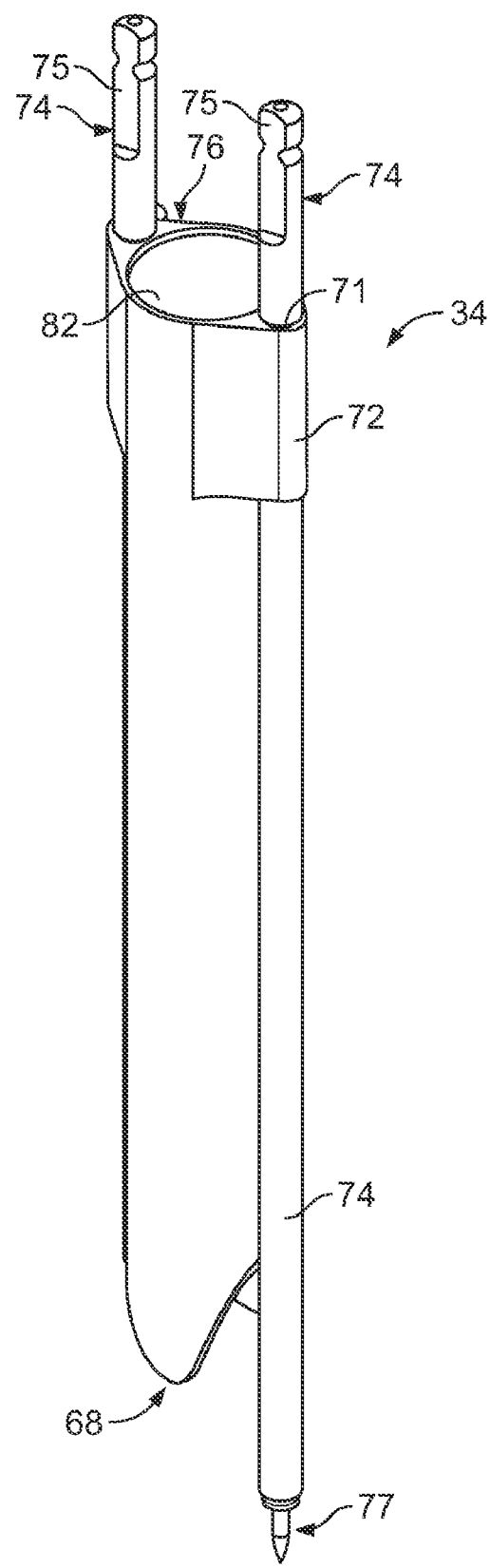
FIG. 18 is perspective view of another embodiment of a docking sleeve.

As illustrated in FIG. 17, the distal or bone engaging end 68 of the docking sleeve 34, preferably has an anti-skid portion 70 such as teeth, penetrating pins, or another non-smooth surface to retain the desired position of the sleeve on the bone. The anti-skid portion 70 prevents slippage across the bone surface. The distal, bone-facing end 68 may also include contouring as shown in FIG. 18. The contouring of the docking sleeve 34 allows it to sit generally flush against the adjacent non-flat bone surface. For example, one side of the proximal end 68 of the docking sleeve 34 is contoured to fit adjacent transverse process whereas the other side of the docking sleeve is contoured to fit adjacent the facet joint. The contouring may therefore vary from one side of the docking sleeve to another.

The docking sleeve 34 may also include one or more receivers 72 to house one or more fasteners 74 (FIGS. 17 and 18). Preferably, the receivers 72 are tubes or channels integrated or otherwise attached to the docking sleeve 34. (FIG. 17). Alternatively, the receiver(s) 72 may also be a small ring, snap, wire, or another retaining type fastener to guide and secure the docking fasteners 74. (FIG. 18). The receivers 72, as shown in both FIGS. 17 and 18, are located adjacent the cylindrical surface of the tubular wall of the docking sleeve 34, however, they could also be located adjacent or spaced from the inside wall surface. If the receivers 72 are placed on the inside wall surface of the docking sleeve 34 adjustments may be required to provide clearance for the implant and tools.

FIG. 17 illustrates how the receivers 72 may be sloped, radiused, chamfered, or sharpened near the proximal, bone-facing end to improve advancement of the sleeve 34 through the soft tissue. Further, the distal end of the docking fasteners 74 can also be so sloped, radiused, chamfered, or sharpened to improve insertion of the fasteners 74.

The proximal end 76 of the docking sleeve 34 may further include retainer 78. The retainer 78 cooperates with a locking pin, a boss, flange, thread, or other structure which could lock or temporarily secure the obturator 36 within the docking sleeve 34. The retainer 78 may also be used in cooperation with other instrumentation for other surgical procedures performed through the docking sleeve. The preferred retainer 78 shown is formed to house a locking pin 80 located on the obturator 36. The obturator 36 is slid into a window or bore 82 of the docking sleeve 34. After the obturator has been inserted, it is then rotated until the pin 80 is received in a circumferentially extending slot 84 of the retainer 78 through an open end 83. The opposite end 85 of the retainer slot 84 is closed so that the obturator 36 is stopped from further rotation with the pin 80 engaged by the closed end 85 of the retainer slot 84.

Preferably, the docking fastener(s) 74 are in the form of roughly 1-5 mm diameter pins and may have a self drilling auger type thread, although other fastener types may be used such as those having expanding heads. The fasteners 74 may be threaded or non-threaded, or the surgeon could use a threaded and a non-threaded fastener. The fasteners 74 are preferably AO standardized. While both manual and power tool advancement is possible, manual advancement is preferred. This can provide tactile feedback. To allow for more control of the fastener 74 and for the use of a driving tool such as a handle or ratchet, the proximal end of the fastener located remote from the surgical site may have a non-circular driver attachment portion 75.

In addition, the docking fastener(s) 74 may include a depth limiting feature, such as a collar, or depth guide, to prevent the pin from being drilled to deeply into the bone. Another option for the fastener(s) 74 is for each to have a proximal face 71 that is adapted to engage the docking sleeve 34 and the retainer 78 with the distal end 77 screwed into the bone thereby further securing the docking sleeve 34 relative to the bone.

In another embodiment, the anti-skid portion 70 of the docking sleeve 34 is adequate to hold the docking sleeve 34 into position on the skeletal anatomy. If the anti-skid portion secures the docking sleeve, the fastener(s) 74 may be unnecessary.

The window or bore 82 of the docking sleeve 34 is sized to provide space to perform the surgery and pass the desired implants into the surgical site. While the bore 82 of the docking sleeve 34 illustrated here is generally circular in cross-section, other shapes and sizes may be employed. The shape and size may be influence by the underlying anatomy, implants, and tools required for the surgery.

The docking sleeve 34 may be constructed of biocompatible materials, however, radiolucent materials such as polymers or carbon fiber may be preferred for better radiographic imaging of the area.

As previously described, the obturator 36 and the docking sleeve 34 are advanced down the guidewire 32, through the soft tissue until the nose 60 of the obturator meets the bone. At this point, the obturator 36 may be released by derotating or otherwise unlocking it from the retainer 78. By derotating the obturator 36, the locking pin 80 is disengaged from the slot 84 located on the docking sleeve retainer 78. After the obturator 36 and docking sleeve 34 are no longer mated together, the obturator can be pulled out of the sleeve 34. After the obturator 36 is removed, the docking sleeve 34 can then continue advancing to the bone surface. The obturator 36, along with any other tissue expansion tools, may be fully removed at any time after the docking sleeve 34 is advanced down to the bone.

Once the docking sleeve 34 reaches the bone surface, the sleeve 34 is securely attached to the bone. The docking fastener(s) 74 may be preloaded into the receivers 72 or may be loaded during or after advancement of the docking sleeve 34. To secure the sleeve 34 to the bone surface, the docking fasteners 74 may be advanced into the bone thereby positionally securing the docking sleeve 34 against the bone. If the docking sleeve 34 is not employing the fasteners 74, but instead utilizing the anti-skid portion 70 to secure the sleeve 34, the sleeve 34 may need to be rotated or pushed into the bone. Either way, the docking sleeve 34 is left secured to the bone by the docking fastener(s) 74, the anti-skid portion 70, or both. After the docking sleeve 34 is secured into position, the obturators 36 or other various dilation tools are removed.

Figure 19:
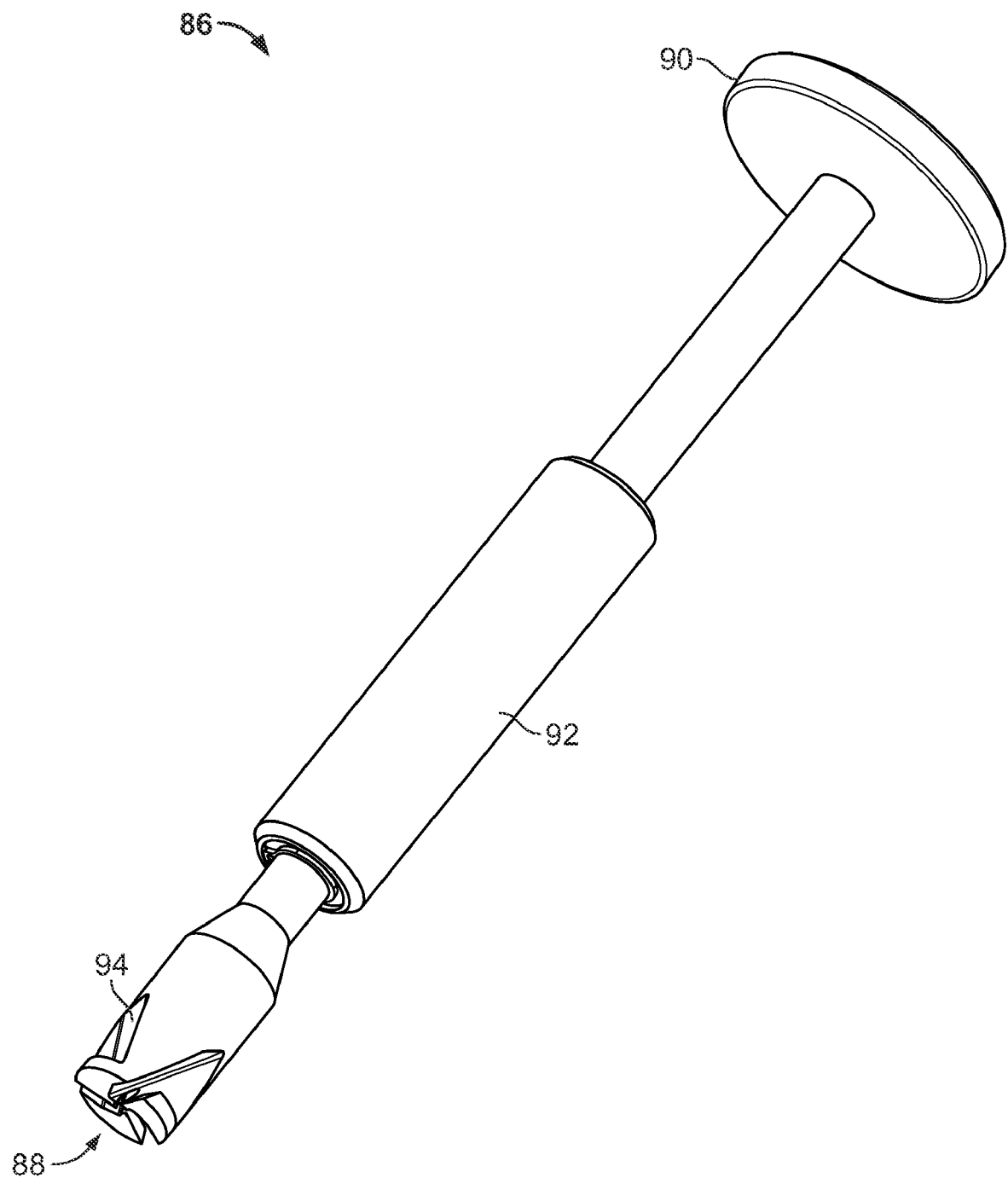
FIG. 19 is a perspective view of a facing tool.
Figure 19A:
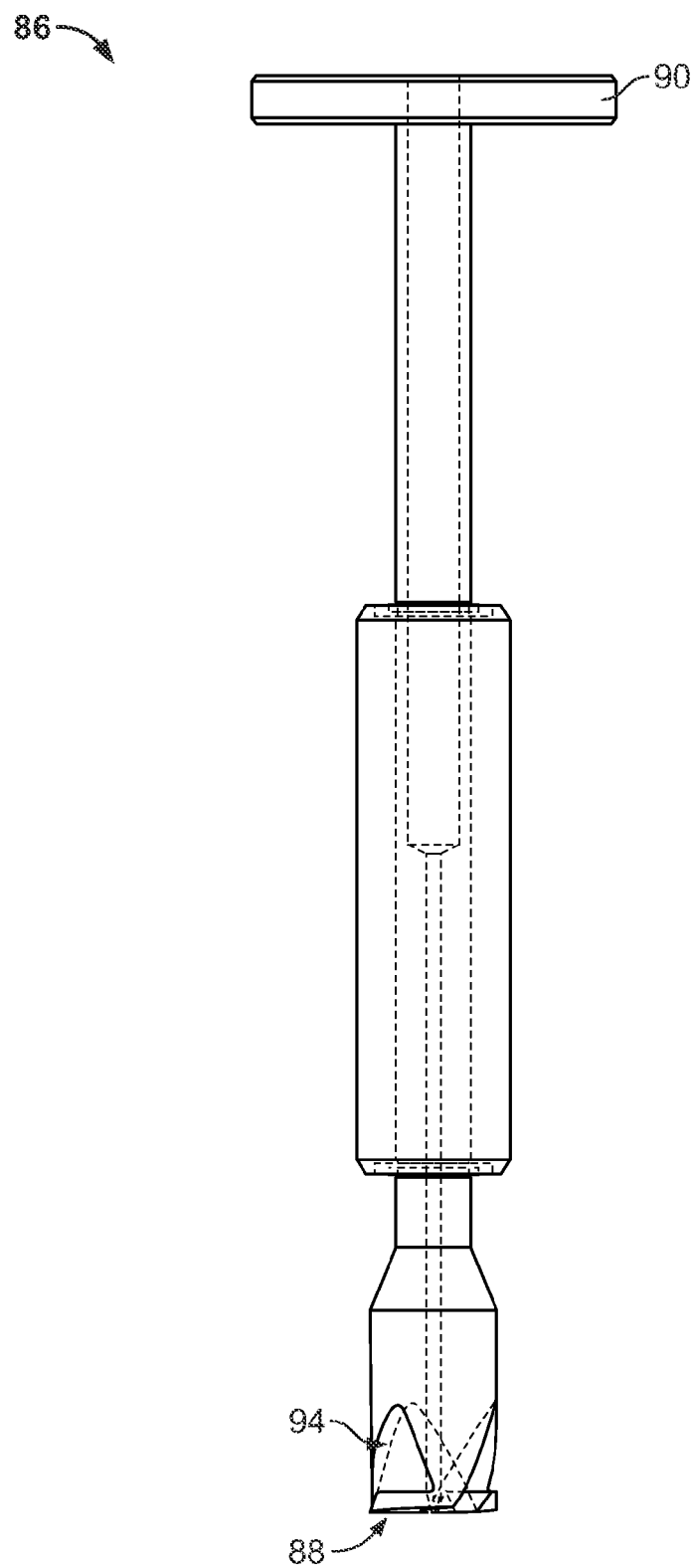
Figure 19G:
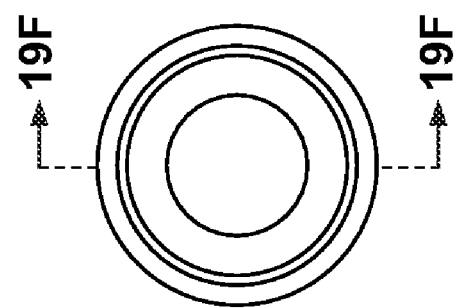
Figure 19F:
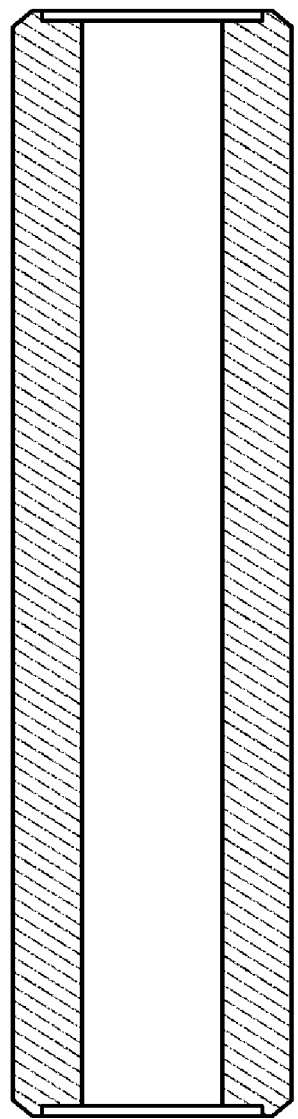

After creating a porthole to the surgical site via the docking sleeve 34, the surgeon may desire to prepare the bone by reshaping the surface. For example, if there is anything in the way such as an osteophyte overlying the area where the anchor 20 will be seated a surgeon can remove potentially interfering structures using a facing tool 86. The facing tool 86 (FIG. 19) may be used to refine bone surface and create a flattened area suitable for seating implants. The facing tool 86 may be cannulated and utilize the guidewire 32 for positioning within the docking sleeve 34 or may be non-cannulated and guided by the inside wall of the sleeve 34 in which case the guidewire 32 is not used or previously removed.

The facing tool 86 preferably includes a generally flat cutting portion 88. The cutting portion 88 removes, flattens, and cuts away the surface of the bone as the tool 86 is rotated. Alternatively, the tool 86 may include a shaped cutting portion 88 to shave the bone in a contour such as a concave, dome or another shape beneficial to inserting various implants. The facing tool 86 may include a handle portion 90 and a depth stop 91, in the form of a stop collar located to engage the top of the docking sleeve 34. Such a depth stop generally avoids having the tool advanced too far into the bone. A centering portion 92 on tool 86 may be sized to the inside diameter of the docking sleeve 34. The centering portion 92 may keep the tool generally centered in the docking station 34 to keep the cutting portion 88 from wearing against the sides of the docking sleeve window 82. In addition, a bone chip reservoir 94 that may be a space or opening near the cutting portion 88. This reservoir 94 may accumulate the bone chips being removed from the bone surface as the tool is rotated.

Figure 20:
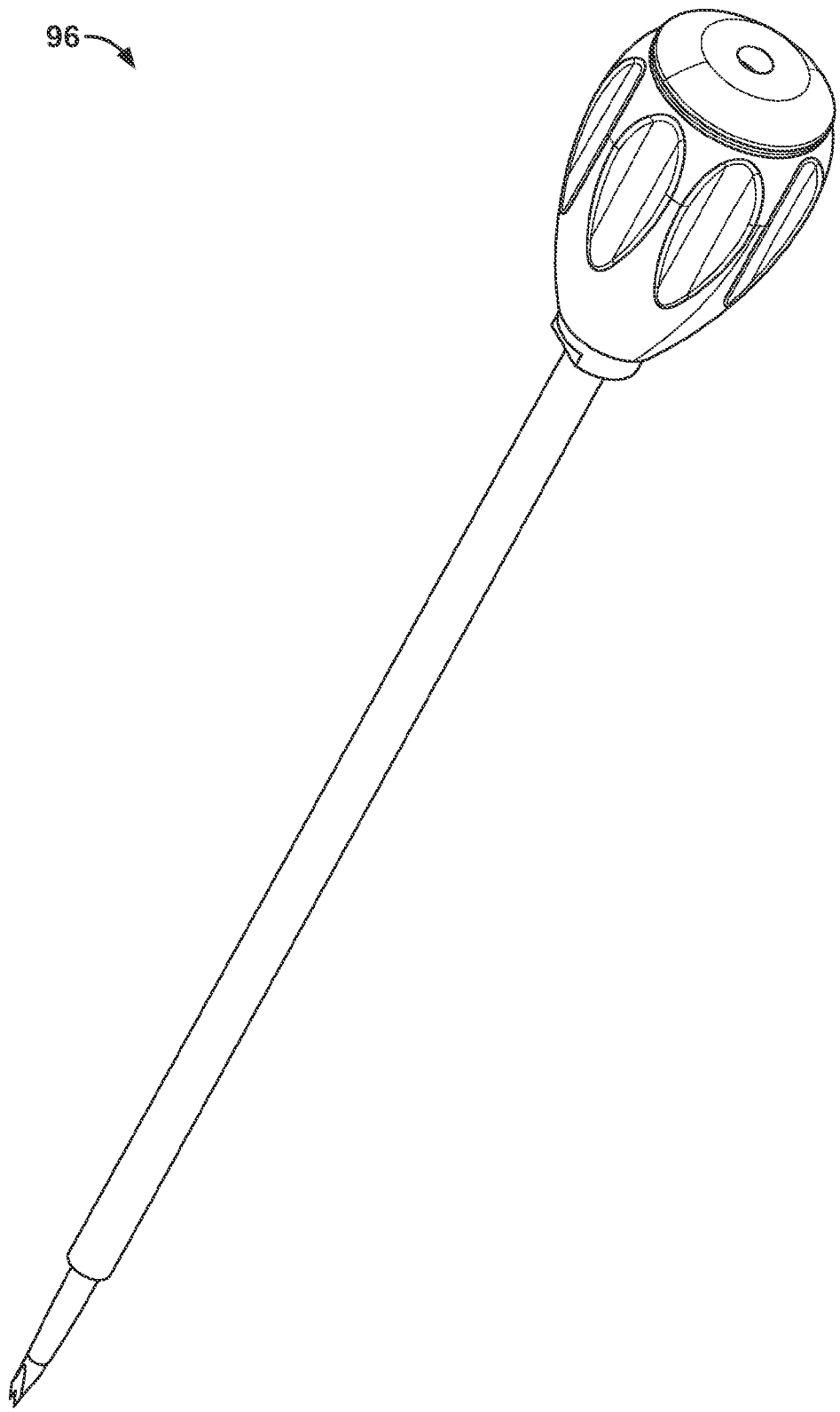
FIG. 20 is a perspective view of a cannulated awl.

Before attaching the bone anchor 20, a cannulated awl 96 may be used to perforate the cortex of the bone overlying the pedicle. The cannulated awl 96, shown in FIG. 20, may slide down the guide wire and then be driven into the bone by tapping on the proximal or upper end projecting out from the docking sleeve 34 with a mallet. After the cortex of the bone is breached and a depression or opening is made, the awl 96 can be removed. The depression can also be created by rotating or otherwise manipulating the cannulated awl 96. Alternatively, if the guidewire 32 is not being used or has previously been removed, the awl 96 can be visually placed at the bone site with the surgeon looking through the docking bore 82 for this purpose. Another option is to have a collar on the shaft of the awl tool that guides the awl 96 down the docking sleeve 34 toward the bone site.

If a guidewire 32 is still inserted into the wound, the surgeon may choose to remove it at this time. After which, the pedicle finder 30 or another drilling tool may be advanced down the docking sleeve 34 toward the bone where the pedicle finder 30 may create a pilot hole of suitable and safe depth for the bone anchor 20. Whether or not the surgeon wishes to tap a pilot hole often depends on the anchor type and surgeon preference. Further, the surgeon may also wish to use a probe to assess the position of the hole and ensure that it has not veered into an unintended or unsafe direction. When a pilot hole or tap is made, it is appropriately sized to the bone anchor that will implanted.

Verifying the hole position can be difficult in guidewire 32 dependent systems because the implants and instruments are usually constrained to the guidewire 32. In such cases, the implant follows where the guidewire 32 is directed and if a guidewire 32 is improperly placed the implant placement can be improper and potentially harmful. Therefore, it is preferred that the guidewire 32 eventually be removed, if used at the beginning of the procedure.

Figure 21:
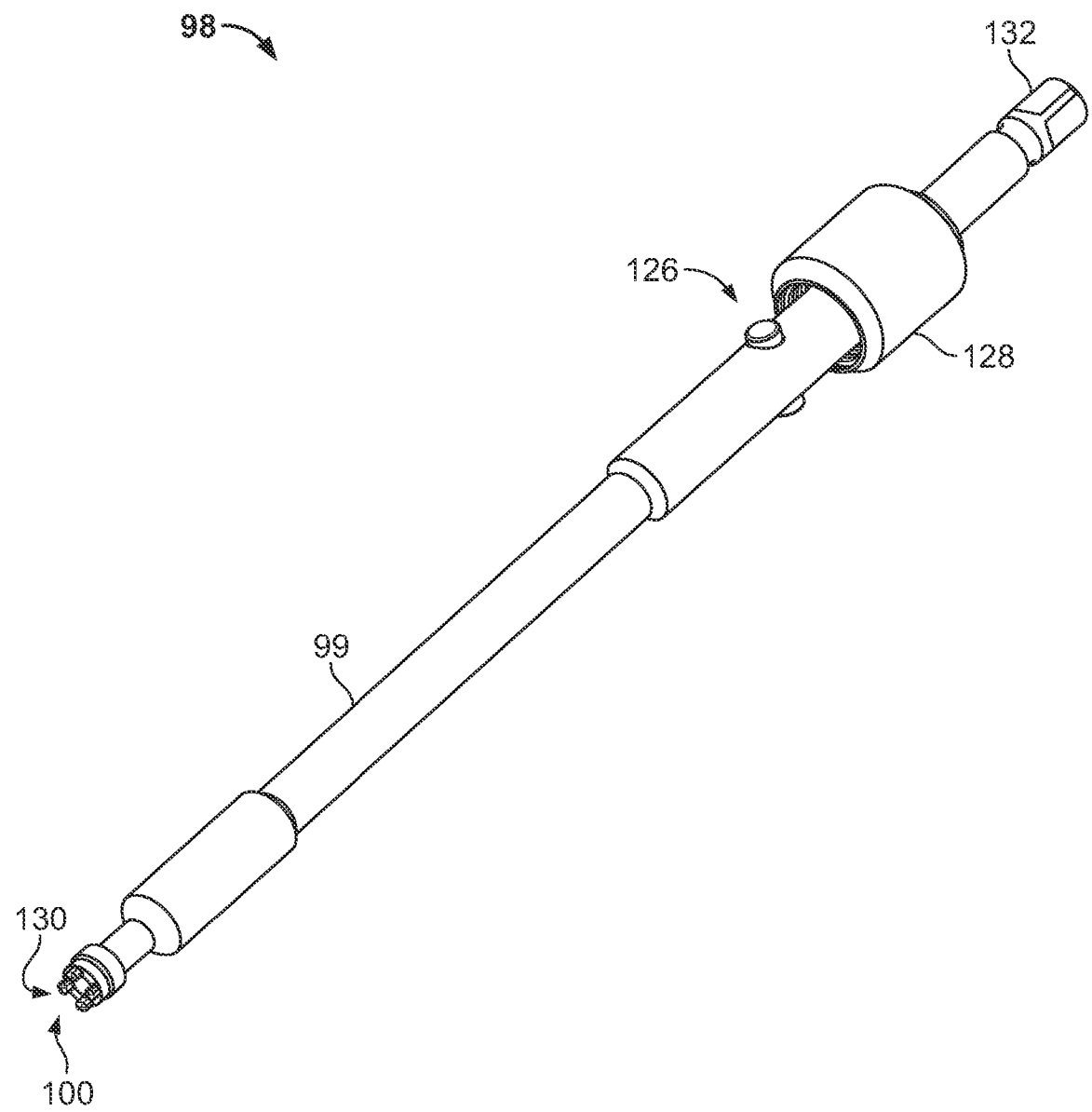
FIG. 21 is a perspective view of a screw driver.
Figure 21A:
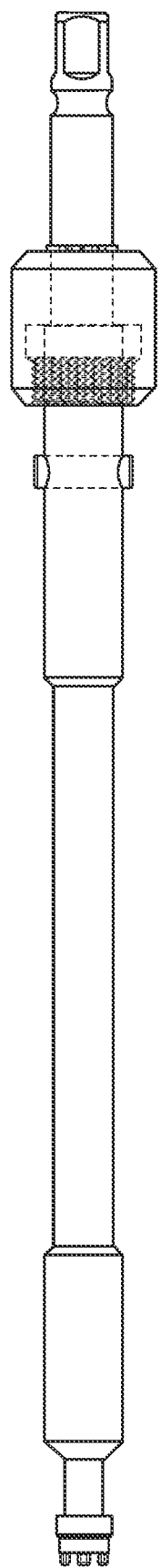
Figure 21C:
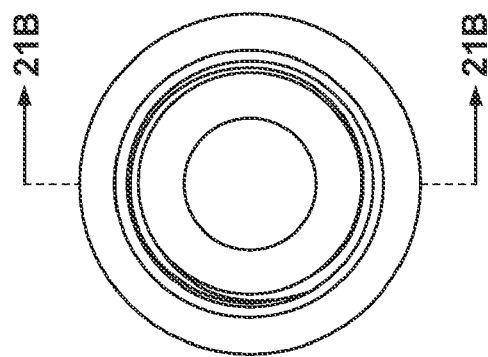
Figure 21B:
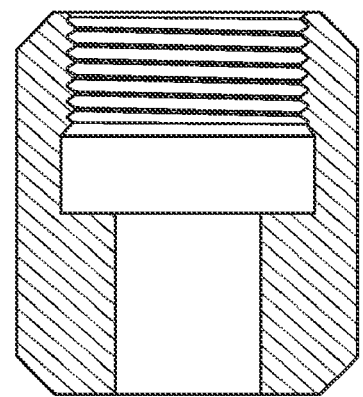

Then, with the guidewire 32 removed, the placement of the pilot hole verified, the surgeon may now advance the anchor 20 and a screw driver 98 assembly down the docking sleeve 34. Then, the anchor 20 can be driven into the bone through the prepared pilot hole by rotating the screw driver. As shown in FIG. 21, the screw driver 98 has a first end with a set of prongs 100 that mate with a proximal end of the anchor such that when the screw driver 98 is rotated, the anchor advances into the bone.

There are several preferred methods of delivering the bone anchors into the surgical site. Therefore, numerous instruments are disclosed to assist in insertion of the implant. The instruments can be used in varying combination and a few examples are disclosed herein.

Figure 22:
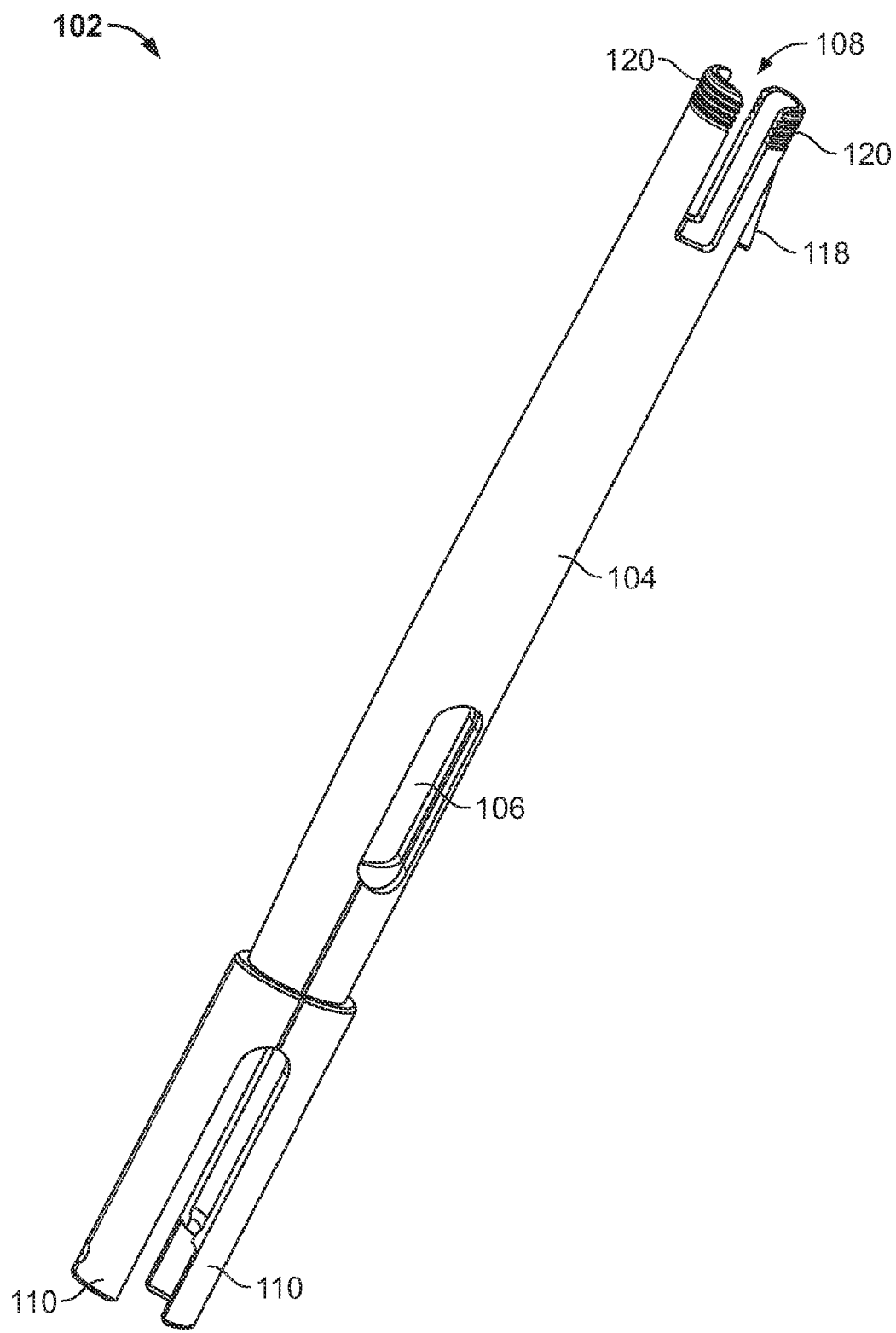
FIG. 22 is a perspective view of a yoke manipulator.
Figure 23:
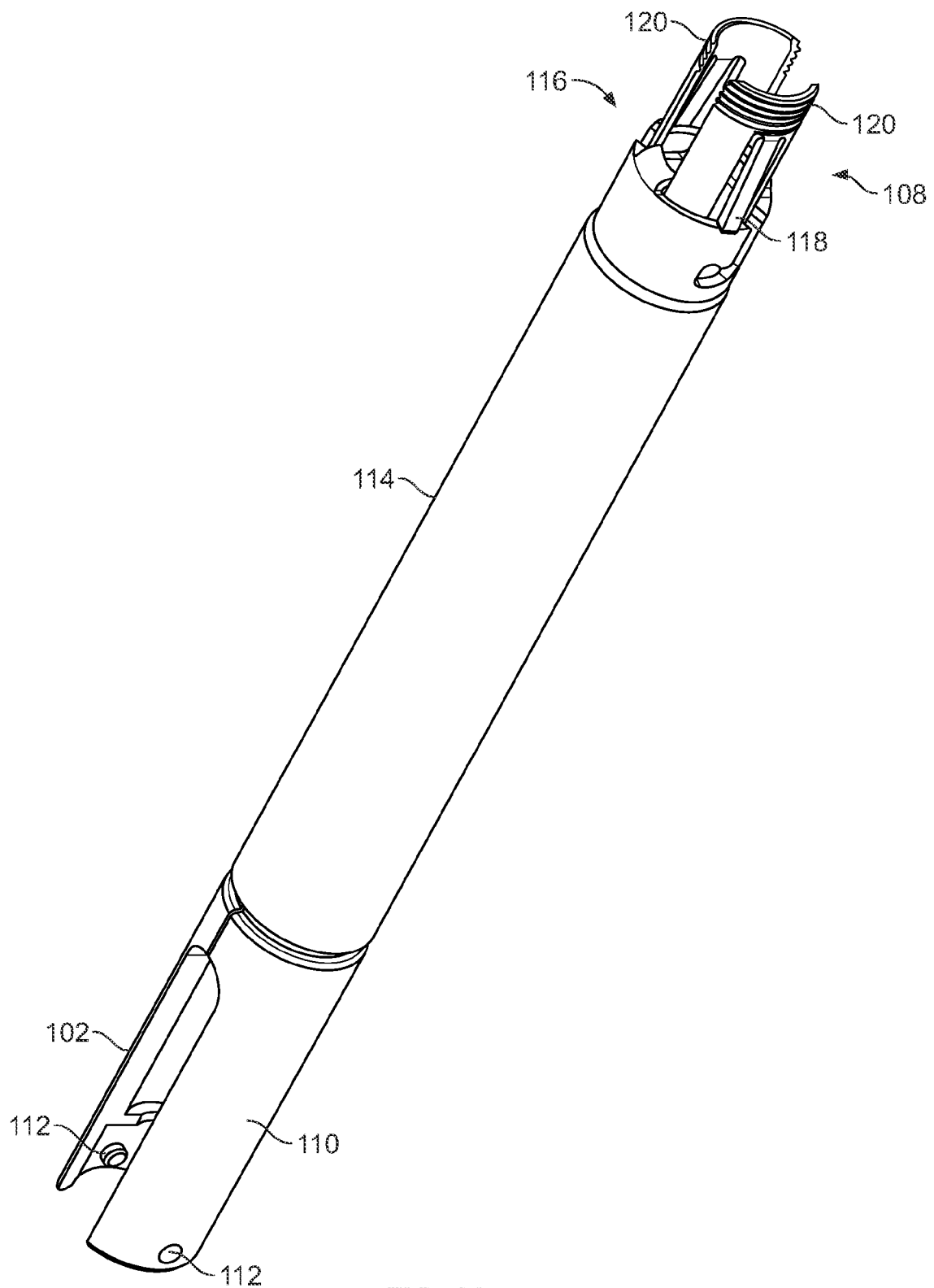
FIG. 23 is a perspective view of a yoke manipulator with a restraint.
Figure 23G:
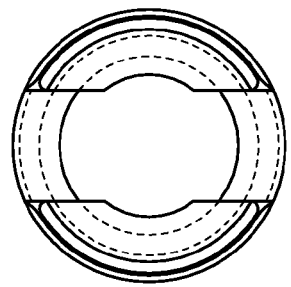
Figure 23I:
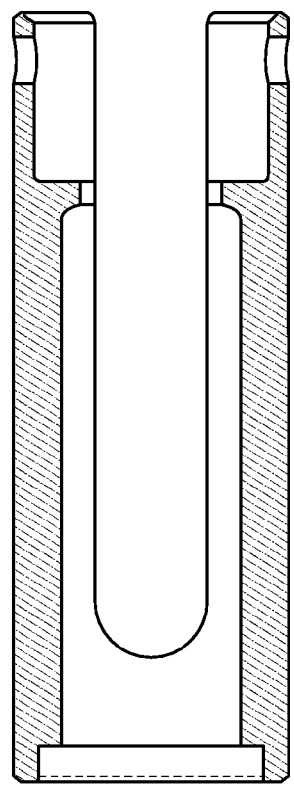
Figure 23F:
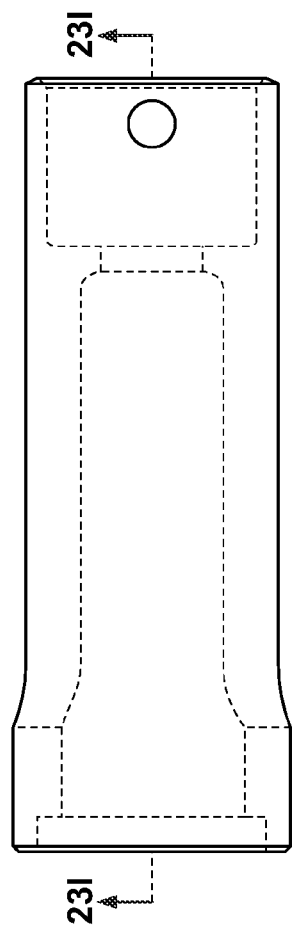
Figure 23H:
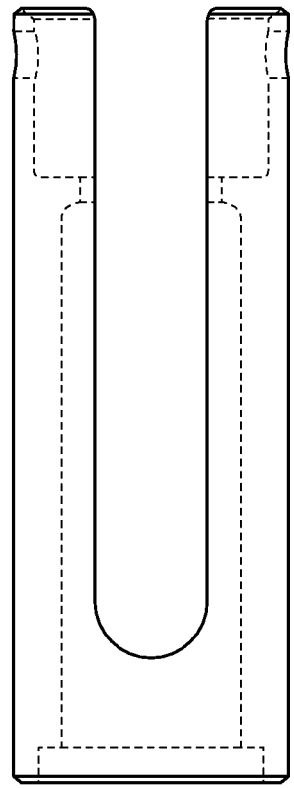
Figure 23J:
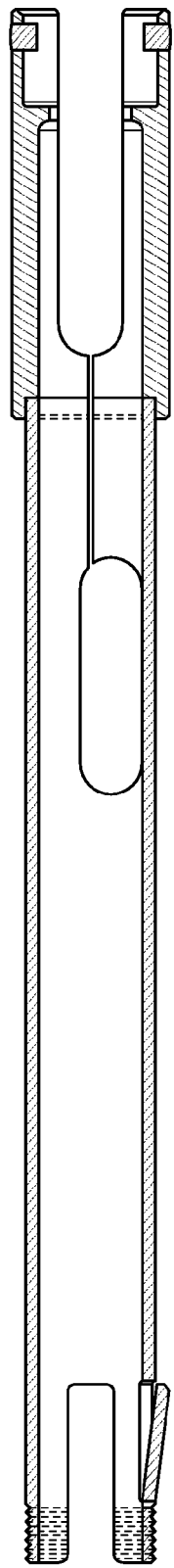
Figure 23K:
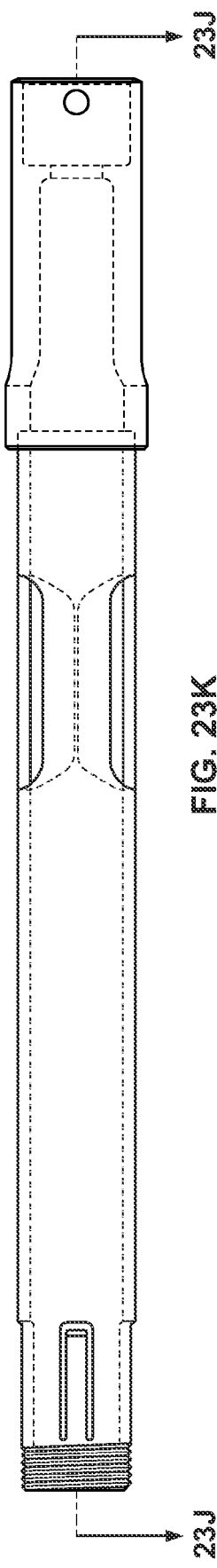
Figure 23L:
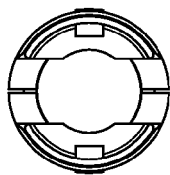

A yoke manipulator 102 is shown in FIG. 22. The manipulator is mated to the yoke 22 and thereby the anchors 20. The yoke manipulator 102 has at least a shaft 104, a slot 106, and manipulator end 108. The yoke manipulator 102 may be used to manipulate and help insert the anchor 20 and yoke 22 into the bone by attaching and holding the yoke 22 within one or more manipulator arms 110 at the distal end of the manipulator. At least one of the arms 110 is flexible and may preferably spring outward to a resting position wherein the inner diameter between the two arms is greater than the diameter of the yoke 22. Alternatively, one or more of the arms 110 may flex only when the yoke 22 is inserted between the arm portions. The arms 110 may include a boss, recess, flange, or other retainer to engage a complementary structure on the yoke 22. As shown in FIG. 23, the retainer 112 is a pair of bosses located on each arm on the inside of the manipulator shaft. Such an engagement retains the yoke 22 in predetermined alignment with the yoke manipulator 102. Such a structure also prevents the yoke from prematurely separating from the manipulator arms 110. The bosses seat in corresponding slots on the anchor yoke 22.

The yoke manipulator 102 may include a slot, cut, or space defining each arm portion 110. The manipulator shaft 104 may be recessed to accommodate a restraint 114 such as a locking sleeve, collar, or outer sheath shown disposed over the yoke manipulator in FIG. 23. The restraint 114 prevents or limits outward expansion of one or more of the arms 110. The restraint 114, depicted as a locking sleeve in FIG. 23, extends over a portion of the arms 110 to securely capture the anchor yoke 22. For example, the arms 110 are positioned around the yoke 22 and since the arms 110 have some flexibility, the restraint 114 is slid down the manipulator 102 to strengthen the connection. The restraint may also include a positioner 116 to orient the restraint 114 to the yoke manipulator 102. The positioner 116, for example, may be in the form of a flange, boss, recess, or other structure complementary to the yoke manipulator 102 for alignment. The restraint 116 may also include retraction structure 122, such as a slot, flange, boss, or recess for engagement of a tool handle to remove the restraint 114.

The manipulator end 108, opposite the arms 110, further includes a positioner 116. The positioner 116 is preferably in the form of a slot, boss, or flange that may orient the locking restraint 114 on the yoke manipulator 102 and/or to align each bone anchor 20 relative one another for passage of the connecting member 26. The yoke manipulator 102 may also include a releasable stop 118 to temporarily hold the restraint 114 over the arms 110. Connecting structure 120 such as threads, flanges, slots, or bosses may be present to connect an instrument such as the screw drive assembly.

One of the yoke manipulators used in the system may be a long slot yoke manipulator 124. The long slot manipulator 124 includes a shaft 104, slot 106, and arms 110, like the short slot manipulator 102, however, the slot 106 on the long slot manipulator is generally longer than on the short slot manipulator 102. For example, as shown in FIG. 2, the short slot is generally less than half the length of the long slot. The long slot manipulator 124 provides the surgeon with additional clearance during the insertion of the connecting member 26 as is more fully explained below. The long slot manipulator 124 may incorporate most of the features of the short slot manipulator 102. It is contemplated that the slots in the manipulators be of different lengths. In fact, as long as one of the manipulators has enough clearance for the connecting member 26 to be inserted, the other manipulator may include a smaller slot or may include a slot on only one side. As discussed below, the long slot manipulator 124 is proximate to the rod inserter 140 to provide the sufficient clearance. Preferably, the MISS having two bone anchors with have one long slot manipulator 124 and one short slot manipulator 102. If the implant has three bone anchors, the MISS will include two long slot manipulators 124 and one short slot manipulator 102. It is preferred that a system not include more than one short slot manipulator 102 because additional short slot manipulators 102 may interfere with insertion of the connecting rod 26. In any event, whether the slots are short or long, they must provide suitable access to pass the connecting member into the yokes.

The number of yoke manipulators 102, 124 preferably corresponds to the number of bone anchors 20. It is also preferred that each manipulator should generally be aligned relative to one another. This alignment may be done by placing a strut or guide 142 between the postioners 116 on each of the manipulators as discussed below. After the manipulators 102, 124 are in position, the docking sleeves 34 may be removed although typically the docking sleeves cannot be removed if a strut or guide is located between the manipulators. The shafts 104 manipulators 102, 124 are hollow thereby providing access to the anchor 20 and manipulator 22.

As mentioned above, the screw driver assembly or inserter 98 advances the anchor into the bone. The driver 98 is sized to fit within the yoke manipulators 102 and 124. The driver 98 includes a shaft 99 and a positioning structure 126, preferably in the form of a pin, boss, flange, or other structure complementary to the positioner 116 on the yoke manipulator 102, 124 for orienting the screw driver 98 to the yoke manipulators 102, 124. The driver 98 may also include a removable capture 128 for capturing the screw driver 98 in the yoke manipulator 102, 124 and holding the screw drive surface 130 tight within the head of bone anchor 20. In this embodiment, the removable capture 128 on the driver 98 and the connecting structure 120 on the yoke manipulator 102, 124 are inter-mating threads, but other connections such as a bayonet style connection could be used. Such an association ensures that the driver 98 engages the anchor 20 while the manipulator 102, 124 engages the yoke 22. Opposite the screw drive surface 130, the driver 98 may include an engagement end 132 for non-rotatable engagement with a removable handle, ratchet, or fixed handle. In addition, the driver 98 may include one or more guide surfaces 134 that have an outer diameter generally similar to the inner diameter of the yoke manipulators 102, 124 such that the screw driver 98 remains centered within the manipulator. After the driver 98 is mated with the anchor 20, the driver 98 and manipulator 102 or 124 are both turned at the same rate, such that there is no relative motion between the anchor 20 and the yoke 22. After the anchor has been inserted, the driver 98 may be removed.

Figure 24:
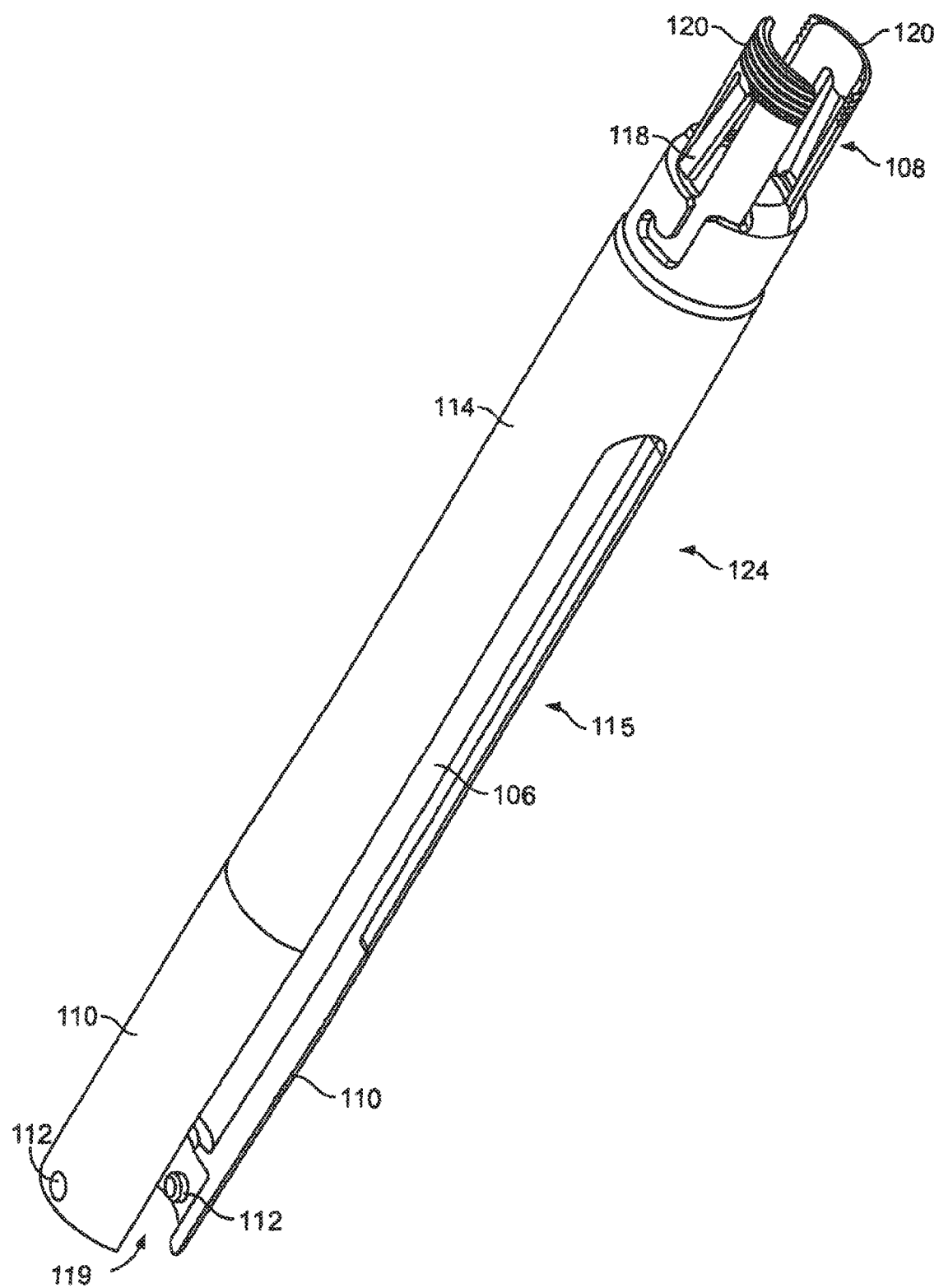
FIG. 24 is a perspective view of another yoke manipulator having a restraint thereon.
Figure 25:
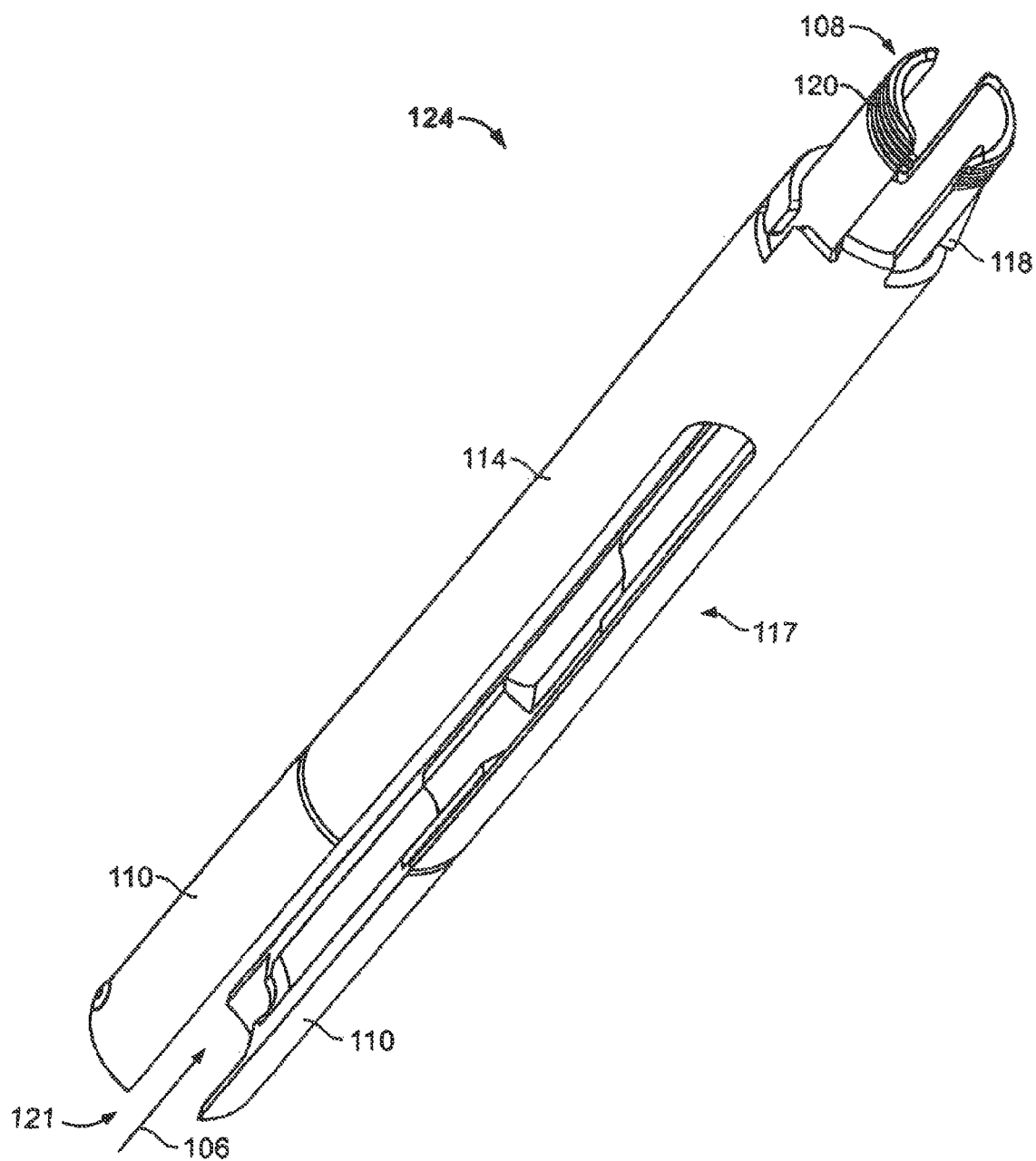
FIG. 25 is another perspective view of the yoke manipulator having a restraint thereon of FIG. 24.
Figure 26:
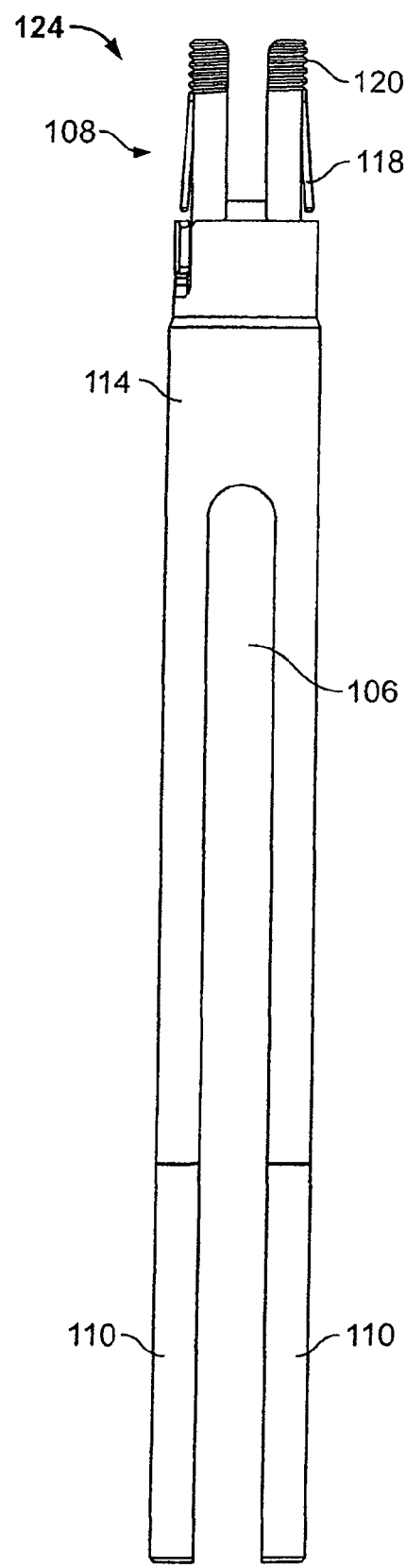
FIG. 26 is a side plan view of the yoke manipulator and restraint of FIG. 24.
Figure 27:
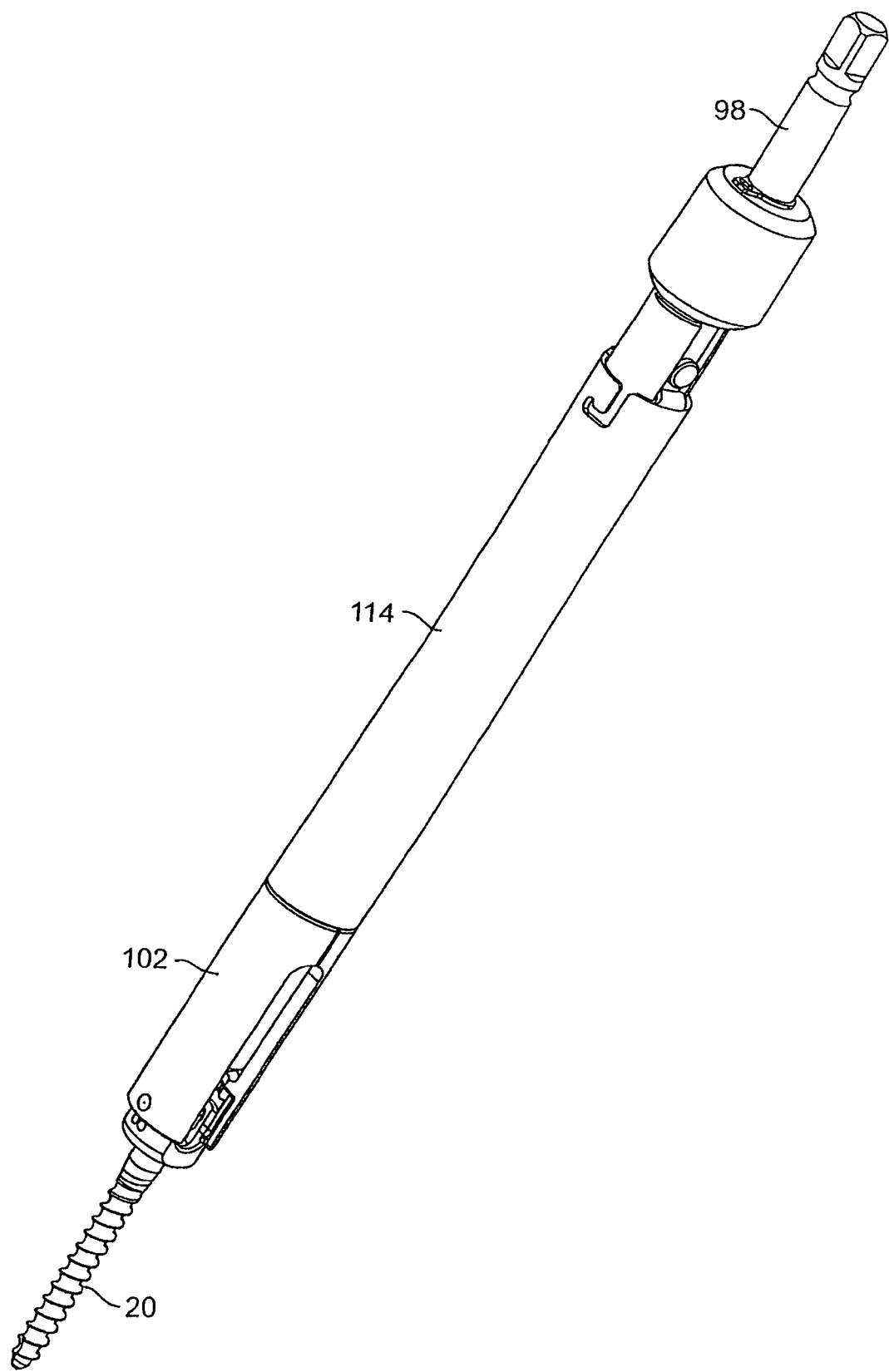
FIG. 27 is a perspective view of an assembly of the anchor, yoke manipulator, and screw driver.

FIG. 27 illustrates a screw driver 98, yoke manipulator 102, restraint 114, and a bone anchor 20 as an assembly in operable relation to each other. This preferred assembly is advanced through the window or bore 82 of the docking sleeve 34. As the assembly illustrates, the bone anchor 20 and yoke 22 may be loaded into a yoke manipulator 102 or 124 and captured between the arms 110 prior to loading the assembly into the docking sleeve 34. The retainer 112 engages a pair of recesses 136 on the opposing walls 23 of the yoke 22. The manipulator restraint 114 is slid over the shaft of the manipulator 102, 124 securing the yoke manipulator arms 110 around the yoke 22. As shown in FIGS. 24-26, the restraint 114 is in the form of a locking sleeve that has axially extending slots 115, 117 aligned with axially extending slots 119, 121 of the manipulator 124. The restraint 114 aligns with the positioner slot 116 on the yoke manipulator. The releasable stop 118 axially secures the restraint 114 onto the yoke manipulator 102, 124. After assembly, the instrumentation may now be fed into the docking sleeve 34. Alternatively, as shown in FIG. 22 the screw driver 98 may also be added to the assembly before insertion into the sleeve 34.

If the screw driver 98 is fed down the center of the manipulator 102, 124 after the anchor 20 has been advanced down the manipulator, the driver 98 advances until the screw drive surface 130 engages the anchor sockets 138. The positioner 126 of the driver 98 aligns with the positioner 116 of the manipulator for full engagement of the drive surfaces. The guide surface 134 will center the driver 98 within the manipulator 102, 124. The driver 98 is secured to the manipulator 102, 124 by threaded engagement of the internally threaded removable capture nut 128 to the thread connector 120 at the proximal end of the manipulators.

Figure 28:
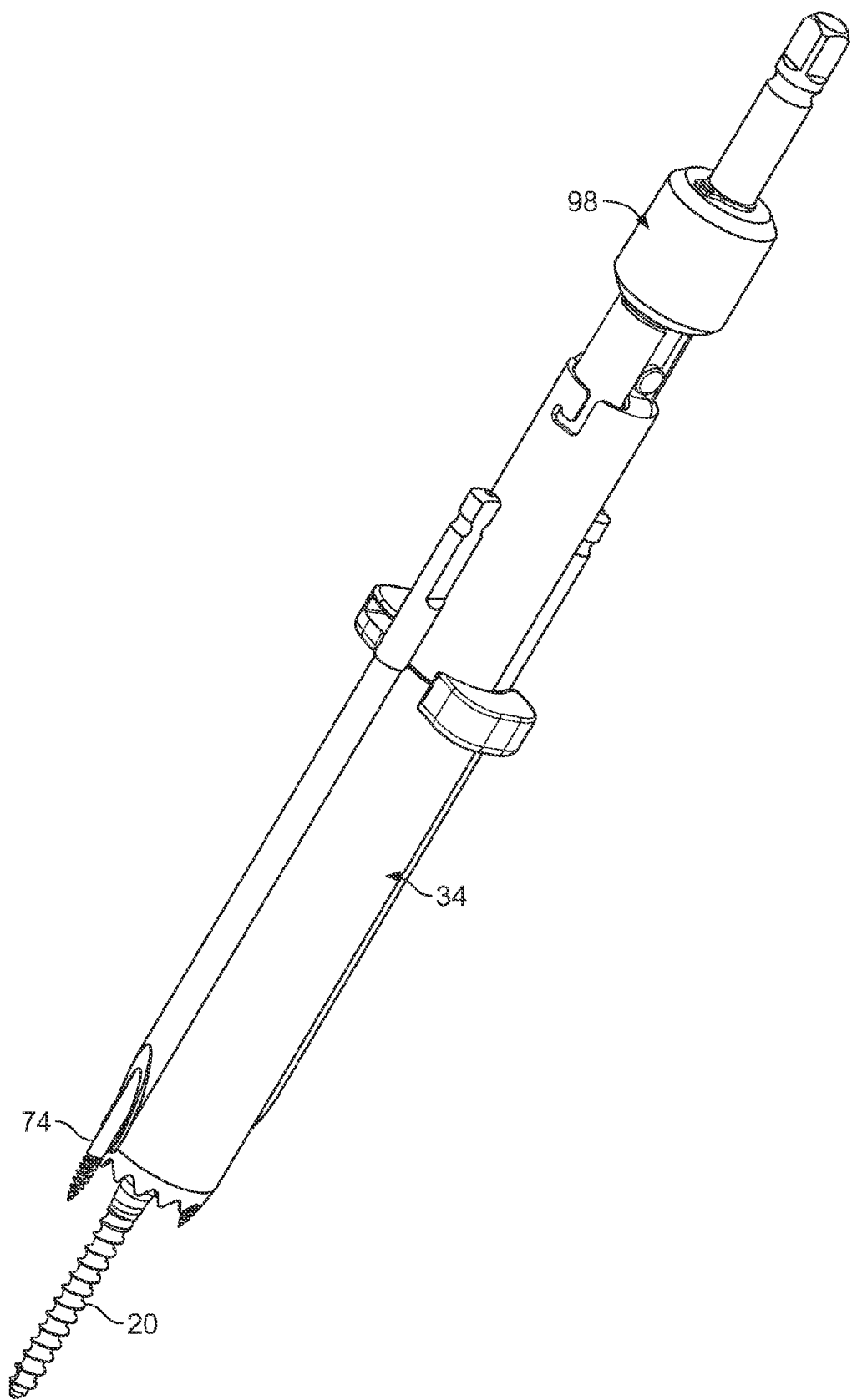
FIG. 28 is a perspective view of an assembly of the anchor, docking sleeve with fasteners; yoke manipulator; and screw driver.

As mentioned above, the assembly shown in FIG. 28 is moved down the docking sleeve 34 until the tip of the bone anchor 20 falls into the pilot hole. The surgeon rotates the assembly by the drive handle until the anchor 20 is fed down the pilot hole and satisfactorily inserted or driven into the bone, after which the driver 98 may be removed. This procedure may be repeated as needed to set the needed number of anchors at the required locations.

Figure 29:
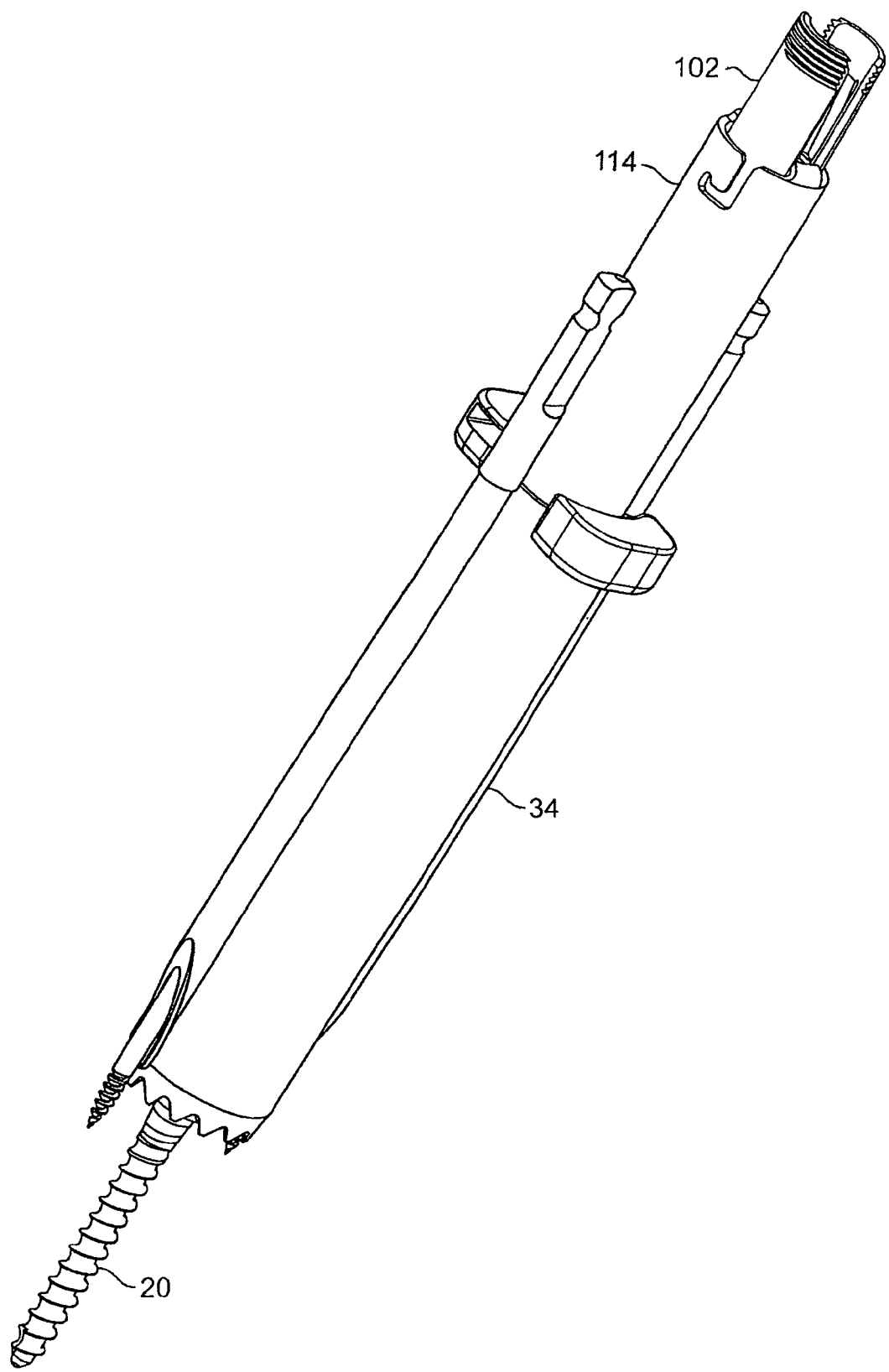
FIG. 29 is a perspective view of an assembly of the anchor, docking sleeve with fasteners; and yoke manipulator.

The assembly shown in FIG. 29 (screw inserter drive handle not shown) is moved down the docking sleeve 34 until the tip of the anchor falls into the pilot hole. The surgeon rotates the assembly by the drive handle until the anchor is fed down the pilot hole and satisfactorily inserted into the bone. The screw driver 98 may now be removed. This procedure may be repeated as needed for placement of additional anchors 20 at other locations.

Once at least two anchors 20 have been set, a connecting member or spinal rod 26 may be fed between the yokes 22. After the inserting procedure that positions the connecting member 26, detailed below, an instrument preferably operated through the yoke manipulator 102, 124 is driven to compress the closure cap 24 and connecting member 26 into the yoke 22. The connecting member 26 may be pre-bent or bent by surgery staff to the surgeon's specifications. The preferred bend of the member 26 is approximately 7 degrees. Once adequately seated, the closure cap 24 is rotated to a locked position. This process is repeated until the connecting member 26 is fully locked down.

Figure 30:
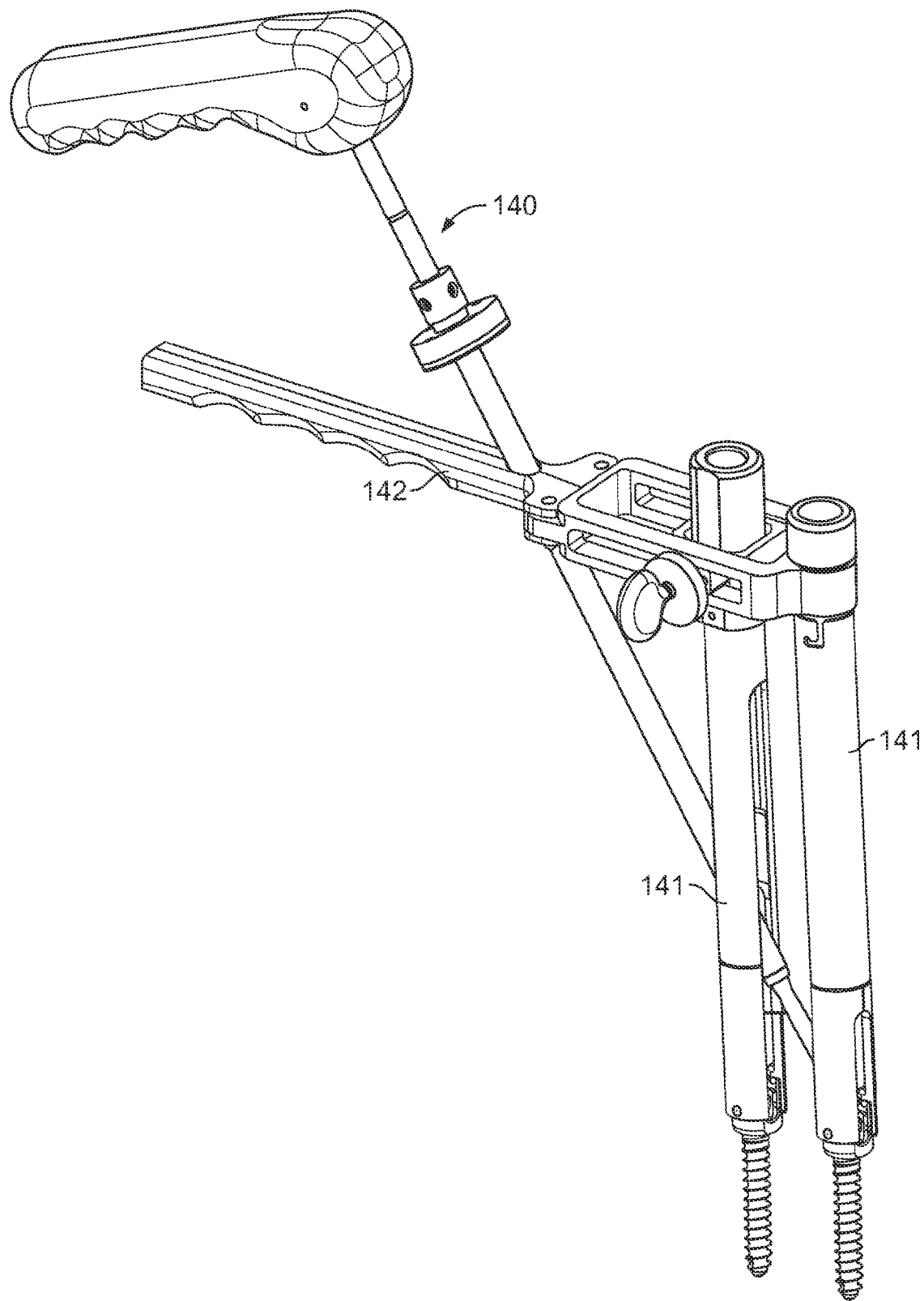
FIG. 30 is a perspective view of an MISS.

To assist in the insertion, guidance, and lockdown of the connecting rod member 26, a rod inserter 140, and a guide 142 along with the yoke manipulators assemblies 141 are employed (FIG. 30). In this embodiment, the connecting member 26 may include features that enable optimal insertion. As shown in FIG. 2, the connecting member 26 may include a nose portion 144 with a rounded, chamfered, or reduced diameter tip. The nose 144 is shaped to ease the passage of the rod through the soft tissue, the yoke manipulators, or other MISS instrumentation, and into the yoke 22. The main body portion 146 of the connecting member 26 is preferably round having a 5.5 mm constant diameter. Alternatively, the rod body 146 may have a non-circular diameter. Further, the member 26 may be straight or preferably has a pre-bent profile. To initially create a path through the tissues, a muscle splitter in a reduced diameter or profile of that of the connecting member may first be driven through the soft tissues to create a path for the connecting member 26.

The rod member 26 has an attachment end 148 used to attach, hold, or steer the member 26 into position within the yoke 22. The end 148 may have a boss 150 which may include two flat portions further having a capture 152 located therein. The capture 152 is illustrated in FIG. 2 as a hole. The capture may be a hole, bore, recess, boss, groove, or other structure that would provides a distinct point of capture for holding the connecting member 26 in the rod inserter 140. This attachment end 148 is secured to the rod inserter 140 during the insertion procedure. Further, the end 148 may include a ridge portion 151 or other structure that limits the range of movement of the connecting member 26 relative to the rod inserter 140 during insertion as will be described hereinafter.

Figure 33:
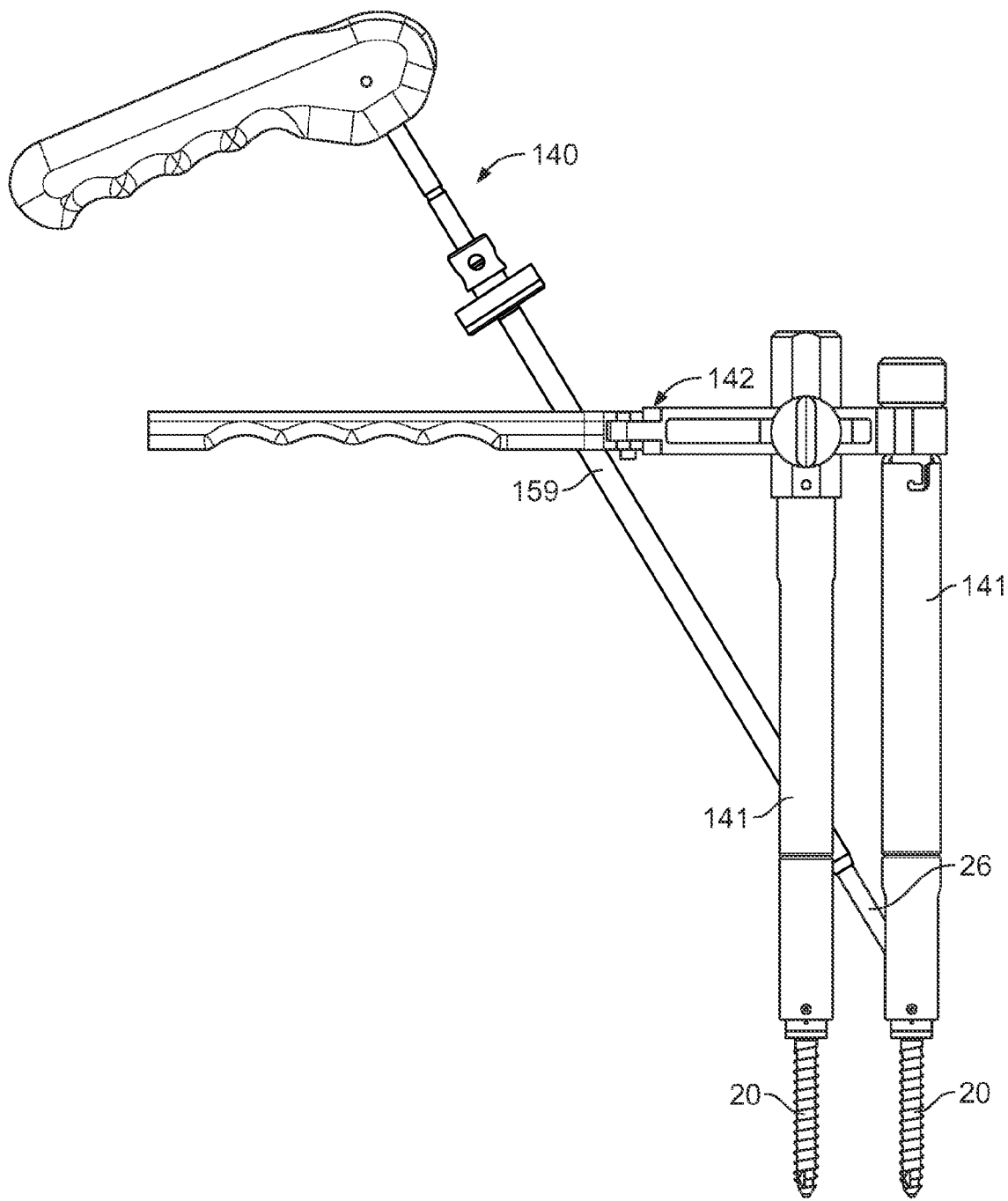
FIG. 33 is a side view of the MISS having the rod inserter in a first position.

A portion of the rod inserter 140 is fed transversally through the yoke manipulator 124 via the slot 106, as shown in FIG. 33. The manipulator assembly 141 nearest to the handle of the rod inserter 140 has the longer slot 106 since that assembly will require greater clearance because the connecting member 26 is passed into a farther, more distally positioned yoke manipulator assembly 141. Preferably the slots 106 in manipulators 102, 124 are also slightly wider than the diameter of the connecting member 26. As stated previously the positioner 116 located on the manipulators 102, 124 may cooperate to properly orient the manipulators 102, 124 and slots 106. As can be seen in FIG. 33, the cooperation between the yoke manipulators and rod inserter 140 ensures clearance of the connecting member 26 so that it can be properly seated 1L yoke 22.

Figure 31:
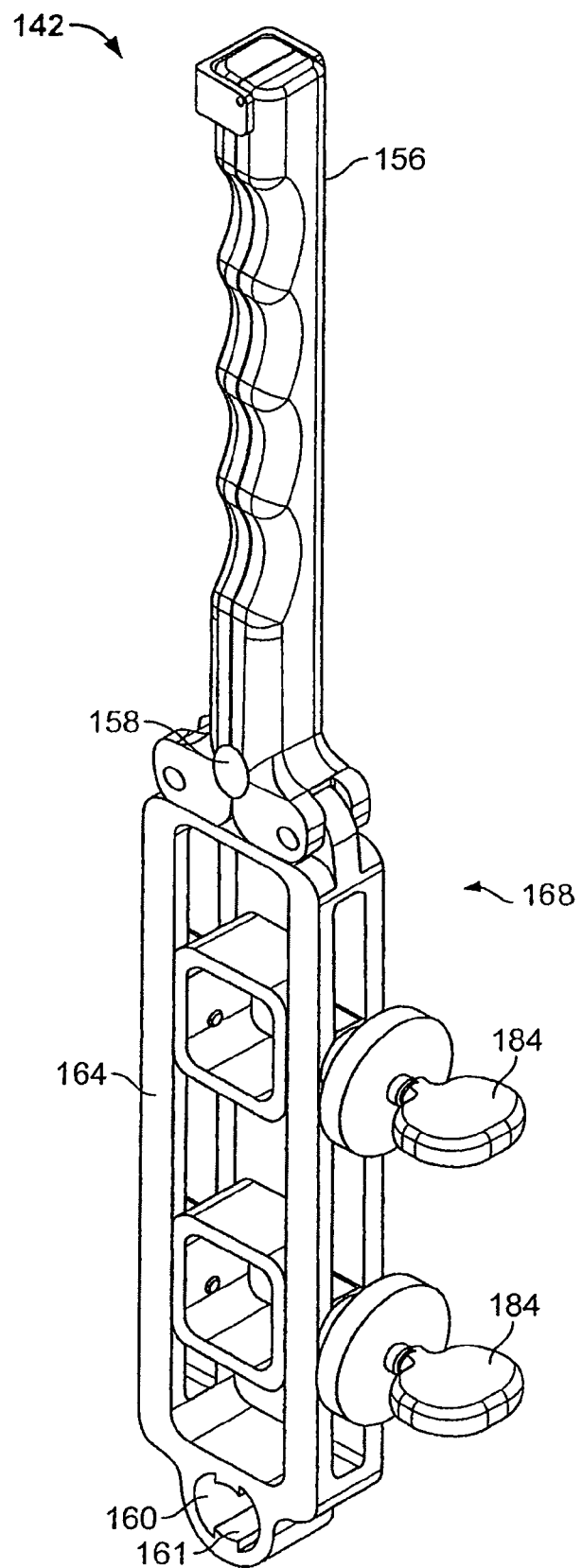
FIG. 31 is a perspective view of a guide.
Figure 32:
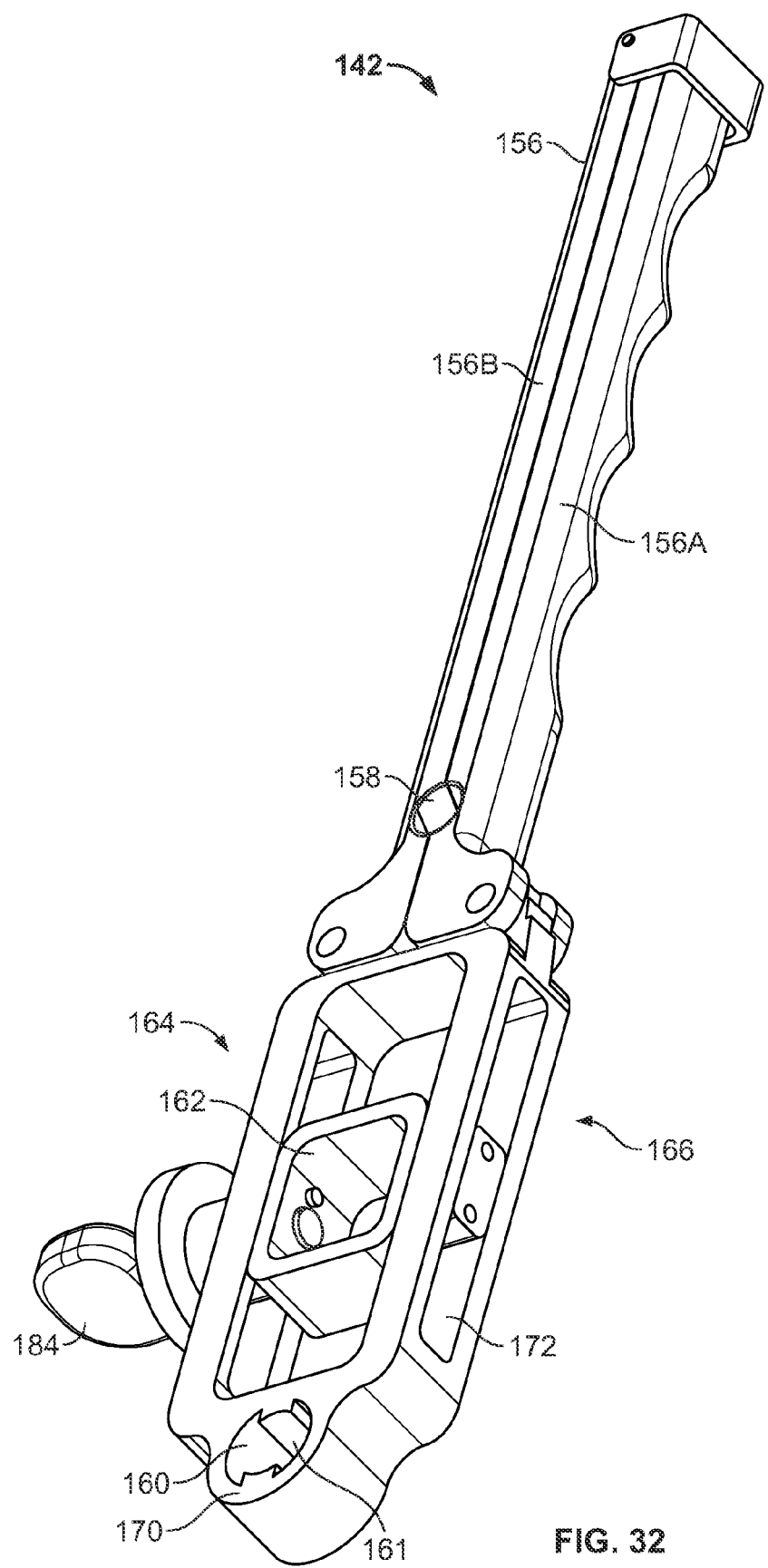
FIG. 32 is a perspective view of another embodiment of a guide.

To assist in directing the rod inserter 140 into position, a guide device 142 may be employed although the surgeon may choose to use the rod inserter 140 in the absence of the guide 142. After the manipulators are positioned inside the body as previously described, the guide 142 is attached to the manipulators 102, 124. The guide 142 moves the yoke manipulators 102, 124 generally parallel to one another for passage of the connecting member 26. The guide 142, as illustrated in FIGS. 31 and 32, may include a handle portion 156 to permit operator control over the guide 142, a rod inserter aperture 158 to permit control over the rod inserter 142, a distal holder 160 with opening 161 to permit control over the distal yoke manipulator assembly 141, a proximal holder 162 with opening 163 to permit control over the proximal yoke manipulator assembly 141, and a guide body portion 164. The handle portion 156 is preferably sized and shaped to ergonomically fit into the surgeon's hand. For example, the handle 156 may be scalloped for an improved finger grasp.

As shown in FIGS. 31 and 32, the handle portion 156 is pivotally attached to the guide body 164. The pivot elements may be a pivot pin or rivet through the handle and body, or another joint such as a hinge, or ball and socket among other options. The handle portion 156 may include two halves, A and B. When the handle portions are closed together, the rod inserter aperture 158 is formed and the shaft 159 of the rod inserter 140 can be fed through the aperture 158 and the slot 106 in the manipulators 124. This aperture is preferably circular although non-circular shapes are contemplated, such as an elongated slot, provided the opening is sized to accept the rod inserter 140. Having the aperture 158 created by pivoting halves gives the rod inserter 140 more freedom of movement. For example, after the rod inserter 140 has positioned the connecting member 26, the inserter 140 does not need to be backed out of the guide 142 through aperture 158, but instead can be more easily removed by opening up the two halves. The surgeon may not wish to employ the guide 140, but may instead use the rod inserter 140 independent of the guide 142.

FIG. 33 illustrates, how the rod inserter aperture 158 is angled along a trajectory leading toward the yoke 22. More specifically, the surface of the aperture 158 is canted as it extends through the handle portion 156 so that an axis C extending there through extends transverse or obliquely to the axes of the manipulators in which the yokes are retained or held.

The guide body 164 serves as the primary mechanical structure to which other major guide portions attach. For example, in FIG. 31, the body 164 includes a handle pod 168 for cooperation with the handle portion 156. On the distal end, the guide body 164 may include the distal holder 160 for housing the distally positioned yoke manipulator assembly 141. It is preferred that the distal holder 160 be formed to cooperate with the yoke manipulator assembly 141 for correct positioning of the connecting member 26. Further, the distal holder 160 may include one or more directional locators 170. The locators 170 are small nub projections extending in the holder opening 161 that mate with the positioner 116 on the manipulators 102, 124. The depth of the positioner 116 may be adjusted to cooperate with the directional locators 170 such that the connecting structure 120 is held in a predetermined position with respect to the guide body 164.

The guide body 164 may also house the proximal holder 162 to permit control over the proximally positioned yoke manipulator assembly 141. It is preferred that the proximal holder 162 include a groove, ridge, track, or other structure to make it positionally adjustable within the guide body 164. For example, in FIG. 32, the body 164 includes a proximator guide 172, illustrated as a groove which adjustably guides the proximal holder 162 by way of the holder guide 174, towards and away from the distal holder 160. Such an adjustment is helpful to account for the variation in spacing of boney landmarks between one patient and another thereby making the MISS useful for patients of varying sizes. The holder guide 186 in the embodiment shown in FIG. 27, is in the form of a boss but could take many forms that complement the proximator guide 172 for the function of guiding the proximal opening yoke within the body 164.

More particularly, the guide body 164 includes a pair of generally parallel rail portions 166 extending along either side of the main opening 169 formed in the body 164. The rail portions 166 each have elongate slots 171 formed therein, and the proximal holder 162 has a generally square configuration with side walls 173 adjacent the rails 166. The sidewalls 173 have a slide member 175 attached thereto, sized to fit in the slots for sliding therein. To fix the adjustable, proximal holder 162 in the guide body opening 169, a releasable lock 184 such as in the form of a threaded nut is utilized, as will be described more fully herein after.

Figure 34:
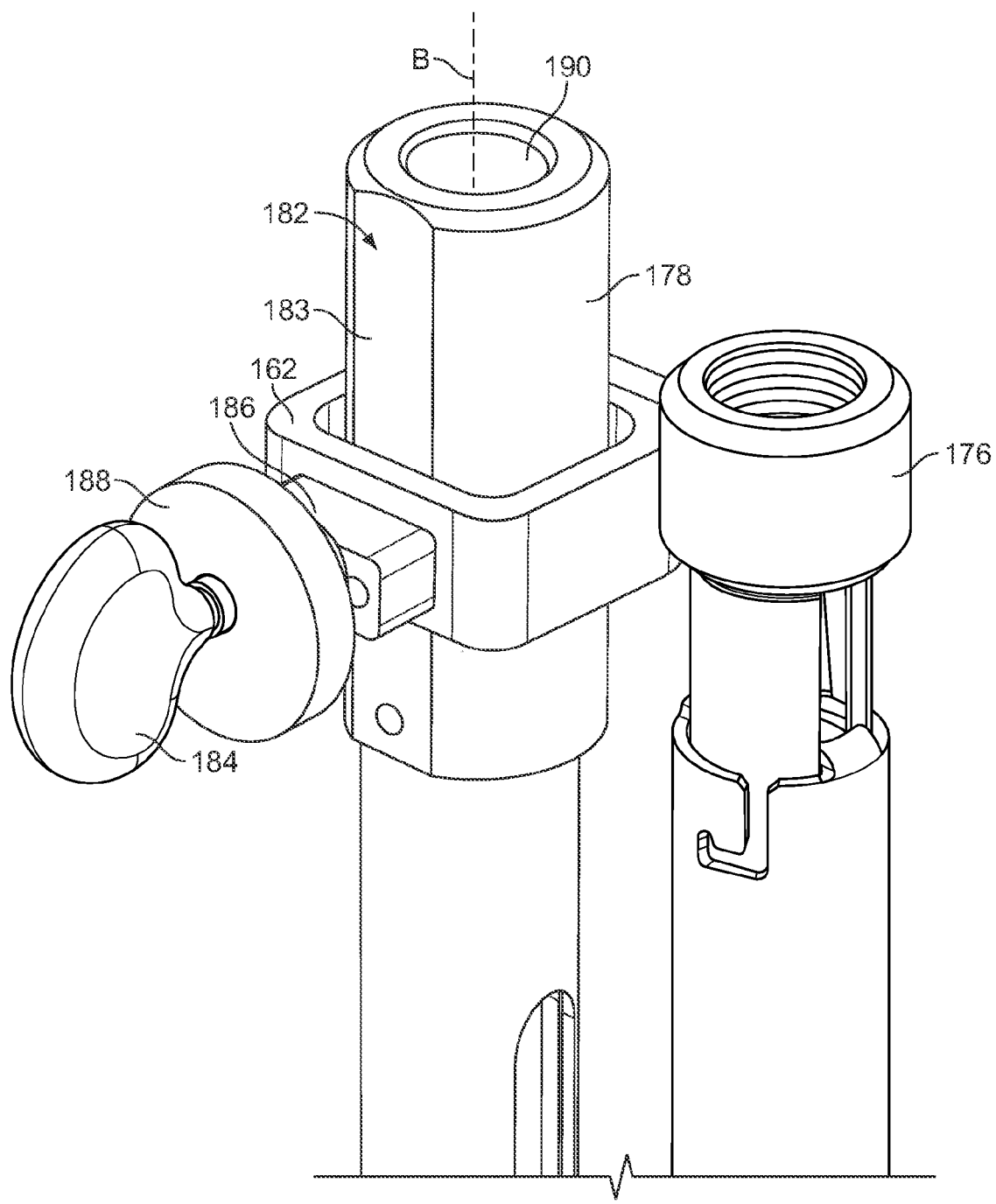
FIG. 34 is an enlarged perspective view of portions of the guide attached to the yoke manipulator.
Figure 35:
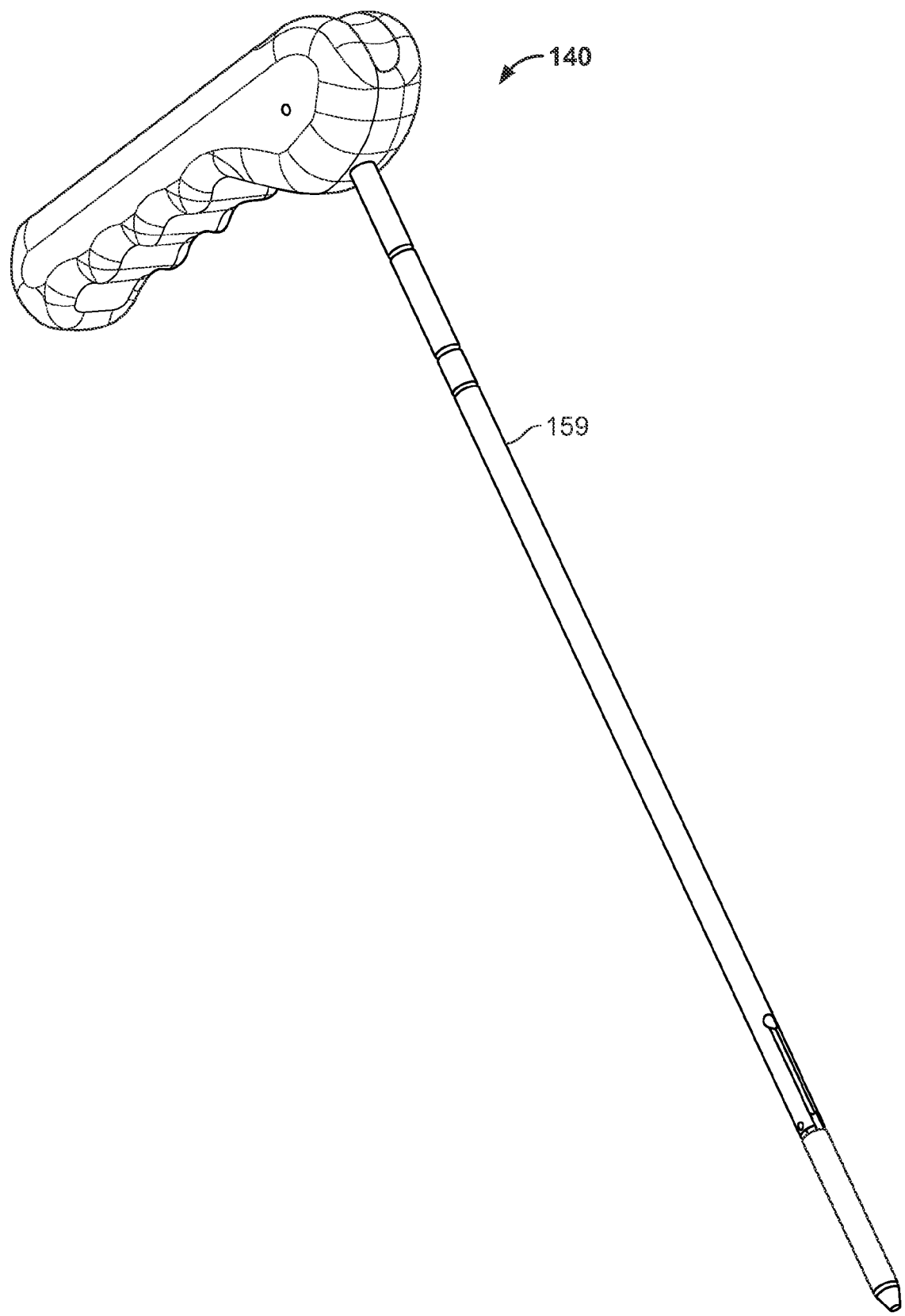
FIG. 35 is a perspective view of the rod inserter with an attached connecting member with the locking sleeve removed.

The proximal end of the yoke manipulator assembly 141, include a locking cap 176 or guide cap 178. The locking cap 176 is a structure intended for securing the yoke manipulator assembly 141 within the distal holder 160. For example, as shown in FIG. 34, the locking cap 176 may be in the form of a threaded nut mating with complementary connecting structure 120, which is illustrated as external threads at the proximal end of the manipulator. Alternatively, other connections may be used such as a bayonet connection, a set screw, or a ball detent.

The guide cap 178 may also use these alternative connections, however the bayonet style connection is preferred. A locator boss 180 formed or fixed within the guide cap 178 may serve to position, with respect to the yoke manipulator assembly 141, and hold the guide cap 178 within the retraction structure when applied in a push and twist manner.

As illustrated, the guide cap 178 and long slot manipulator bayonet attachment includes a J-shaped slot at the promixal end of the outer shaft or restraint 114 of the manipulator in which the boss 180 is linearly advanced before bottoming out. Thereafter, the cap 178 is turned so that the cap 178 cannot be pulled axially of the manipulator absent rotation thereof in the opposite direction. The cap 178 may have a bayonet attachment, a lock press fit, among others. Further, the cap 178 has tabs on the inside to resist torque. The cap 178 may include a positioner portion 182 serving to position the guide cap 178, and thus the yoke manipulator assembly 141, within the proximal holder 162 such that the slot 106 in the yoke manipulator assembly 141 is properly oriented for passage of the connecting rod 26. In the embodiment shown in FIG. 27, the positioner portion 182 is in the form of a flat surface 183 on the guide cap 178 thereby permitting fit of the guide cap 178 in only a predetermined orientation within the proximal holder 162. The positioner 182 could also be in the form of a boss, ridge, groove, or other structure to maintain positional orientation. It is preferred that the positioner 182 is formed to also permit the guide cap 178 to be adjustable generally along the axis B of the manipulator to again accommodate the variation in skeletal bone structure between patients. In this manner, guide cap 178 and therefore the yoke manipulator assembly 141 may be adjusted along axis B then locked in a desired position with manipulator lock 184 with respect to proximal holder 162.

The proximal holder 162 may also include a manipulator lock 184 for releasably locking the guide cap 178 or yoke manipulator assembly 141 in the proximal holder 162. This lock feature is illustrated in FIG. 34 in the form of a thumb screw, threaded into the body of the proximal holder 162, which upon rotation jams against the flat positioner 182. The guide 142 may also include a proximator lock 188 for locking the proximal holder 162 a predetermined distance from the distal holder 160. Again this distance is generally dependent on the anatomy of the patient. In this embodiment, the proximator lock 188 is in the form of a threaded nut wherein rotation of the nut on the threads of the thumbscrew will jam the nut against the guide body 164, and specifically adjacent side rail 166 thereof, to lock the proximal holder 162 in position. Alternatively, this lock 184 could be in the form of a cam, a ball detent, a spring pin, or other structure to lock the proximal holder 162 at a desired location within the opening 169 of the body 164. It is preferred that the proximal holder 162 is not permitted to pivot. For example, the holder guide 186 has a rectangular or block shape to prevent rotation when seated within the proximator guide 172. Both the locking cap 176 and the guide cap 178 preferably have an open center useful as a viewport 190 to permit the user to look down the yoke manipulator 102, 124 and view the connecting rod 26 entering the yoke 22 during operation.

Figure 40:
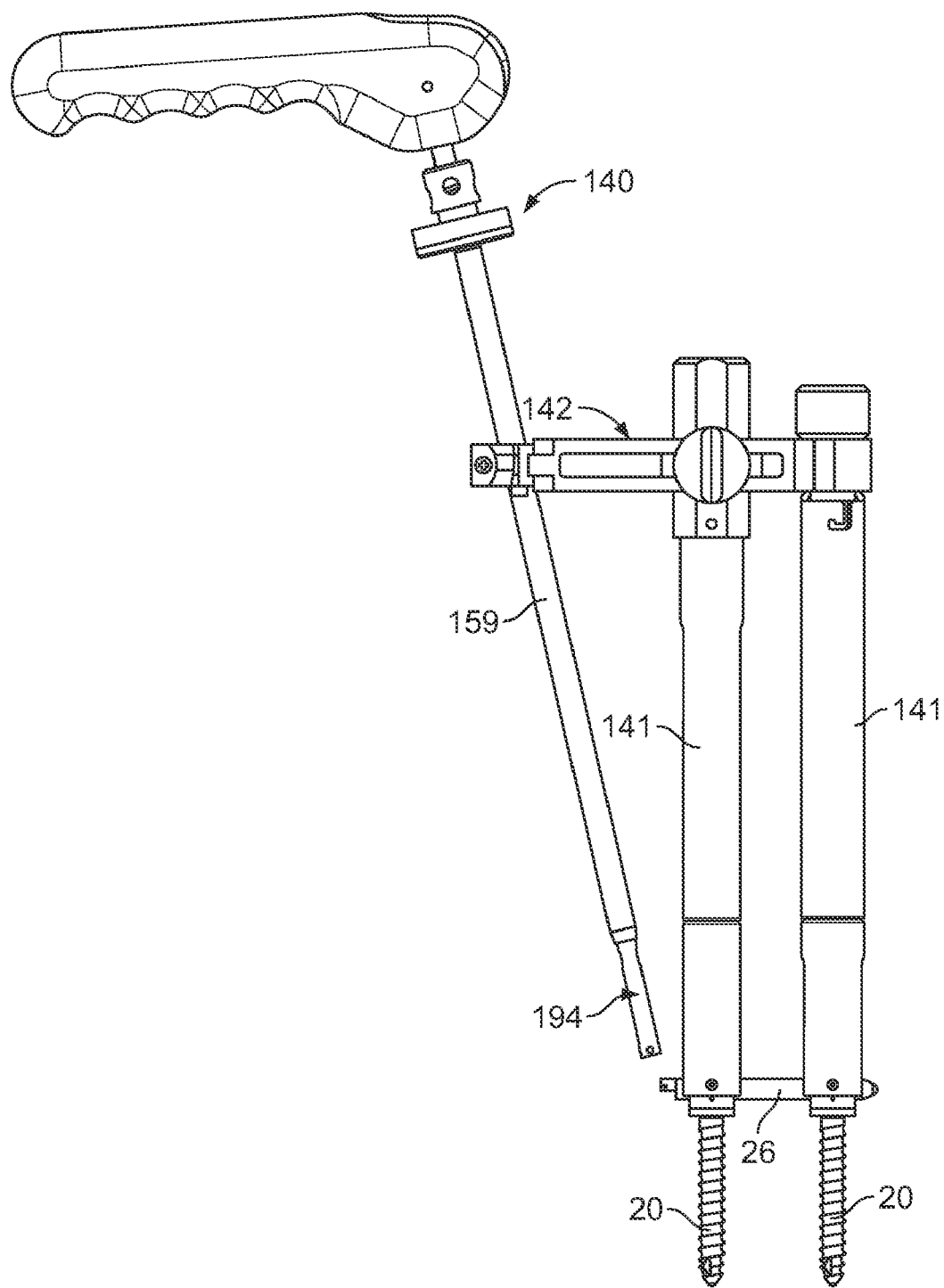
FIG. 40 is a side view of the MISS having a rod inserter in a third position.
Figure 41:
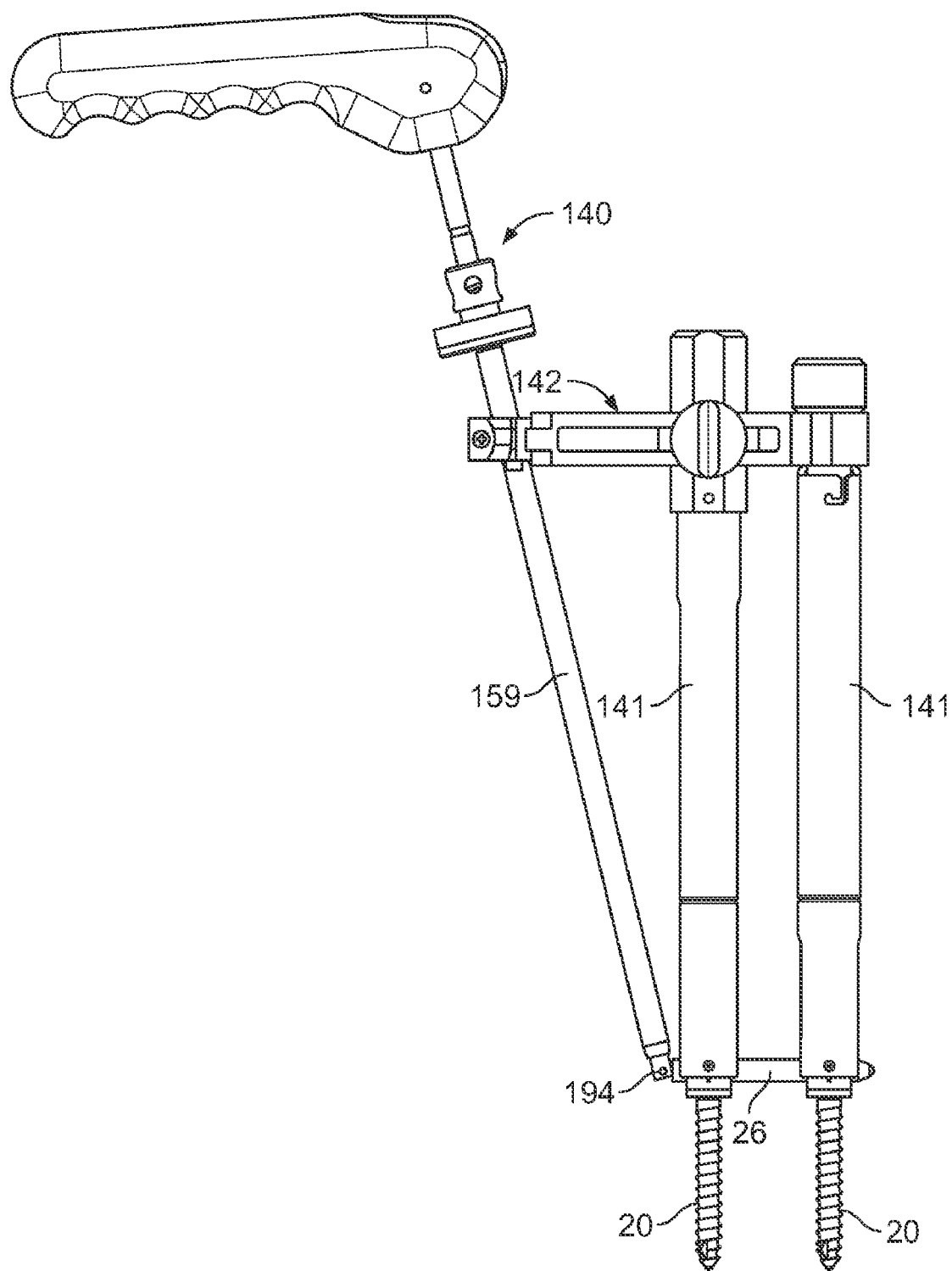
FIG. 41 is a side view of the MISS having a rod inserter in a second position.

A preferred embodiment of the rod inserter 140 is illustrated in FIGS. 33, 40, and 41. The rod inserter 140 functions to hold and guide the connecting rod 26 into a predetermined position within the yoke 22 of the pedicle screw implant assembly. The inserter 140 may include a clamping bar portion 192 having a deflectable clamp arm portion 194 at its distal end for grasping of the connecting member 26. The clamp 194 may be comprised of two or more clamp arms 196 formed by a cut or slot at the distal end of the clamping bar 192. Each clamp arm 196 may include one or more clamp bosses 198 to mate within the control capture 152 of the connecting rod 26. The clamp arms 196 are preferably spaced by a sufficient distance for acceptance of the control boss 150 on the connecting rod 26. The clamp slot is preferably of adequate length wherein the clamp arms 196 are flexible. In this manner, the end boss 150 of the connecting rod 26 may be cammed or otherwise fit between the arms and clamp bosses 198 thereof until the bosses 150 are aligned and received in the control capture 152 in the form of recesses or openings in the end thereof.

The proximal end of the clamping bar 192 is fixed within the handle by a fixation pin, however use of a compression fit, bonding or other adhesives, screw threads or other fixation methods are acceptable. The handle 157 is preferably mounted generally perpendicular to the clamping bar 192 and is preferably sized and shaped for control by an operator's hand.

Figure 36:
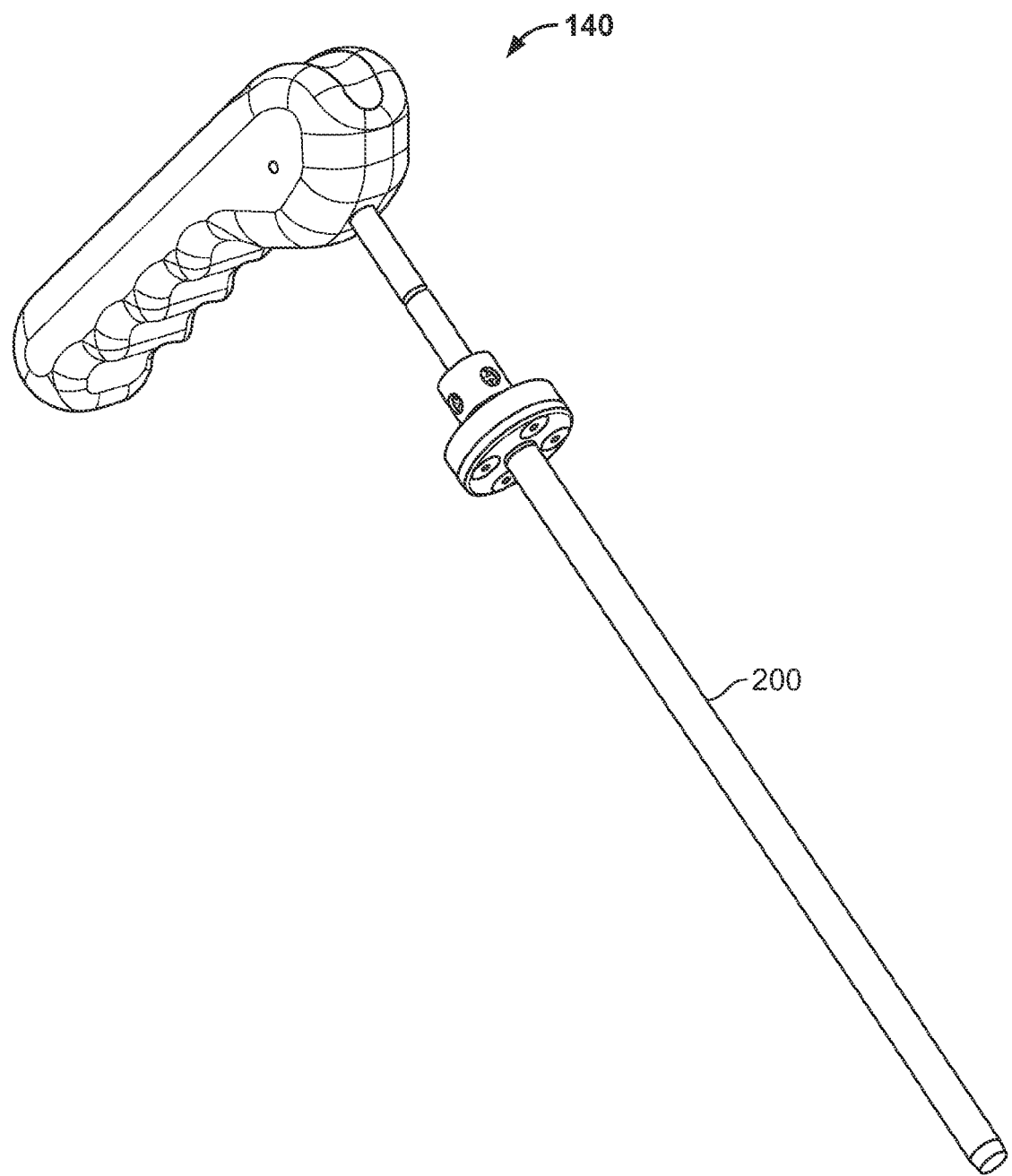
FIG. 36 is a perspective view of the rod inserter.
Figure 37:
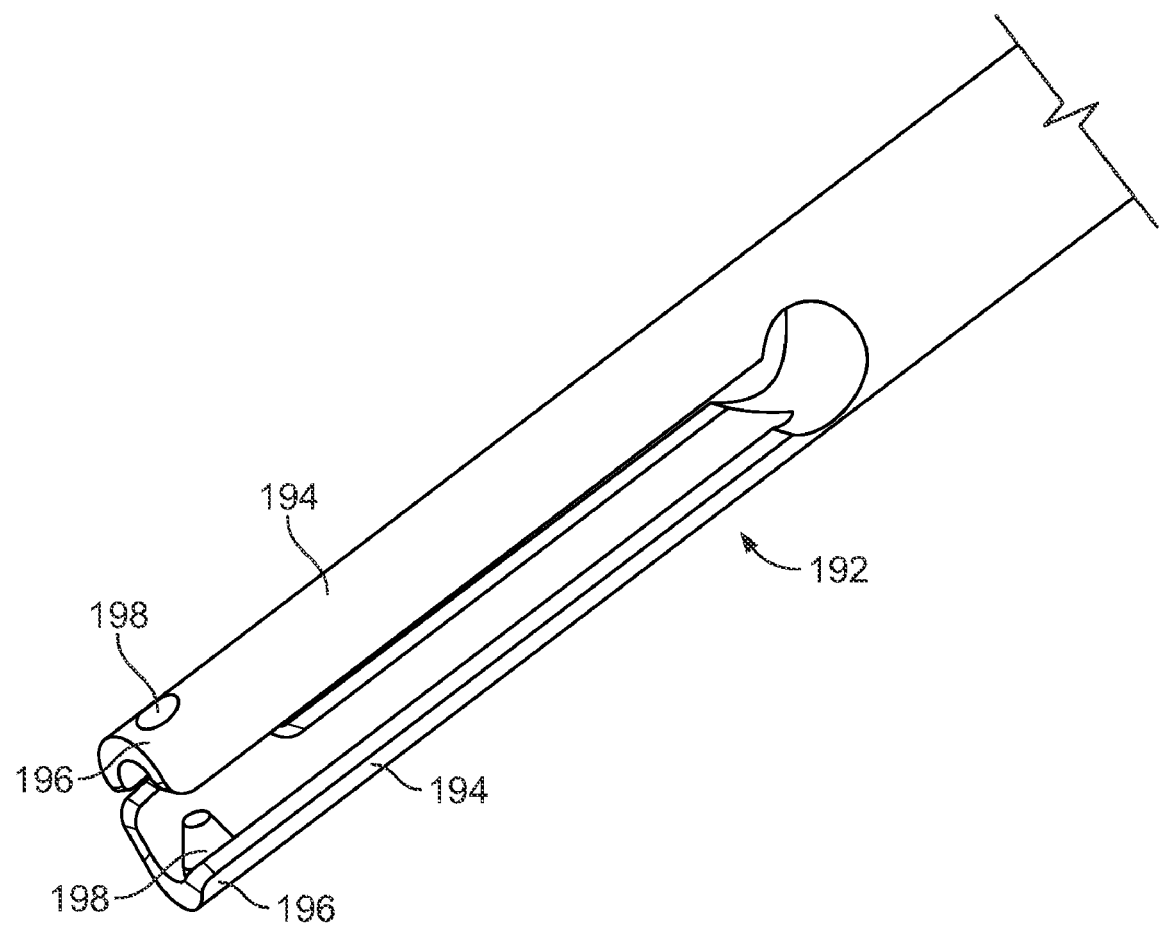
FIG. 37 is an enlarged view of the rod inserter clamp.
Figure 38:
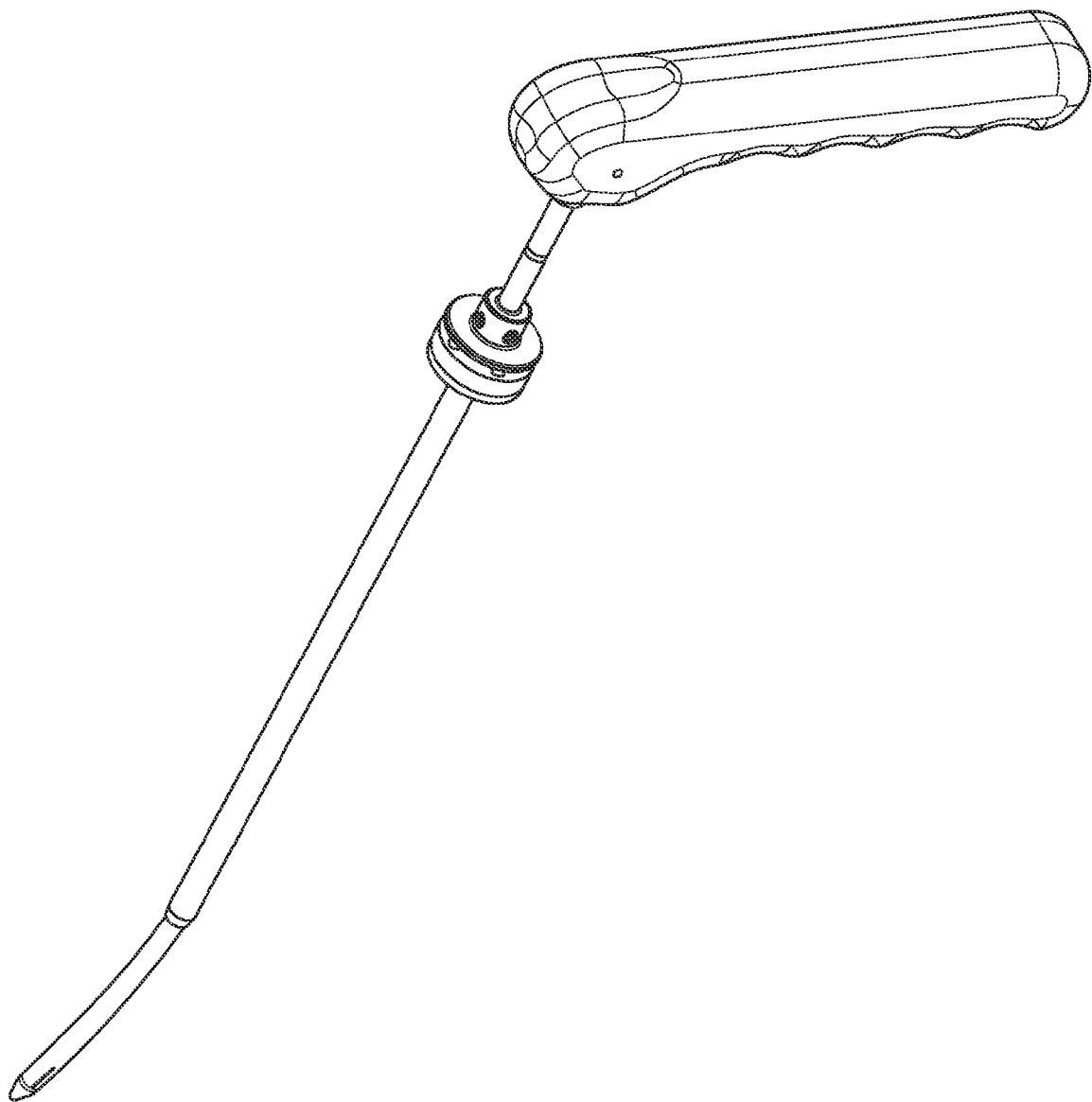
FIG. 38 is a perspective view of another embodiment of the rod inserter having a bent connecting member attached to the inserter clamp.

FIG. 36 illustrates a rod inserter 140 with a locking sleeve 200 and a positional lock 202 removed and the connecting rod 26 held within the clamp 194. The clamping bar 192 may include positional recess 204 which works in conjunction with the positional lock 202. The positional lock 202 may be in the form of a ball detent mechanism as shown in FIG. 39, a radial spring, a boss in groove, or other mechanism which provides releasable positioning of the locking sleeve 200 on the clamping bar 192.

It is preferred that the positional lock 202 defines three locking sleeve positions. In this regard, the lock 202 is connected with the sleeve, as described hereinafter. The three locking sleeve positions correlate to different insertion positions or orientations of the connecting rod 26. In "position 1" the connecting member 26 is firmly grasped within the clamp 194, such that the member 26 cannot move independent of the inserter 140. In "position 2" the connecting member is grasped in the clamp 194 such that the member 26 can pivot with respect to the inserter 140. In "position 3" the clamp 194 releases the connecting member 26.

In the present embodiment, when the positional lock 202 is in a positional recess 204a nearest the handle, "position 3" (FIG. 40), the locking sleeve annulus is positioned behind or clear of the clamp 194 wherein the clamp arms 196 are free to deflect and the connecting rod 26 is free to be inserted or released from the clamp arms 196. When the positional lock 202 is in the middle positional recess 204b, "position 2" (FIG. 41), the locking sleeve annulus is positioned partially over the clamp arms 196 thereby locking the connecting rod 26 within the arms 196 yet permitting the connecting rod 26 to pivot about the clamp bosses 198 in a range allowed by stops such as the control ridge 154. In position 2, the connecting member 26 is able to angulate 90 degrees up from collinear of the inserter 140 and specifically the bar thereof, but cannot angulate down. When the positional lock 202 is in the distal positional recess 204c, "position 1" (FIG. 33), the locking sleeve annulus is positioned over the clamp 194 and partially over the rod body 146 so that the connecting rod 26 is held within and generally in line with the axis of the locking sleeve 200.

Figure 39:
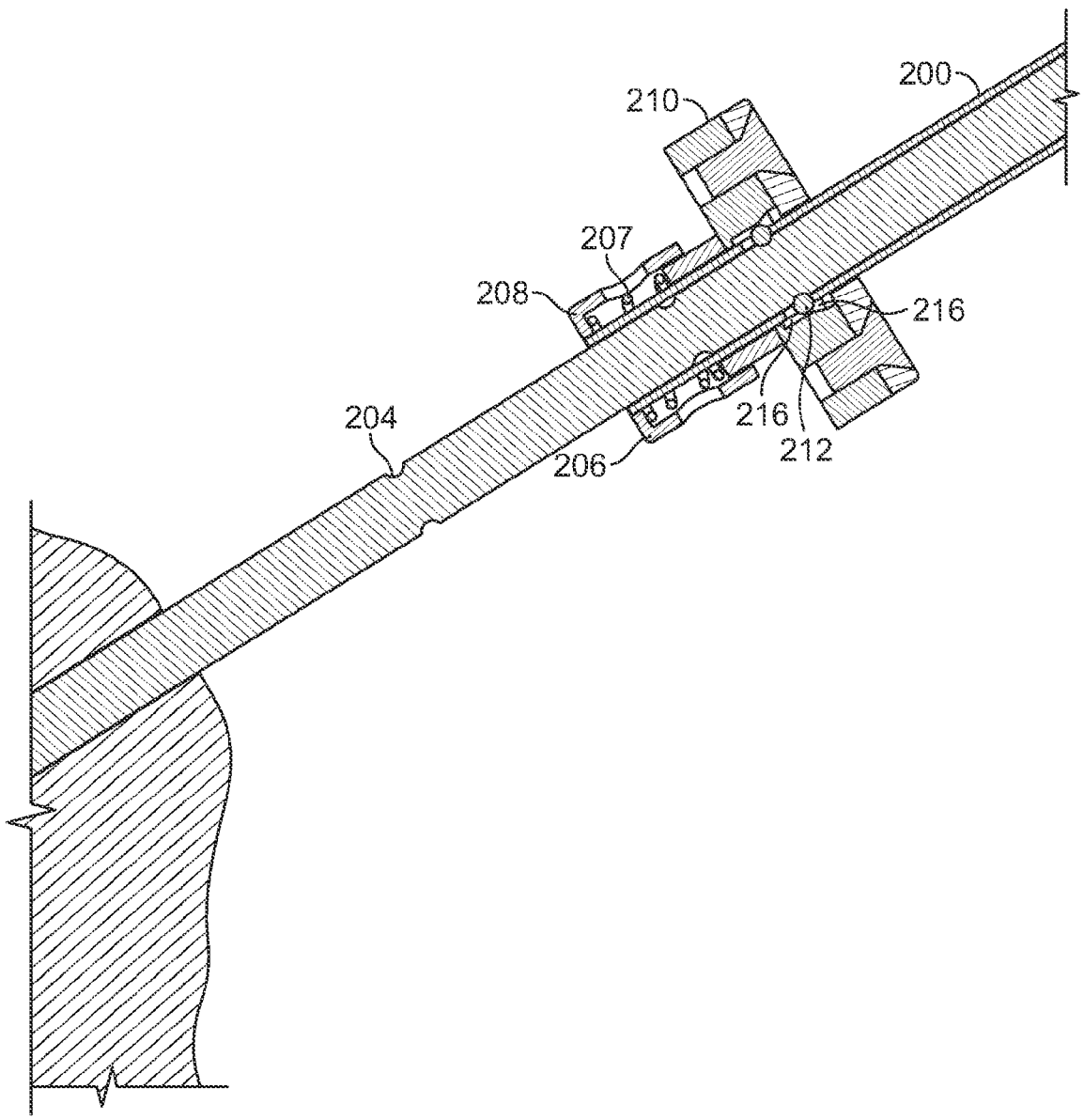
FIG. 39 is a cross section view of a positional lock shown in FIG. 36.

In FIG. 39, a ball detent version of the positional lock 202 is illustrated in a cross-sectional view. Integral to the locking sleeve 200 is a near collar 206 which houses a biasing member 208 and which compresses against a far collar 210 slidingly mounted on locking sleeve 200. Within the far collar 210 is one or more detent balls 212, riding in holes or recesses 214 within the locking sleeve 200, and which ride on the clamping bar 192. As the biasing member 208 pushes against the far collar 210, a lock ridge 216 compresses or pushes the detent ball 212 radially in the positional recess 204 therein locking the locking sleeve 200 in place. When the user overcomes the biasing member 208 by pressing together the near collar 206 and the far collar 210, the detent balls are able to ride in the unlock ridge 218 thereby falling out of the positional recess 204 and enabling the locking sleeve 200 to be slid to a different positional recess 204. The clamping bar or locking sleeve may include stops, in the form of bosses, ridges, c-clips, or setscrews for example, to limit the range of movement of the locking sleeve 200 to the desired positional recess 204.

As illustrated, the sleeve 200 extends down along the clamping bar 192 from the upper collar 206 down through the lower collar 210 which can slide thereon. The coils 207 of the spring biasing member 208 extend about the bar out from the upper collar 206 with the spring 208 connected to the lower collar 210 at the lower end of the spring 208. The lock ridge is a recess annular surface of a diameter slightly larger than that of the clamping bar 192 and extending generally axially and parallel relative to the outer surface thereof. The detent balls of a diameter that is larger than the gap between the annular surface and the bar surface so that the detent balls are normally urged into the locking recesses or annular grooves 204 formed along the clamp bar 192.

Below the lock ridge annular surface, the unlock ridge tapers away from the clamp bar as can be seen in FIG. 39. Accordingly, when the surgeon wishes to shift the lock, they simply pull up the lower collar toward the upper collar against the spring bias so as to bring the tapered surface into radial alignment with the balls allowing them to shift out of the clamp bar groove in which they reside and ride up or down along the clamp bar as the surgeon shifts the lock to the desired axial position therealong.

Figure 43:
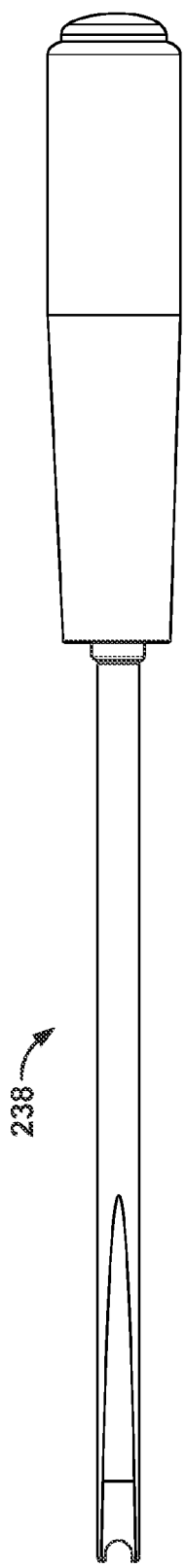
FIG. 43 is a side view of a pusher.

To assist the surgeon in positioning the connecting member 26, a pusher 238 shown in FIG. 43 may enter through the short slot yoke manipulator 102 (the distal manipulator assembly 141) to hold the rod into position as the rod inserter 140 moves the connecting member from "position 1" to "position 2." For example, by using the pusher 238 in the short slot manipulator 102 to control member rod 26, while the member rod 26 is still connected to the rod inserter 140, the surgeon has sufficient control over the rod member 26 to facilitate correct positioning. Before the sleeve 200 is moved from "position 1" the guide handles 156 may be spread open. The pusher member 238 does not lock, but instead allows the surgeon to apply force to the member 26 at the surgical site.

Figure 44A:
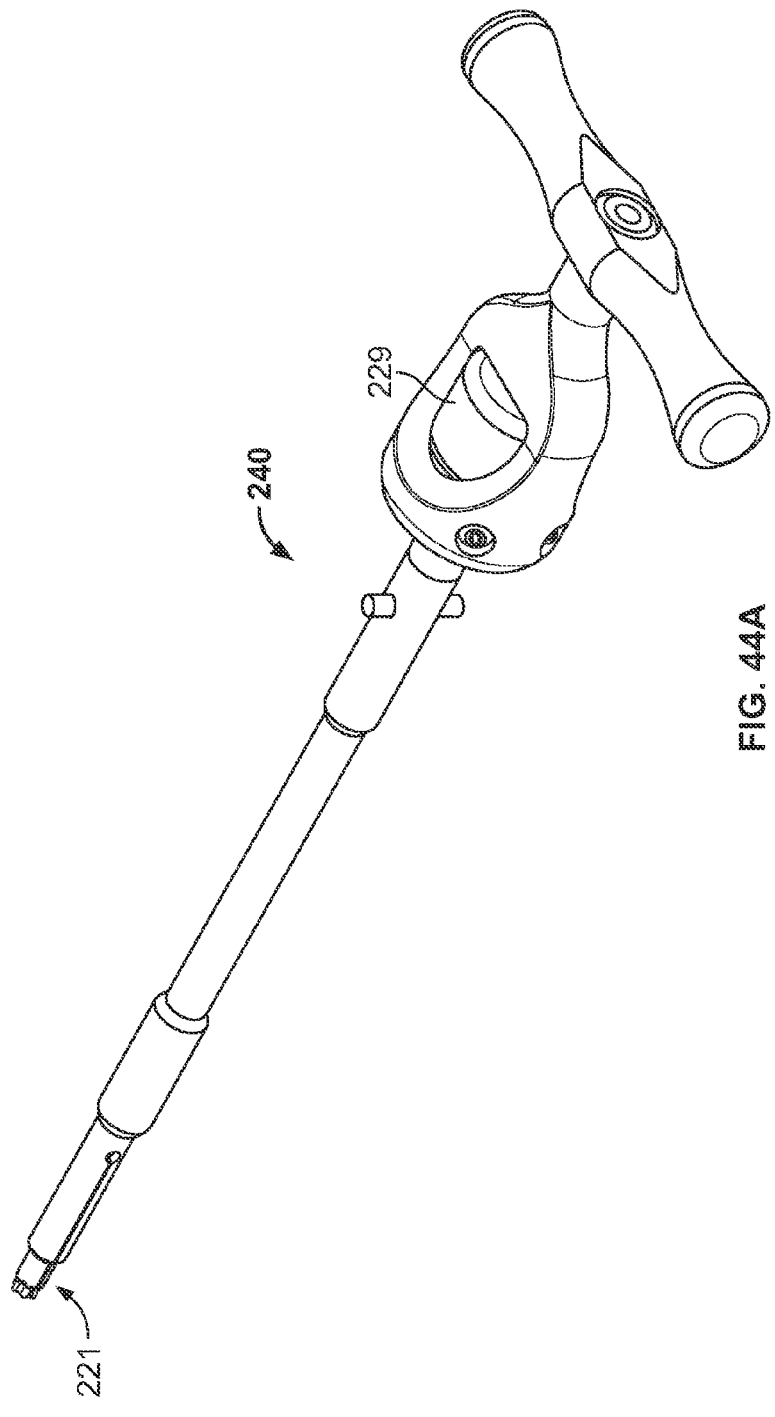
FIG. 44 A is a perspective view of a cap inserter.

Once the connecting member 26 is properly situated in the yoke 22, a cap inserter 240 may be used to rotate the cap 24 to retain the connecting member 26 in the yoke 22. One embodiment of the cap inserter 240 is shown in FIG. 44A. The cap 24 is positioned in the long slot yoke manipulator 124, and then the rod inserter 140 and guide 142 can be removed from the manipulators.

Figure 44B:
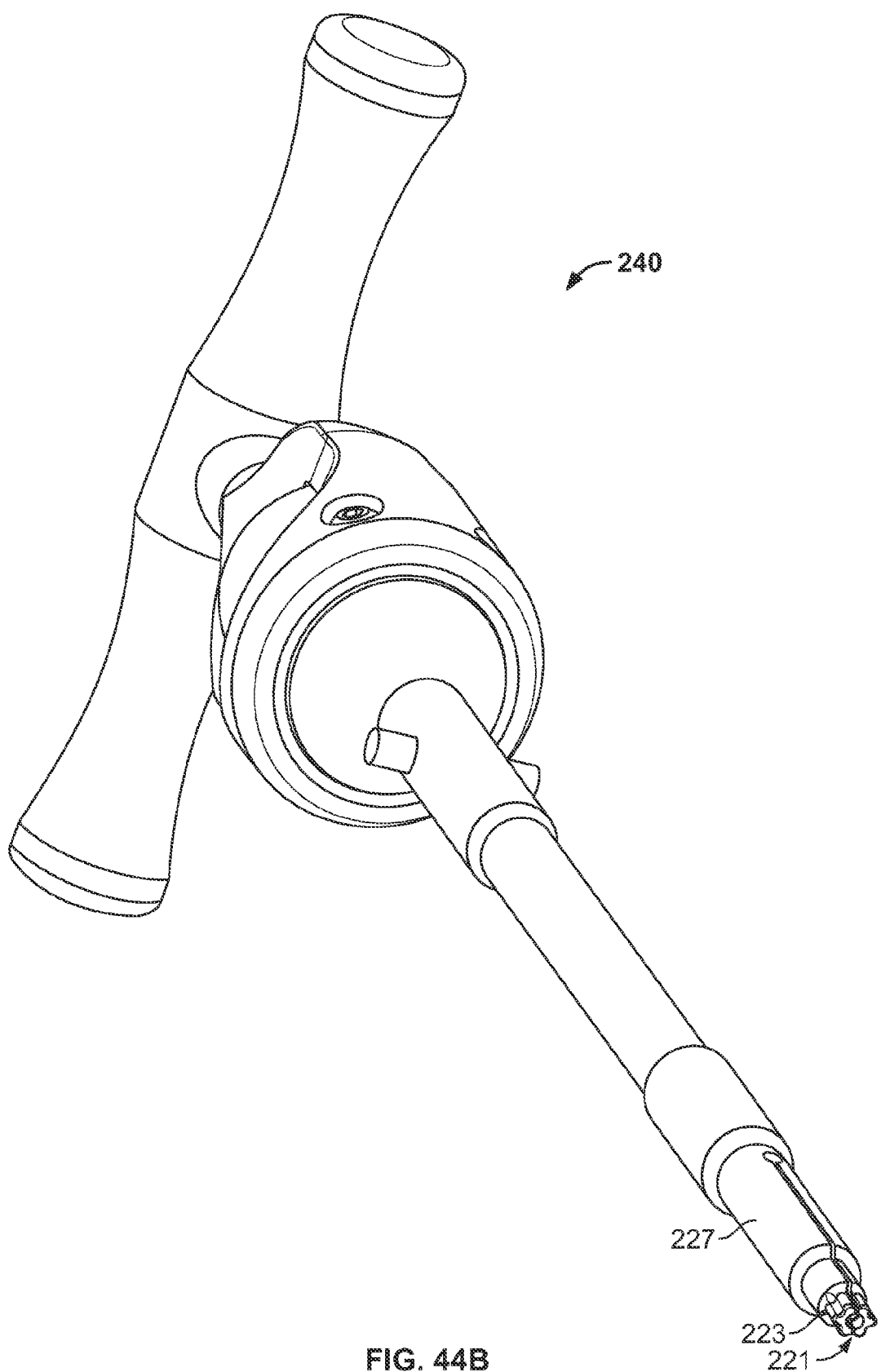

The cap 24 is placed into position using the cap inserter, FIGS. 44 A and B. To avoid accidental release of the cap 24 during the insertion procedure, instruments such as the cap inserter 240 and rod persuader 220 may include a retention mechanism 221 to releasably retain the cap 24. A retention mechanism 221 is located on the driving end of these instruments and may include a male driving portion 223 that mates with a female drive recess 225 in the cap 24. The male driving portion 223 is split into one or more flexible arms 227. A dial 229 at the handle end of the instrument 240 activates a plunger at the male driving portion 223 with the flexible arms 227 so that it can secure the cap to the instrument. To release the cap the dial 229 is derotated causing the plunger to retract wherein the flexible arms 227 can constrict and release the cap 24 as it is positioned in the yoke 22.

Figure 42:
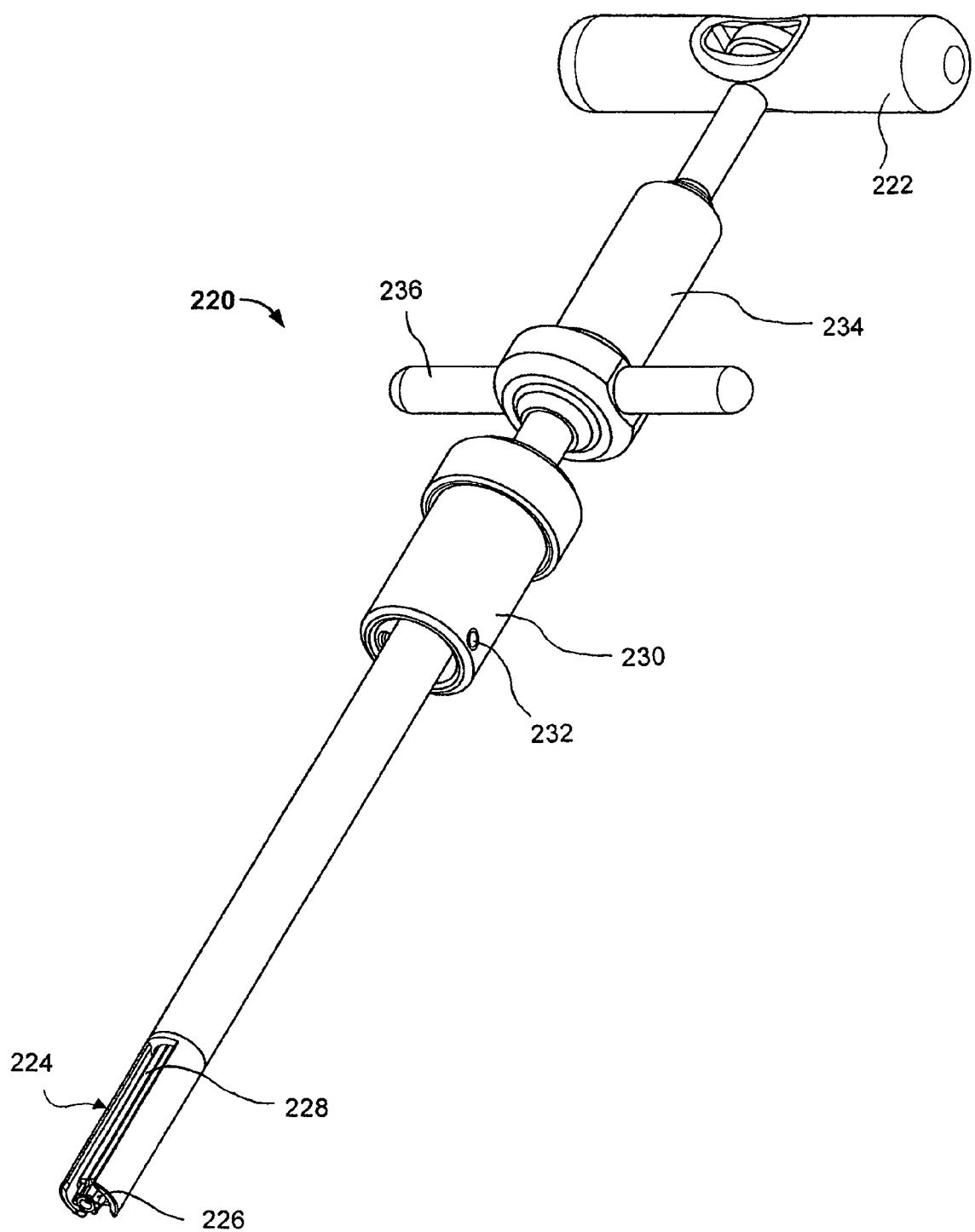
FIG. 42 is a perspective view of a rod persuader.

However, there are times when the member 26 will need to be forced into the yoke 22 in order to rotate the enclosure cap 24 thereby capturing it within the yoke 22. The MIS rod persuader 220 (FIG. 42) may be used not only to force down the rod, but also to rotate the closure cap 24. Typically, the rod persuader 220 is only used with the short slot yoke manipulator 102 when the surgeon is having difficulty positioning the connecting member 26 in the yoke 22. First, a rod driver handle 222 is derotated wherein the cap driver 226 is backed up into the window 224. The closure cap 24 is then loaded on the persuader 220 by mating the cap driver 226 within the drive surface of the closure cap 24 with the cap flanges 25 resting within the window 224. The driver rod 228 is led down the center of the yoke manipulator assembly 141 until the restraint cup 230 rests over the top of the restraint 114. The restraint cup 230 may include a lock 232 wherein a rotation of the restraint cup 230 moves the lock 232 into the retraction structure 122 to hold the persuader 220 and cap 24 within the yoke manipulator assembly 141. Other connections may be used to hold the yoke manipulator assembly 141 to the persuader 220 such as a threaded connection.

Figure 45:
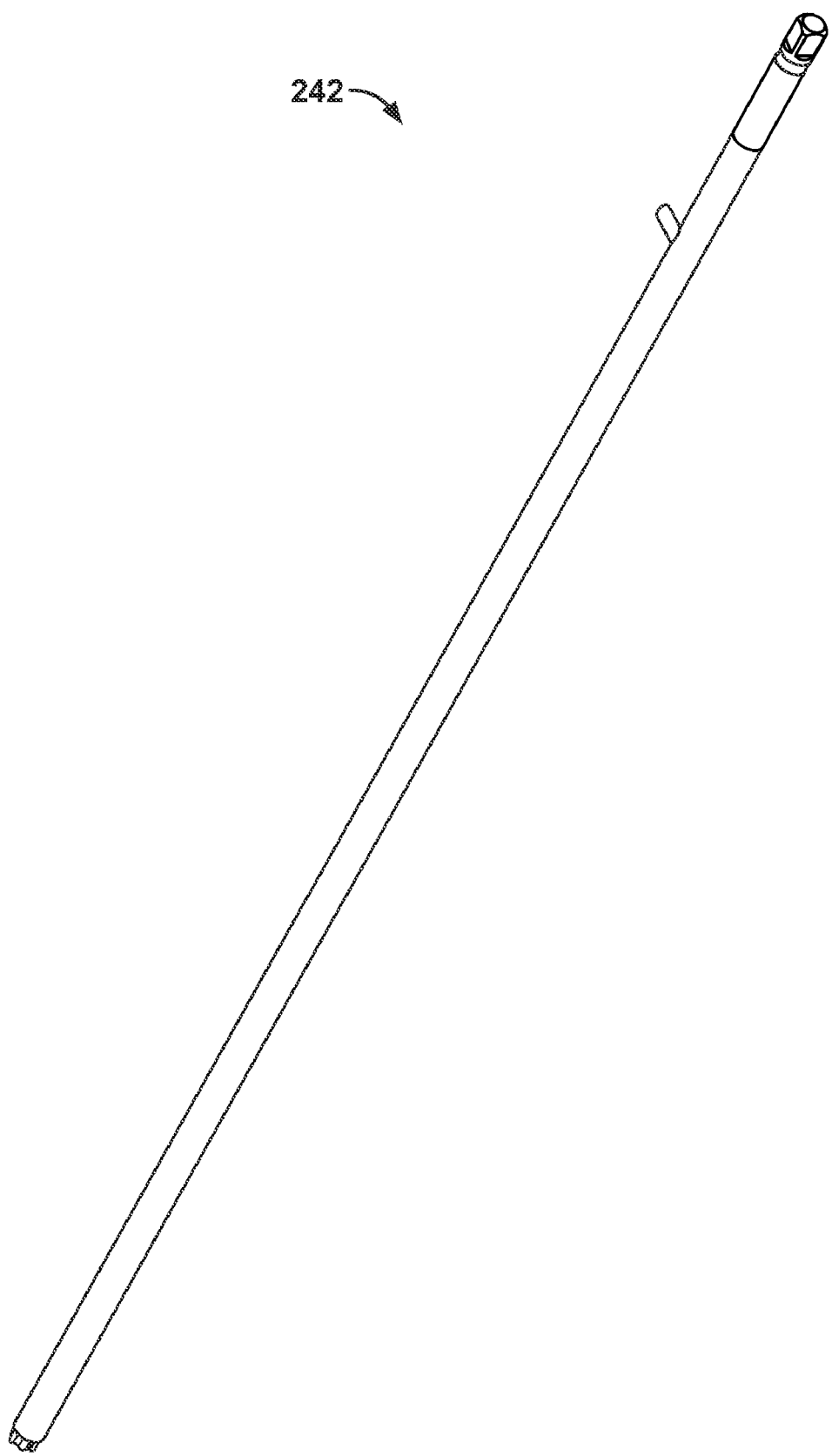
FIG. 45 is a perspective view of a final locking instrument.

The driver rod 228 maintains a threaded connection with a body 234 wherein rotation of the rod driver handle 222 will advance the driver rod 228 down through the window 224 thereby advancing the cap 24 and thus the connecting member 26 into the yoke 22 to a predetermined depth. The cap driver handle 236 is then rotated which in turn causes a rotation of the cap driver 226 and a capture of the closure cap 24 in the yoke 22. The rod driver handle 222 is then derotated to withdraw the cap driver 226 from the closure cap 24. The restraint cup 230 can then be derotated from the yoke manipulator assembly 141 for persuader removal. The persuader 220 may perform final tightening on the closure cap 24, or a final locking instrument 242 and a torque tube 254 may be used. Typically, the persuader only rotates 45 degrees and then the final locking instrument 242, shown in FIG. 45, is used to rotate the cap 24 to its final locking position. The final locking instrument 242 is generally used to finally tighten the caps in the yokes held by both the long and short slot manipulators 102, 124. Accordingly, in one approach, a first tool such as the above-described persuader 220 is used to turn a locking device, e.g. the closure cap 24, of a pedicle screw assembly to a first predetermined rotary position and a second tool, such as the above-described final locking instrument 242, is used to turn the locking device beyond the first predetermined rotary position.

Figure 46:
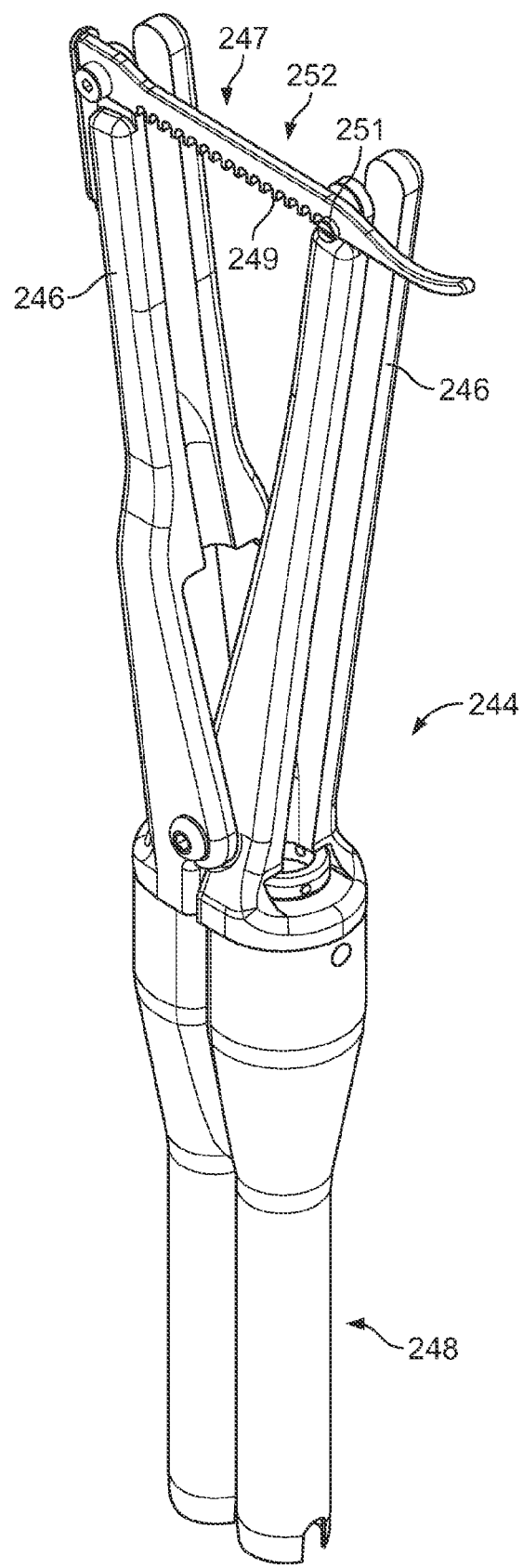
FIG. 46 is a perspective view of a compression tool with tubes attached thereto.
Figure 47:
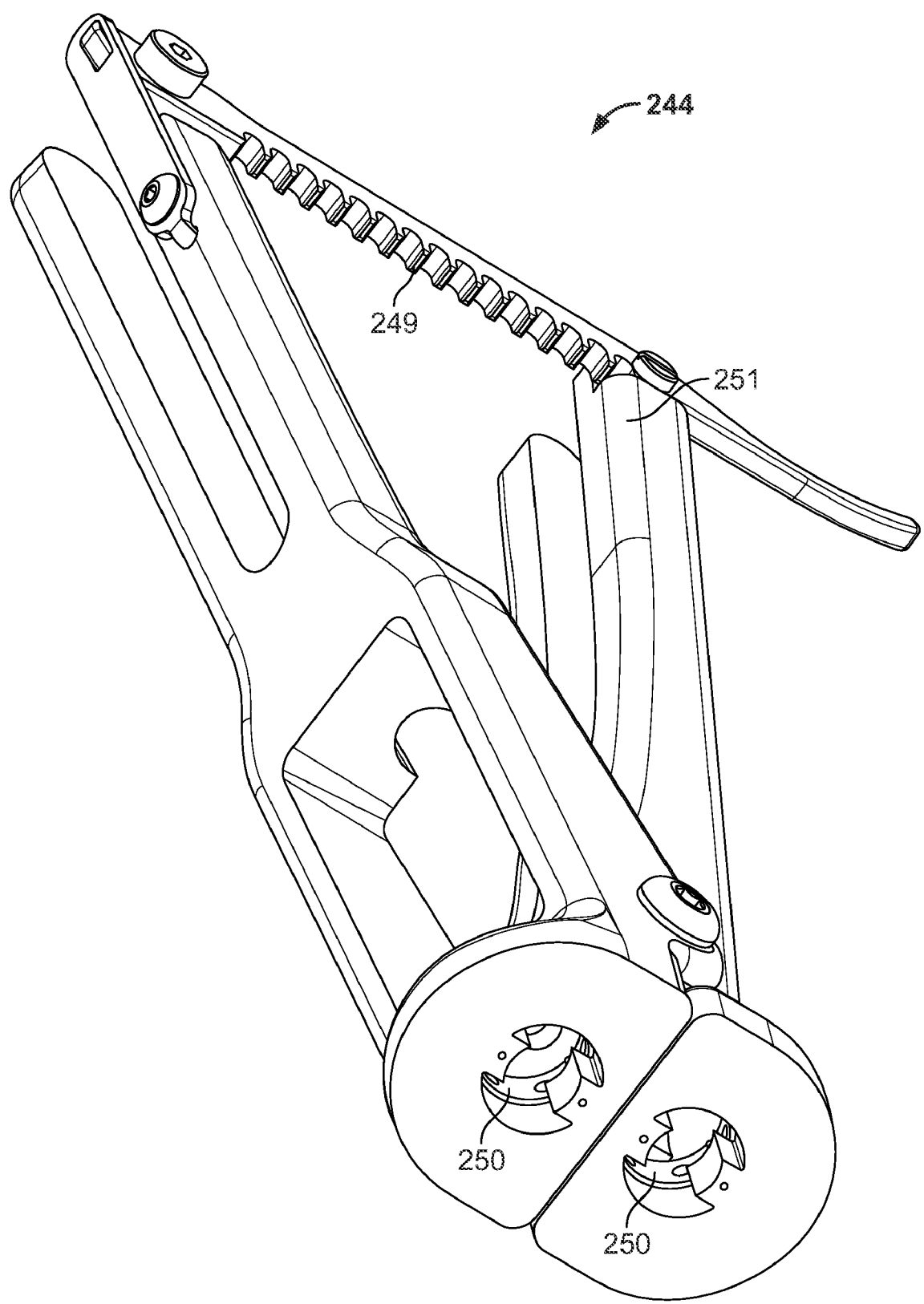
FIG. 47 is a perspective view of a compression tool without the tubes attached.
Figure 48:
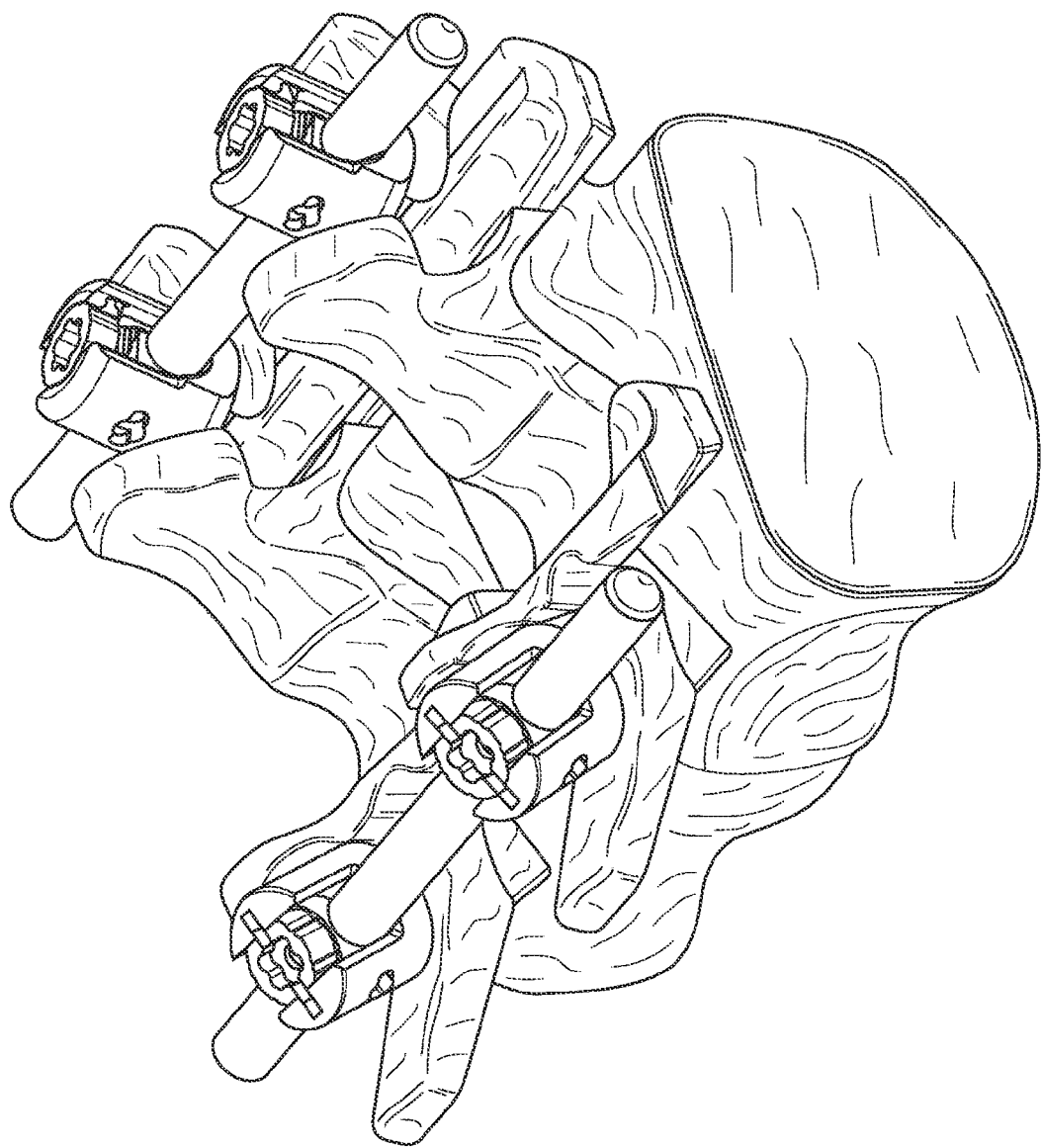
FIG. 48 is a perspective view of another embodiment of an MISS implant.
Figure 49:
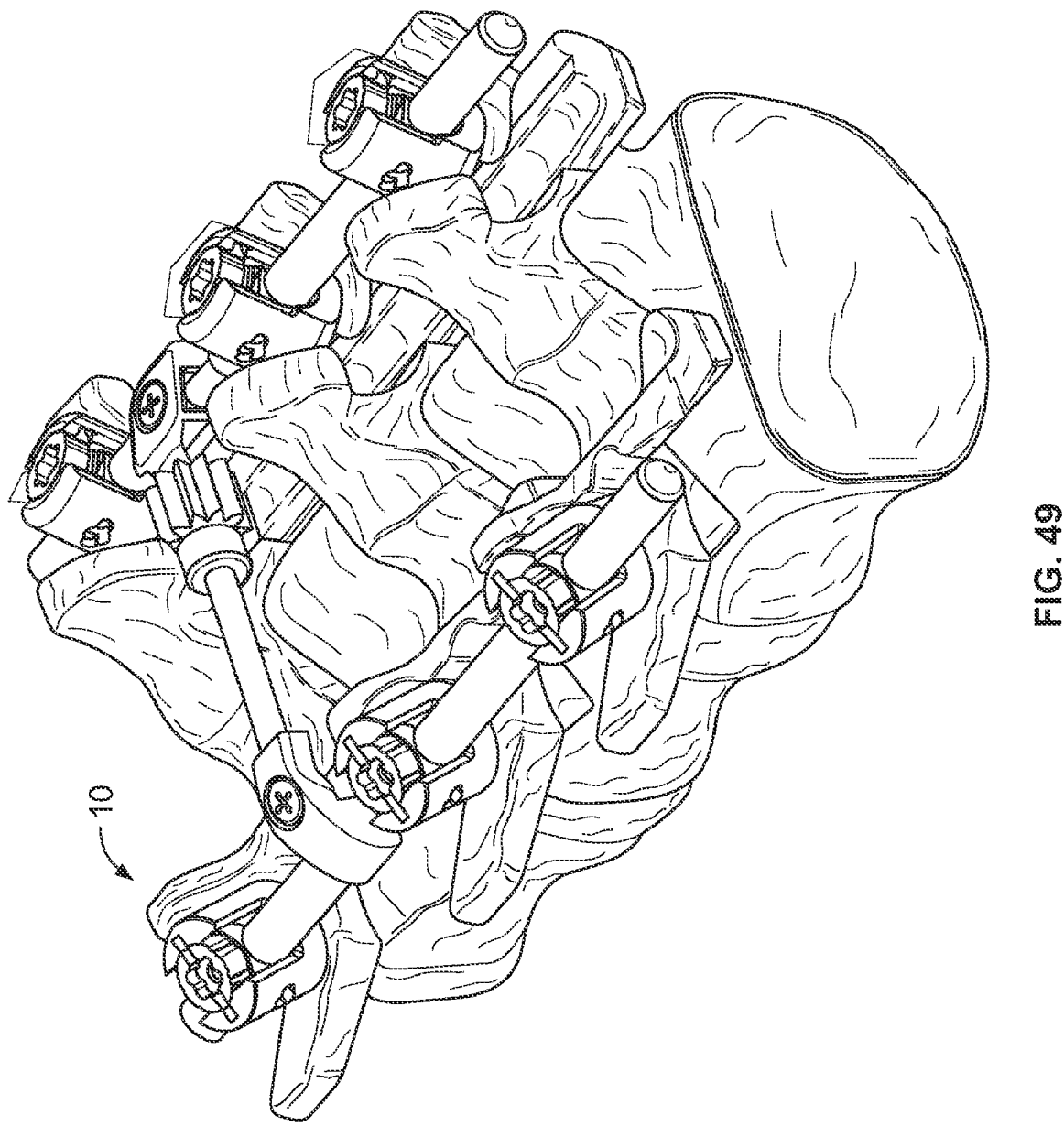
FIG. 49 is a perspective view of another embodiment of an MISS implant including a crosslink.

However, before the final locking instrument 242 fully tightens the cap 24, a compression tool 244 can be utilized to move the yoke manipulators 102, 124 and thereby the bone anchors 20 closer or further apart. As shown in FIGS. 46 and 47, The compression tool 244 has two handles 246. A pair of tubes 248 are slid over the yoke manipulators 102, 124. End apertures 250 open to the bottom transverse flange of the handles slide over the compression tubes 248. Then, by moving the handles 246, the surgeon can move the yoke manipulators 102, 124. The locking mechanism 252 located on the compressor 244 secures the compressor and the manipulators 102, 124 into position, such that the caps 24 can be finally tightened into position. Then, the final rotation is accomplished by the final locking instrument 242 as it is fed down through the tubes 248 of the compressor 244. Use of the compression tool 244 is based on patient needs and there are times when the compression instrument 244 will not be necessary.

More particularly, the handles 246 can be pivotally connected toward their lower flanged ends to provide relatively long lever arms for the compressor tool. This enables the surgeon to more easily distract or compress the adjacent vertebra in which the pedicle screw assemblies are implanted. One of the handles has a rack member 247 including spaced teeth 249, and the rack 247 is pivotally attached to its proximal end. The other handle has a projection 251 at its proximal end for fitting in a selected one the spaces between adjacent teeth. Accordingly, the rack 247 and projection 251 cooperate to form the illustrated and preferred locking mechanism 252 so that the handles can be fixed in a selected, locked position, relative to each other based on the distraction/compression needed for the surgical procedure.

After the connecting member 26 is locked into position, the manipulators 102, 124 may be released from the bone anchors 20. In one embodiment, removal of the manipulators involves removal of all unnecessary instrumentation from the center of the yoke manipulators 102, 124, or otherwise attached thereto. A retraction handle may be used to retract the restraint 114 from the yoke manipulator. Removal of the restraint 114 frees the arms 110, which may be formed to spring open thereby releasing the retainer recesses 136. This requires adequate clearance between the manipulator arms 110 and the inner wall of the docking sleeve 34. Now, the manipulator assembly 141 may be removed.

The surgeon may now choose to perform any final operations through the docking sleeve 34 before removal. Removing the docking sleeve requires releasing the docking fasters 74, if employed and retracting the docking from the incision site. Appropriate wound closure techniques are then commenced.

In another embodiment, the docking sleeve 34 may include apertures, slots or other such features in the wall to permit passage of the connecting member 26 through the docking sleeve 34. As a further alternative, the fasteners 74 and docking sleeve 34 may be removed prior to the insertion of the connecting member 24. For example, the fasteners 74 and docking sleeve 34 may be removed just after the yoke manipulators 102, 124 are locked down on the yoke 22 with the restraint 114.

Another alternative would be to not use the docking sleeve 34 or the fasteners 74. In conjunction with or instead of incising the tissue along the guidewire 21, the surgeon may choose to use a single or series of progressively larger diameter obturators 36, guided by the guidewire, to stretch or open the tissues to a predetermined diameter. The surgeon may then continue the process of implanting the bone anchors 20 as described above albeit without the docking sleeve 34.

Preferably the MISS kit includes least two bone anchors or pedicle screws, which are inserted in the spinal anatomy with distal and proximal yoke manipulator assemblies 141 attached to each yoke 22. The guide cap 178 is locked on the proximal yoke manipulator assembly 141 using the bayonet connection. The guide 142 may then be positioned over the yoke manipulator assemblies 141 with the guide cap 178 seated within the proximal holder 162 and the connecting structure 120 within the distal holder 160. Locking cap 176 secures seating of the distal yoke manipulator assembly 141. The user adjusts the proximal holder 162 on the positioner 182 and may lock this position with manipulator lock 184. Proximal holder 162 is then adjusted within proximator guide 172 until the proximal and distal yoke manipulator assemblies 141 are generally parallel. The proximal lock is then applied to hold this position. The guide 142 may include etching as a quick reference for the user to choose an appropriate connecting member 26 length depending on the distance between the yoke manipulators.

The MISS connecting member 26 held in "position 1" of FIG. 33 and the rod inserter 140 is fed through the inserter guide 142 while the user holds both handle portions 156 adjacent to each other. The inserter 140 is fed through the slot 106 of the proximal yoke manipulator assembly 141, under the soft tissue of the patient, and into the yoke 22 of the distal pedicle screw implant as seen in FIG. 33. At this point, the rod inserter 140 is repositioned to "position 2" of FIG. 41, the handle portions 156 are permitted to be pivoted outward wherein the inserter guide no longer cradles the rod inserter 140. With the connecting rod 26 now pivotably attached to the rod inserter 140, the user guides the connecting rod 26 into the proximal yoke 22 perhaps viewing these movements through view ports 190. At this point the user preferably locks down the distal closure cap 24, then the proximal closure cap 24, using instruments and techniques described earlier. The inserter preferably is now repositioned to "position 3" of FIG. 40 and the rod inserter 140 is released from the connecting rod 26 and removed from the system. The remaining instrumentation may now be removed from the surgical site and the surgery may continue on the contralateral side if so desired.

While there have herein been illustrated and described with respect to specific examples, including presently preferred modes of carrying out the invention, those skilled in the art will appreciate that there are numerous variations and permutations of the above-described apparatus that fall within the scope and spirit of the invention as set forth in the appended claims.

The invention claimed is:

1. A method of securing a spinal rod to a vertebral bone, the method comprising:
forming a relatively small incision at a surgical site adjacent a first vertebral bone;
engaging a locking device of a pedicle screw assembly to a distal end portion of a first tool;
manipulating the pedicle screw assembly and spinal rod with surgical tools via the small incision, including:
securing the pedicle screw assembly to the first vertebral bone;
advancing the locking device into the small incision with the locking device connected to the distal end portion of the first tool;
turning the locking device of the pedicle screw assembly to a first predetermined rotary position in a yoke of the pedicle screw assembly using the first tool;
sliding a projecting pin of the first tool in a circumferentially extending slot of a tubular member until the pin abuts an end of the slot which restricts the first tool from turning the locking device beyond the first predetermined rotary position;
adjusting the spinal rod received in the yoke of the pedicle screw assembly with the locking device at the first predetermined rotary position;
disengaging the first tool from the locking device and withdrawing the first tool from the small incision;
advancing a second tool into the small incision and engaging the locking device with a distal end portion of the second tool;
turning the locking device beyond the first predetermined rotary position to clamp the spinal rod in the yoke using the second tool;
sliding a projecting pin of the second tool in the circumferentially extending slot of the tubular member until the pin abuts the end of the slot which restricts the second tool from turning the locking device beyond a second predetermined rotary position; and
confining a guideway through the small incision through which tools manipulate the pedicle screw assembly and the spinal rod with viewing of the pedicle screw assembly and spinal rod during manipulation being obstructed by the confined guideway and tool or tools therein.

2. The method of claim 1, wherein the turning of the locking device beyond the first rotary position includes restricting the turning of the locking device at the second predetermined rotary position beyond the first predetermined rotary position and at which the spinal rod is clamped in the yoke.

3. The method of claim 1, including:
securing a pedicle screw assembly to a second vertebral bone;
clamping a portion of the spinal rod to the pedicle screw assembly secured to the second vertebral bone prior to adjusting another portion of the spinal rod in the yoke of the pedicle screw assembly secured to the first vertebral bone.

4. The method of claim 1, wherein the turning of the locking device beyond the first predetermined rotary position includes restricting a turned portion of the locking device against axial translation as the locking device is turned beyond the first predetermined rotary position.

5. The method of claim 1, wherein the turning of the locking device beyond the first predetermined rotary position includes driving a lower rod engaging portion of the locking device into clamping engagement with the spinal rod.

6. The method of claim 5, wherein the driving the lower rod engaging portion of the locking device into clamping engagement with the spinal rod includes restricting rotation of the lower rod engaging portion during turning of an upper portion of the locking device.

7. The method of claim 6, wherein the driving the lower rod engaging portion of the locking device into clamping engagement with the spinal rod includes turning of the locking device beyond the first predetermined rotary position to the second predetermined rotary position and restricting a turned portion of the locking device against axial translation as the locking device is turned to the second predetermined rotary position.

8. The method of claim 5, wherein the lower rod engaging portion of the locking device is driven into clamping engagement by camming a turned upper portion of the locking device against the lower rod engaging portion during turning of the locking device beyond the first predetermined rotary position.

9. The method of claim 1, wherein the turning of the locking device of the pedicle screw assembly to the first predetermined rotary position includes:
inserting the first tool through the confined guideway;
engaging the first tool with the locking device; and
using the first tool to turn the locking device to the first predetermined rotary position.

10. The method of claim 9, wherein the turning of the locking device of the pedicle screw assembly beyond the first predetermined rotary position includes:
withdrawing the first tool from the confined guideway;
inserting the second tool through the confined guideway;
engaging the locking device with the second tool; and
using the second tool to turn the locking device beyond the first predetermined rotary position to clamp the spinal rod in the yoke.

11. A method of securing a spinal rod to a vertebral bone, the method comprising:
forming a relatively small incision at a surgical site adjacent a first vertebral bone;
aligning a pair of axially extending slots of an elongate yoke manipulator with a recess of a yoke of a pedicle screw assembly;
engaging a pair of spaced arms of the yoke manipulator with the pedicle screw yoke to releasably connect the yoke manipulator to the pedicle screw with the slots of the yoke manipulator aligned with the recess of the yoke;
aligning a pair of axially extending slots of a locking sleeve with the slots of the yoke manipulator;
passing the locking sleeve over the yoke manipulator and toward the spaced arms thereof to restrict outward movement of the arms and maintain engagement between the yoke manipulator and the pedicle screw;
inserting the pedicle screw assembly and a distal portion of the yoke manipulator through the small incision to engage the pedicle screw assembly with the first vertebral bone;
confining a guideway through the small incision through which a tool or tools manipulate the pedicle screw assembly and spinal rod so that viewing the pedicle screw assembly and the spinal rod through the confined guideway is obstructed by the tool or tools therein;
advancing a leading end of the spinal rod in a direction transverse to the length of the yoke manipulator through the aligned slots of the locking sleeve and the yoke manipulator and across an axial bore of the yoke manipulator such that a portion of the spinal rod is aligned with the recess of the pedicle screw yoke;
turning a locking device of the pedicle screw assembly secured to the vertebral bone with a driving tool extending in the confined guideway for clamping the spinal rod to the pedicle screw assembly; and
providing feedback to a user of the driving tool upon turning of the locking device to a predetermined rotary position indicating that the spinal rod is clamped so that viewing of the locking device and spinal rod through the obstructed guideway to determine the clamping of the spinal rod is unnecessary.

12. The method of claim 11 wherein the feedback to a user of the driving tool is provided by generating tactile feedback to the driving tool user upon turning of the locking device to the predetermined rotary position.

13. The method of claim 12 wherein the generating of tactile feedback further includes sliding a transversely projecting pin of the driving tool in a circumferentially extending slot of the confined guideway until the pin abuts an end of the slot.

14. The method of claim 13, wherein the turning of the locking device for clamping the spinal rod includes stopping rotation of the locking device at the predetermined rotary position at which the pin of the driving tool is abutting the end of the slot of the confined guideway.

15. The method of claim 14, wherein the stopping of the rotation of the locking device includes abutting a lower rod engaging portion against a stop of a turned upper portion of the locking device.

16. The method of claim 11, wherein the turning of the locking device for clamping the spinal rod includes driving a lower rod engaging portion of the locking device into clamping engagement with the spinal rod.

17. The method of claim 16, wherein the lower rod engaging portion of the locking device is driven into clamping engagement by camming a turned upper portion of the locking device against the lower rod engaging portion during turning of the locking device.

18. The method of claim 11, wherein the turning of the locking device for clamping the spinal rod includes restricting a turned portion of the locking device against axial translation as the locking device is turned.

19. The method of claim 11, including:
turning the locking device to an initial rotary position prior to the turning of the locking device to the predetermined rotary position at which the spinal rod is clamped;
adjusting the position of the spinal rod in a yoke of the pedicle screw assembly when the locking device is at the initial rotary position; and
limiting the turning of the locking device beyond the initial rotary position until after the adjusting of the position of the spinal rod in the yoke.

20. The method of claim 19, wherein the turning of the locking device to the initial rotary position includes restricting a turned portion of the locking device against axial translation as the locking device is turned to the initial rotary position.

21. The method of claim 19, wherein the turning of the locking device of the pedicle screw assembly to the initial rotary position includes:
inserting a pre-clamp tool through the confined guideway;
engaging the pre-clamp tool with the locking device; and
using the pre-clamp tool to turn the locking device to the initial rotary position.

22. The method of claim 21, wherein the turning of the locking device of the pedicle screw assembly to the predetermined rotary position includes:
withdrawing the pre-clamp tool from the confined guideway after the using of the pre-clamp tool to turn the locking device to the initial rotary position;
engaging the locking device with the driving tool; and
using the driving tool to turn the locking device from the initial rotary position to the predetermined rotary position after the adjusting of the position of the spinal rod in the yoke of the pedicle screw assembly.

23. The method of claim 11, including:
securing a pedicle screw assembly to a second vertebral bone; and clamping a portion of the spinal rod to the pedicle screw assembly secured to the second vertebral bone prior to turning of the locking device to the predetermined rotary position at which the spinal rod is clamped to the pedicle screw assembly secured to the first vertebral bone.

24. The method of claim 23, including:
turning the locking device to an initial rotary position prior to the turning of the locking device to the predetermined rotary position at which the spinal rod is clamped to the pedicle screw assembly secured to the first vertebral bone and after the clamping of the portion of the spinal rod to the pedicle screw assembly secured to the second vertebral bone; and
adjusting the position of the spinal rod in the yoke of the pedicle screw assembly secured to the first vertebral bone when the locking device is at the initial rotary position.

25. A method of securing a spinal rod to a vertebral bone, the method comprising:
forming a relatively small incision at a surgical site adjacent a first vertebral bone;
aligning a pair of axially extending slots of an elongate yoke manipulator with a recess of a yoke of a pedicle screw assembly;
engaging a pair of spaced arms of the yoke manipulator with the pedicle screw yoke to releasably connect the yoke manipulator to the pedicle screw with the slots of the yoke manipulator aligned with the recess of the yoke;
aligning a pair of axially extending slots of a locking sleeve with the slots of the yoke manipulator;
passing the locking sleeve over the yoke manipulator and toward the spaced arms thereof to restrict outward movement of the arms and maintain engagement between the yoke manipulator and the pedicle screw;
inserting the pedicle screw assembly and a distal portion of the yoke manipulator through the small incision to engage the pedicle screw assembly with the first vertebral bone;
advancing a leading end portion of the spinal rod in a direction transverse to the length of the yoke manipulator through the aligned slots of the locking sleeve and the yoke manipulator and across an axial bore of the yoke manipulator such that a portion of the spinal rod is aligned with the recess of the pedicle screw yoke;
connecting a locking device of the pedicle screw assembly to a distal end portion of an insertion tool;
moving the locking device and the distal end portion of the insertion tool along the axial bore of the yoke manipulator; and
engaging the locking device with the yoke of the pedicle screw assembly to secure the spinal rod within the yoke with viewing of the pedicle screw assembly and spinal rod through the confined guideway being obstructed by the locking device and the insertion tool.

26. The method of claim 25, including:
withdrawing the distal end portion of the insertion tool through the axial bore of the yoke manipulator;
passing the locking sleeve over the yoke manipulator away from the spaced arms thereof to permit outward movement of the arms; and
disengaging the arms of the yoke manipulator from the pedicle screw yoke and removing the yoke manipulator from the small incision.

27. The method of claim 25, including:
securing a pedicle screw assembly to a second vertebral bone;
advancing the leading end portion of the spinal rod through an entrance slot of a yoke manipulator connected to the pedicle screw assembly secured to the second vertebral bone; and
engaging a locking device with a yoke of the pedicle screw assembly secured to the second vertebral bone to secure the spinal rod within the yoke.

28. The method of claim 25, including:
turning the locking device of the pedicle screw assembly to an initial rotary position using the insertion tool;
adjusting the position of the spinal rod in the yoke of the pedicle screw assembly when the locking device is in the initial rotary position;
withdrawing the distal end portion of the insertion tool through the axial bore of the yoke manipulator;
advancing a distal end portion of a final driver tool through the axial bore;
engaging the locking device with the final driver tool; and
turning the locking device of the pedicle screw assembly to a predetermined rotary position where the spinal rod is clamped beyond the initial rotary position using the final driver tool.

* * * * *